(12) United States Patent
Halter et al.

(10) Patent No.: US 10,206,632 B2
(45) Date of Patent: Feb. 19, 2019

(54) SYSTEMS AND METHODS FOR CARDIOVASCULAR-DYNAMICS CORRELATED IMAGING

(71) Applicant: THE TRUSTEES OF DARTMOUTH COLLEGE, Hanover, NH (US)

(72) Inventors: Ryan J. Halter, Lyme, NH (US); Keith D. Paulsen, Hanover, NH (US); Alexander Hartov, Enfield, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 11 days.

(21) Appl. No.: 15/328,981

(22) PCT Filed: Jul. 27, 2015

(86) PCT No.: PCT/US2015/042306
§ 371 (c)(1),
(2) Date: Jan. 25, 2017

(87) PCT Pub. No.: WO2016/015057
PCT Pub. Date: Jan. 28, 2016

(65) Prior Publication Data
US 2017/0224288 A1    Aug. 10, 2017

Related U.S. Application Data

(60) Provisional application No. 62/028,949, filed on Jul. 25, 2014.

(51) Int. Cl.
*G06K 9/00* (2006.01)
*A61B 5/00* (2006.01)
(Continued)

(52) U.S. Cl.
CPC .......... *A61B 5/7289* (2013.01); *A61B 5/0205* (2013.01); *A61B 5/02416* (2013.01);
(Continued)

(58) Field of Classification Search
CPC .......... A61B 5/02; A61B 5/50; A61B 6/0306; A61B 6/504; A61B 5/7289; A61B 5/7246;
(Continued)

(56) References Cited

U.S. PATENT DOCUMENTS

2005/0042602 A1* 2/2005 Ahearn .................. G01N 33/80
435/5
2006/0265022 A1* 11/2006 John .................. A61B 5/14553
607/45
(Continued)

OTHER PUBLICATIONS

Acharya et al. (2006) "Heart rate variability: a review," Med. Bio. Eng. Comput. 44:1031-1051.
(Continued)

*Primary Examiner* — Amir Alavi
(74) *Attorney, Agent, or Firm* — Lathrop Gage LLP

(57) ABSTRACT

A method for cardiovascular-dynamics correlated imaging includes receiving a time series of images of at least a portion of a patient, receiving a time series of cardiovascular data for the patient, evaluating correlation between the time series of images and the time series of cardiovascular data, and determining a property of the at least a portion of a patient, based upon the correlation. A system for cardiovascular-dynamics correlated imaging includes a processing device having: a processor, a memory communicatively coupled therewith, and a correlation module including machine-readable instructions stored in the memory that, when executed by the processor, perform the function of correlating a time series of images of at least a portion of a patient with a time series of cardiovascular data of the patient to determine a property of the at least a portion of a patient.

18 Claims, 32 Drawing Sheets

(51) Int. Cl.
  *A61B 5/0205*  (2006.01)
  *A61B 5/053*  (2006.01)
  *A61B 6/00*  (2006.01)
  *A61B 5/055*  (2006.01)
  *G06T 7/00*  (2017.01)
  *A61B 5/024*  (2006.01)
  *A61B 5/1455*  (2006.01)
  *G06F 19/00*  (2018.01)
  *A61B 6/03*  (2006.01)
  *A61B 5/0245*  (2006.01)
  *A61B 5/026*  (2006.01)

(52) U.S. Cl.
  CPC ............ *A61B 5/055* (2013.01); *A61B 5/0536* (2013.01); *A61B 5/14551* (2013.01); *A61B 5/7246* (2013.01); *A61B 6/463* (2013.01); *A61B 6/486* (2013.01); *A61B 6/487* (2013.01); *A61B 6/502* (2013.01); *A61B 6/503* (2013.01); *A61B 6/504* (2013.01); *A61B 6/5235* (2013.01); *A61B 6/5247* (2013.01); *A61B 6/5288* (2013.01); *G06F 19/00* (2013.01); *G06T 7/0016* (2013.01); *A61B 5/024* (2013.01); *A61B 5/0245* (2013.01); *A61B 5/0261* (2013.01); *A61B 6/032* (2013.01); *A61B 6/037* (2013.01); *A61B 6/469* (2013.01); *G06T 2207/30048* (2013.01); *G06T 2207/30068* (2013.01)

(58) Field of Classification Search
  CPC ... G06T 7/0012; G06T 7/0081; G06T 11/003; G06T 2207/10081; G06T 2207/10056
  See application file for complete search history.

(56) References Cited

U.S. PATENT DOCUMENTS

| | | | |
|---|---|---|---|
| 2007/0060821 A1* | 3/2007 | Cohn ...................... | A61B 5/02 600/481 |
| 2007/0066898 A1 | 3/2007 | Hendriks et al. | |
| 2008/0027330 A1* | 1/2008 | Naghavi .............. | A61B 5/0402 600/481 |
| 2009/0262999 A1 | 10/2009 | Shinagawa et al. | |
| 2010/0041963 A1* | 2/2010 | Haider .................. | G06T 7/0012 600/301 |
| 2010/0062431 A1* | 3/2010 | Kozian ................ | C12Q 1/6883 435/6.16 |
| 2010/0087738 A1 | 4/2010 | Fornwalt et al. | |
| 2010/0185085 A1 | 7/2010 | Hamilton | |
| 2010/0222652 A1* | 9/2010 | Cho ......................... | A61B 5/00 600/301 |
| 2011/0034806 A1 | 2/2011 | Hartov et al. | |
| 2012/0161782 A1 | 6/2012 | Ross | |
| 2013/0123617 A1 | 5/2013 | Sola I Caros et al. | |
| 2013/0184581 A1 | 7/2013 | Hendriks et al. | |
| 2013/0245441 A1 | 9/2013 | Datta | |
| 2016/0256277 A1* | 9/2016 | Ku ......................... | A61F 2/2475 |
| 2017/0251931 A1* | 9/2017 | Prakash .............. | A61B 5/02007 |
| 2017/0343464 A1* | 11/2017 | Guadagno .......... | G01N 15/1031 |

OTHER PUBLICATIONS

Assenheimer et al. (2001) "The T-Scan technology: electrical impedance as a diagnostic tool for breast cancer detection," Physiological Measurement. 22:1-8.
Bäuerle et al. (2010) "Imaging anti-angiogenic treatment response with DCE-VCT, DCE-MRI and DWI in an animal model of breast cancer bone metastasis," European Journal of Radiology. 73:280-287.
Beving et al. (1994) "Dielectric properties of human blood and erythrocytes at radio frequencies (0.2-10MHz); dependence on cell volume fraction and medium composition," Eur. Biophys. J. 23:207-215.
Brurberg et al. (2008) "Temporal heterogeneity in blood supply in human tumor xenografts," Neoplasia. 10:727-735.
Chen et al. (May 20, 2014) "Multi-channel electrical impedance tomography for regional tissue hydration monitoring," Physiol. Meas. 35(6):1137-47.
Cheney et al. (1999) "Electrical impedance tomography," SIAM Review. 41:85-101.
Cherepenin et al. (2001) "A 3D electrical impedance tomography (EIT) system for breast cancer detection," Physiological Measurement. 22:9-18.
Cherepenin et al. (2002) "Three-dimensional Eit imaging of breast tissues: System design and clinical testing," IEEE Transactions on Medical Imaging. 21:662-667.
Delille et al. (2002) "Breast cancer: Regional blood flow and blood volume measured with magnetic susceptibility-based MR imaging—initial results," Radiology. 223:558-565.
Drägerwerk AG & Co."Dräger PulmoVista® 500," Dräger. https://www.draeger.com/en_uk/Hospital/Products/Ventilation-and-Respiratory-Monitoring/ICU-Ventilation-and-Respiratory-Monitoring/PulmoVista-500, 5 pgs. [Last Accessed Oct. 17, 2017].
Du et al. (2008) "Microvascular architecture of breast lesions: evaluation with contrast-enhanced ultrasonographic micro flowimaging," J. Ultrasound Med. 27:833-842.
Dvorak et al. (1998) "Identification and characterization of the blood vessels of solid tumors that are leaky to aircirculating macromolecules," Am. J. Pathology. 133:95-109.
Eskey et al. (1992) "2H-Nuclear magnetic resonance imaging of tumor blood flow: spatial temporal heterogeneity in a tissue-isolated mammary adenocarcinoma," Cancer Research. 52:6010-6019.
Folkman (2006) "Angiogenesis," Annu. Rev. Med. 57:1-18.
Forsberg et al. (2011) "Contrast enhanced maximum intensity projection ultrasound imaging for assessing angiogenesis in murine glioma and breast tumor models: A comparative study," Ultrasonics. 51:382-389.
Frerichs (2000) "Electrical impedance tomography (EIT) in applications related to lung and ventilation: a review of experimental and clinical activities," Physiological Measurement. 21:R1-R21.
Fukumura et al. (2007) "Tumor microvasculature and microenvironment: targets for anti-angiogenesis and normalization," Microvascular Research. 74:72-84.
Gaw et al. (2008) "The electrical impedance of pulsatile blood flowing through rigid tubes: a theoretical investigation," IEEE Trans. Biomed. Eng. 55:721-727.
Giatromanolaki et al. (2002) "Differential assessment of vascular survival ability and tumor angiogenic activity in colorectal cancer," Clin. Cancer Res. 8:1185-1191.
Goel et al. (2011) "Normalization of the vasculature for treatment of cancer and other diseases," Physiological Reviews. 91:1071-121.
Halter et al. (2008) "A broadband high frequency electrical impedance tomography system for breast imaging," IEEE Trans. Biomed. Eng. 55:650-659.
Halter et al. (2008) "Video rate electrical impedance tomography of vascular changes: preclinical development," Physiol. Meas. 29(3):349-364.
Halter et al. (Jul. 24, 2014) "Real-time electrical impedance variations in women with and without breast cancer," IEEE Trans. Med. Imaging. 34(1):38-48.
Henderson et al. (2000) "Simultaneous MRI measurement of blood flow, blood volume, and capillary permeability in mammary tumors using two different contrast agents," Journal of Magnetic Resonance Imaging. 12:991-1003.
Huang et al. (2012) "Vascular normalizing doses of antiangiogenic treatment reprogram the immunosuppressive tumor microenvironment and enhance immunotherapy," Proc. Natl. Acad. Sci. USA. 109:17561-17566.
Ikeda et al. (2004) "Evaluation of tumor angiogenesis using dynamic enhanced magnetic resonance imaging: Comparison of plasma vascular endothelial growth factor, hemodynamic, and pharmacokinetic parameters," Acta Radiology. 45:446-452.
Isaacson (1986) "Distinguishability of Conductivities by Electric Current Computed Tomography," IEEE Trans. Med. Imaging. 5:91-95.

(56) References Cited

OTHER PUBLICATIONS

Jackson et al. (2007) "Imaging tumor vascular heterogeneity and angiogenesis using dynamic contrast-enhanced magnetic resonance imaging," Clinical Cancer Research. 13:3449-3459.
Jain (2003) "Molecular regulation of vessel maturation," Nat. Med. 9:685-693.
Jain (2005) "Normalization of tumor vasculature: an emerging concept in antiangiogenic therapy," Science. 307:58-62.
Jossinet (1996) "Variability of impedivity in normal and pathological breast tissue," Med. & Biol. Eng. & Comput. 34:346-350.
Jossinet (1998) "The impedivity of freshly excised human breast tissue," Physiol. Meas. 19:61-75.
Kao et al. (2008) "Regional Admittivity Spectra With Tomosynthesis Images for Breast Cancer Detection: Preliminary Patient Study," IEEE Trans. Med. Imaging. 27(12):1762-1768.
Kerner et al. (2002) "Electrical Impedance Spectroscopy of the breast: Clinical imaging results in 26 subjects," IEEE Transactions on Medical Imaging. 21:638-645.
Kerner et al. (2002) "Imaging the breast with EIS: an initial study of exam consistency," Physiological Measurement. 23:221-236.
Kerrouche et al. (2001) "Time series of Eit chest images using singular value decomposition and Fourier transform," Physiological Measurement. 22:147-157.
LaGalla et al. (1998) "Monitoring treatment response with color and power Doppler," European Journal of Radiology. 28:S149-S156.
Li et al. (Jul. 2013) "Perfusion Heterogeneity in Breast Tumors for Assessment of Angiogenesis," Journal of Ultrasound in Medicine. 32:1145-1155.
Lominadze et al. (1999) "Red blood cell behavior at low flow rate in microvessels," Microvascular Research. 58:187-189.
Mackey et al. (2012) "Controlling angiogenesis in breast cancer: a systematic review of anti-angiogenic trials," Cancer Treatment Reviews. 38:673-688.
Magnon et al. (2007) "Dynamic assessment of antiangiogenic therapy by monitoring both tumoral vascularization and tissue degeneration," Gene Therapy. 14:108-117.
Malich et al. (2000) "Electrical impedance scanning for classifying suspicious breast lesions: first results," European Radiology. 10:1555-1561.
Malich et al. (2001) "Additional value of electrical impedance scanning: evaluation of 240 histologically-proven breast lesions," European Journal of Cancer. 37:2324-2330.
McArdle et al. (1989) "Imaging resistivity changes of the adult brain during the cardiac cycle," In; The Proceedings of the Annual International Conference of the IEEE Engineering in Engineering in Medicine and Biology Society, 1989. Images of the Twenty-First Century.
Milz et al. (2001) "Evaluation of breast lesions by power Doppler sonography," European Journal of Radiology. 11(4):547-54.
Nakae et al. (1999) "Effects of aging and gastric lipolysis on gastric emptying of lipid in liquid metal," Journal of Gastroenterology. 34:445-449.
Oh et al. (2007) "Multi-frequency EIT system with radially symmetric architecture: KHU Mark1" Physiol. Meas. 28: S183-S196.
Osterman et al. (2000) "Multifrequency electrical impedance imaging: preliminary in vivo experience in breast," Physiological Measurement. 21:99-109.
Peters-Engl et al. (1998) "Color-coded and spectral Doppler flow in breast carcinoma—Relationships with the tumor microvasculature," Breast Cancer Research and Treatment. 47:83-89.
Peters-Engl et al. (1999) "Tumor flow in malignant breast tumors measured by Dopler ultrasound: an independent predictor of survival," Breast Cancer Research and Treatment 54:65-71.
Polydorides et al. (2002) "A Matlab toolkit for three-dimensional electrical impedance tomography: a contribution to the Electrical Impedance and Diffuse Optical Reconstruction Software project," Meas. Sci. Technol. 13:1871-1883.
Poplack et al. (2007) "Electromagnetic Breast Imaging: Results of a Pilot Study in Women with Abnormal Mammograms," Radiology. 243:350-359.
Popovic et al. (Apr. 2013) "Assessment of cerebral blood flow autoregulation (CBF AR) with rheoencephalography (REG): studies in animals," Journal of Physics: Conference Series. 434:012042. pp. 1-4.
Rajendran et al. (2005) "Imaging hypoxia and angiogenesis in tumors," Radiol. Clin. N. Am. 43:169-187.
Ribatti et al. (2007) "The structure of the vascular network of tumors," Cancer Letters. 248:18-23.
Sakamoto et al. (1979) "Electrical characteristics of flowing blood," IEEE Trans. Biomed. Eng. 26(12):686-95.
Saslow et al. (2007) "American Cancer Society guidelines for breast screening with MRI as an adjunct to mammography," CA Cancer J. Clin. 57:75-89.
Saulnier et al. (Aug. 2007) "An electrical impedance spectroscopy system for breast cancer detection," In; The Proc. 29th Ann Int Conf. IEEE Eng. Med. Biol. Soc. 2007:4154-4157.
Seo et al. (2008) "Frequency-difference electrical impedance tomography (fdEIT): algorithm development and feasibility study," Physiol. Meas. 29:929-944.
Sherwood et al. (1990) "Methodological guidelines for impedance cardiography," Psychophysiology. 27(1):1-23.
Stojadinovic et al. (2006) "Prospective study of electrical impedance scanning for identifying young women at risk for breast cancer," Breast Cancer Research and Treatment. 97:179-189.
Stojadinovic et al. (2008) "Electrical impedance scanning as a new breast cancer risk stratification tool for young women," Journal of Surgical Oncology. 97:112-120.
Stomper et al. (1997) "Angiogenesis and dynamic Mr imaging gadolinium enhancement of malignant and benign breast lesions," Breast Cancer Research and Treatment. 45:19-46.
Taylor et al. (1999) "Mr imaging of tumor microcirculation: Promise for the new millenium," Journal of Magnetic Resonance Imaging. 10:903-907.
Tidswell et al. (2001) "Three-dimensional electrical impedance tomography of human brain activity," NeuroImage. 13:283-294.
Trokhanova et al. (2008) "Dual-frequency electrical impedance mammography for the diagnosis of non-malignant breast disease," Physiological Measurement. 29:S331-S344.
Tuncbilek et al. (2003) "Evaluation of tumor angiogenesis with contrast-enhanced dynamic magnetic resonance mammography," The Breast Journal. 9:403-408.
Turetschek et al. (2001) "Assessment of a rapid clearance blood pool MR contrast medium (P792) for assays on microvascular characteristics in experimental breast tumors with correlations to histopathology," Magnetic Resonance in Medicine. 45:880-886.
Turetschek et al. (2004) "Tumor microvascular changes in antiangiogenic treatment: assessment by magnetic resonance contrast media of different molecular weights," J. Magn. Reson. Imaging. 20:138-144.
UBM MEDICA, LLC (Sep. 13, 2000) "Siemens and TransScan extend partnership," Press Release. Diagnostic Imaging. Accessible on the Internet at URL: http://www.diagnosticimaging.com/articles/siemens-and-transscan-extend-partnership, 2 pgs. [Last Accessed Oct. 17, 2017].
Vaisman et al. (1999) "Gastric emptying in patients with type 1 diabetes mellitus," Annals of NY Academy of Science. 873:506-511.
Vaupel et al. (2007) "Detection and characterization of tumor hypoxia using pO2 histography," Antioxidants & Redox Signaling. 9:1221-1235.
Vreugdenburg et al. (Jan. 4, 2013) "A systematic review of elastography, electrical impedance scanning, and digital infrared thermography for breast cancer screening and diagnosis," Breast Cancer Research and Treatment. 137:665-676.
Wells et al. (2004) "Analysis of the microvasculature and tissue type ratios in normal vs. benign and malignant breast tissue," Analytical and Quantitative Cytology and Histology. 26:166-174.
Yang et al. (2002) "Correlation between color power Doppler sonographic measurement of breast tumor vascular and immunohistochemical analysis of microvessel density for the quantitation of angiogenesis," J. Ultrasound Med. 21:1227-1235.
Yuan et al. (1994) "Vascular permeability and microcirculation of gliomas and mammary carcinomas transplanted in rat and mouse cranial windows," Cancer Research. 54:4565-4568.

(56) References Cited

OTHER PUBLICATIONS

Zou et al. (2003) "A review of electrical impedance techniques for breast cancer detection," Medical Engineering and Physics. 25:79-90.
International Search Report with Written Opinion corresponding to International Patent Application No. PCT/US2015/042306, dated Oct. 29, 2015, 11 pgs.

* cited by examiner

700

CALCULATE TEMPORAL CORRELATION COEFFICIENT, BETWEEN TIME SERIES OF IMAGES OR POSITION SENSITIVE SIGNALS AND TIME SERIES OF CARDIOVASCULAR DATA, AS A FUNCTION OF PHASE SHIFT BETWEEN TIME SERIES OF POSITION SENSITIVE SIGNALS AND TIME SERIES OF CARDIOVASCULAR DATA
710

DETERMINE AT LEAST ONE OF (A) MAXIMUM TEMPORAL CORRELATION COEFFICIENT AS A FUNCTION OF PHASE SHIFT AND (B) PHASE SHIFT AT WHICH MAXIMUM TEMPORAL CORRELATION COEFFICIENT IS ATTAINED
720

EVALUATE SPECTRAL DISTRIBUTION OF TIME SERIES OF POSITION SENSITIVE SIGNALS, REFLECTING CONSTANT HEARTBEAT RATE
810

CALCULATE ONE OR MORE POWER SPECTRAL RATIOS
812

FIG. 8

TABLE I
CANCER PATIENT CHARACTERISTICS

| Patient | | | | Patient Characteristic | | | | Correlative Measures | | | Power Spectral Ratios | | |
|---|---|---|---|---|---|---|---|---|---|---|---|---|---|
| | RD | Side | Quad | Size | Bx Path | Enhancement | Kinetics | $r_s$ | $\phi(r_{s,max})$ | $r_{s,max}$ | $P_{low,full}$ | $P_{high,full}$ | $P_{low,high}$ |
| 1 | HD | L | 3 | 33x22x33 | IDC | Rim | Malignant (washout) | -0.035 | 55 | -0.005 | 0.52 | 0.48 | 1.1 |
| 2 | SC | R | 1 | 42x27x35 | IDC | Heterogeneous | Mixed progressive/plateau | 0.515 | 82.8 | 0.082 | 0.65 | 0.35 | 1.8 |
| | | | 4 | | | | | 0.006 | 359 | 0.086 | 0.77 | 0.23 | 3.4 |
| 3 | HD | L | 2 | 19x18x15 | IDC | Heterogeneous | Malignant (washout) | -0.025 | 359 | 0.104 | 0.80 | 0.21 | 3.9 |
| 4 | HD | R | 4 | 39x26x42 | Inflammatory Ca | Heterogeneous | Mixed plateau/washout | 0.810 | 359 | 0.159 | 0.57 | 0.43 | 1.3 |
| 5 | ED | R | 4 | 30x30x25 | IDC | Heterogeneous | Mixed progressive/plateau | -0.030 | 83 | 0.094 | 0.69 | 0.31 | 2.2 |
| 6 | SC | R | 4 | 60x28x30 | IDC/DCIS | Heterogeneous | Mixed plateau/washout | -0.015 | 239 | 0.096 | 0.60 | 0.40 | 1.5 |
| 7 | HD | R | 1 | 27x18x34 | IDS/DCIS | Homogeneous | Mixed plateau/washout | 0.110 | 138 | 0.262 | 0.65 | 0.35 | 1.8 |
| 8 | ED | R | 1 | 35x45x100 | IDC | Heterogeneous | Malignant (washout) | 0.060 | 359 | 0.118 | 0.76 | 0.24 | 3.1 |
| | | | 4 | | | | | -0.005 | 331 | 0.070 | 0.85 | 0.15 | 5.7 |
| 9 | HD | R | 4 | 25 | IDC | n/a* | n/a* | 0.030 | 258 | 0.088 | 0.82 | 0.19 | 4.4 |
| 10 | SC | R | 1 | 42x27x35 | IDC | Heterogeneous | Mixed progressive/plateau | -0.081 | 55.2 | 0.042 | 0.64 | 0.36 | 1.8 |
| | | | 4 | | | | | -0.032 | 184 | 0.015 | 0.64 | 0.36 | 1.8 |

RD denotes Radiographic Density, Bx Path denotes biopsy based pathological findings, and Enhancement and Kinetics describe the washout dynamics of contrast-enhanced MR studies. ED = extremely dense, HD = heterogeneously dense, SC = scattered, DCIS = ductal carcinoma in situ, IDC = intraductal carcinoma. * no MRI obtained for this patient.

FIG. 16

TABLE II
STATISTICS OF NORMAL AND CANCER PATIENTS OBTAINED FROM PROCESSING OF EACH QUADRANT OF DATA

| | Cancer | | | | | | Benign | | | | | |
|---|---|---|---|---|---|---|---|---|---|---|---|---|
| | Correlative Measures | | | Power Spectral Ratios | | | Correlative Measures | | | Power Spectral Ratios | | |
| | $f_s$ | $\phi(t_{max})$ | $E_{t_{max}}$ | $P_{low:full}$ | $P_{high:full}$ | $P_{low:high}$ | $f_s$ | $\phi(t_{max})$ | $E_{t_{max}}$ | $P_{low:full}$ | $P_{high:full}$ | $P_{low:high}$ |
| Range Stats | | | | | | | | | | | | |
| Minimum | -0.081 | 0 | -0.005 | 0.52 | 0.15 | 1.07 | -0.072 | 0 | -0.011 | 0.23 | 0.10 | 0.30 |
| 25th Percentile | -0.030 | 83 | 0.070 | 0.64 | 0.23 | 1.75 | 0.047 | 64 | 0.128 | 0.51 | 0.32 | 1.02 |
| Median | -0.005 | 184 | 0.088 | 0.65 | 0.35 | 1.84 | 0.220 | 83 | 0.183 | 0.60 | 0.40 | 1.48 |
| 75th Percentile | 0.060 | 331 | 0.104 | 0.77 | 0.36 | 3.40 | 0.552 | 129 | 0.371 | 0.68 | 0.49 | 2.14 |
| Maximum | 0.810 | 359 | 0.262 | 0.85 | 0.48 | 5.69 | 0.978 | 359 | 0.460 | 0.90 | 0.77 | 9.35 |
| Mean Stats | | | | | | | | | | | | |
| Mean | 0.101 | 193 | 0.093 | 0.69 | 0.31 | 2.60 | 0.306 | 115 | 0.184 | 0.60 | 0.40 | 1.88 |
| SD | 0.261 | 133 | 0.066 | 0.10 | 0.10 | 1.39 | 0.300 | 96 | 0.087 | 0.13 | 0.13 | 1.40 |
| SE | 0.072 | 37 | 0.018 | 0.028 | 0.028 | 0.39 | 0.025 | 8 | 0.007 | 0.01 | 0.01 | 0.12 |
| 95% CI | | | | | | | | | | | | |
| Lower | -0.057 | 113 | 0.053 | 0.63 | 0.25 | 1.76 | 0.256 | 99 | 0.169 | 0.58 | 0.38 | 1.64 |
| Upper | 0.258 | 273 | 0.133 | 0.75 | 0.37 | 3.44 | 0.357 | 131 | 0.199 | 0.62 | 0.43 | 2.11 |

FIG. 20

TABLE III
CLINICAL METRICS FOR EACH OF THE EXTRACTED TEMPORAL AND SPECTRAL POWER PARAMETERS

| | AUC | Threshold | SN | SP | ACC | PPV | NPV | p-value |
|---|---|---|---|---|---|---|---|---|
| Dynamic Parameters | | | | | | | | |
| $r_s$ | 0.77 | 0.109 | 0.77 | 0.66 | 0.67 | 0.18 | 0.97 | 0.0091 |
| $\phi(r_{t,max})$ | 0.67 | 82.8 | 0.77 | 0.45 | 0.47 | 0.11 | 0.95 | 0.0040 |
| $r_{t,max}$ | 0.80 | 0.106 | 0.77 | 0.81 | 0.81 | 0.28 | 0.97 | 0.0002 |
| $P_{low,full}$ | 0.71 | 0.637 | 0.77 | 0.67 | 0.68 | 0.18 | 0.97 | 0.0098 |
| $P_{high,full}$ | 0.71 | 0.365 | 0.77 | 0.67 | 0.68 | 0.18 | 0.97 | 0.0098 |
| $P_{low,high}$ | 0.71 | 1.75 | 0.77 | 0.67 | 0.68 | 0.18 | 0.97 | 0.0389 |

FIG. 23

|  | Patient Number | Age at exam | BMI | Weight (lb) | Height (in) | Radiographic Density |
|---|---|---|---|---|---|---|
| Abnormal Cohort | 1 | 48 | 25.2 | 125 | 60 | HD |
| | 2 | 48 | 34.5 | 220 | 67 | SD |
| | 3 | 49 | 21.6 | 117 | 62 | HD |
| | 4 | 60 | 28.6 | 164 | 64 | HD |
| | 5 | 41 | 23.1 | 134 | 64 | ED |
| | 6 | 69 | 39.2 | 243 | 66 | SD |
| | 7 | 69 | 28.0 | 167 | 65 | HD |
| | 8 | 51 | 22.9 | 134 | 64 | ED |
| | 9 | 60 | 22.2 | 127 | 64 | HD |
| Normal Cohort | 10 | 52 | 28.3 | 155 | 62 | SD |
| | 11 | 60 | 26 | 147 | 63 | SD |
| | 12 | 39 | 27 | 138 | 60 | unknown |
| | 13 | 54 | 26.5 | 140 | 61 | HD |
| | 14 | 56 | 24.9 | 145 | 64 | HD |
| | 15 | 51 | 22.3 | 130 | 64 | HD |
| | 16 | 57 | 29.3 | 160 | 62 | SD |
| | 17 | 53 | 24 | 127 | 61 | ED |
| | 18 | 46 | 30.6 | 201 | 68 | HD |

FIG. 24

| Patient Number | Abn. side | Involved quadrants | Size (mm×mm×mm) | Lesion Shape | Lesion Margins | Enhancement | Kinetics | ACR | Biopsy Pathology |
|---|---|---|---|---|---|---|---|---|---|
| 1 | L | 3 | 33 × 22 × 33 | Irregular | Spiculated | Rim | Malignant (washout) | 6 | IDC |
| 2 | R | 1,4 | 42 × 27 × 35 | Irregular | Irregular | Heterogeneous | Mixed progressive/plateau | 6 | Invasive mucinous (colloid) carcinoma |
| 3 | L | 2 | 19 × 18 × 15 | Ellipse | Irregular | Heterogeneous | Malignant (washout) | 6 | IDC with metaplastic features |
| 4 | R | 4 | 39 × 26 × 42 | Spiculated | Irregular | Heterogeneous | Mixed plateau/washout | 6 | Invasive carcinoma with ductal features |
| 5 | R | 4 | 30 × 30 × 25 | Irregular | Irregular | Heterogeneous | Mixed progressive/plateau | 6 | IDC |
| 6 | R | 4 | 60 × 28 × 30 | Lobulated | Irregular | Heterogeneous | Mixed plateau/washout | 6 | IDC/DCIS |
| 7 | R | 1 | 27 × 18 × 34 | Irregular | Spiculated | Homogeneous | Mixed plateau/washout | 6 | IDC/DCIS |
| 8 | R | 1,4 | 35 × 45 × 100 | Irregular | Irregular | Heterogeneous | Malignant (washout) | 6 | IDC |
| 9* | R | 4 | 19 | oval | n/a | n/a | n/a | 4B | Benign breast parenchyma |

FIG. 25

| Patient Number | Abn. side | Correlation Coefficient (right) | Correlation Coefficient (left) | Γbenign:Γabnormal ratio |
|---|---|---|---|---|
| 1 | L | 0.2093 | 0.0081 | 25.84 |
| 2 | R | 0.0068 | 0.1204 | 17.71 |
| 3 | L | 0.1084 | 0.0149 | 7.28 |
| 4 | R | 0.0049 | 0.0287 | 5.86 |
| 5 | R | 0.0929 | 0.1774 | 1.91 |
| 6 | R | 0.0454 | 0.0092 | 0.20 |
| 7 | R | 0.335 | 0.0804 | 2.40 |
| 8 | R | 0.0632 | 0.2182 | 3.45 |
| 9* | R | 0.0795 | 0.0723 | 0.91 |

FIG. 28

SYSTEMS AND METHODS FOR CARDIOVASCULAR-DYNAMICS CORRELATED IMAGING

CROSS-REFERENCE TO RELATED APPLICATIONS

The present application is a 35 U.S.C. § 371 filing of International Application No. PCT/US2015/042306, filed Jul. 27, 2015, which claims the benefit of priority from U.S. Provisional Application Ser. No. 62/028,949 filed Jul. 25, 2014, each of which is incorporated herein by reference in its entirety.

U.S. GOVERNMENT SUPPORT

This invention was made with government support under contract Nos. CA080139 and CA143020 awarded by the National Institutes of Health. The government has certain rights in the invention.

BACKGROUND

Physicians commonly utilize imaging in the diagnosis, treatment, and monitoring of medical conditions. Various imaging methods are capable of distinguishing between at least some types of materials in a human body. For example, magnetic resonance imaging (MRI) may distinguish between bone material, organs, and various forms of soft tissue. Ultrasound may distinguish an internal organ from surrounding parts of a human body. Contrast imaging is the imaging of a contrast agent delivered to the tissue or material of interest. The contrast agent is administered to the patient before or during imaging and predominantly binds to or occupies certain types of materials. These materials are thereby enhanced in the images. Contrast imaging is utilized to image tissue vascularization. In this case, a contrast agent is delivered to the cardiovascular system of the patient. Detection and evaluation of tissue vascularization is used to diagnose and monitor conditions such as hemangioma, vascular anomalies, and cancer.

Notably, vascularization properties of a malignant tumor tend to be different from those of healthy tissue and benign tumors. The vascularization topology of a malignant breast tumor, as well as the blood flow properties of the vessels, differs from that of healthy breast tissue. The normal breast is vascularized with a well-organized and regular network of vessels. On the other hand, the vasculature around a malignant tumor is of irregular size, shape, and branching pattern, and lacks the vascular network hierarchy of healthy breast tissue. In addition, individual vessels are compromised. These features of a malignant tumor result in, for example, lower blood flow rates than in healthy tissue, chaotic blood flow around the malignant tumor, and diffusion of blood plasma into the surrounding tissue.

Tumor vascularization imaging may detect a malignant tumor or distinguish a benign breast tumor from a malignant breast tumor. Tumor vascularization imaging may also monitor tumor angiogenesis (the formation of new blood-vessels from existing blood vessels) as a tool to stage disease progression or as a tool to monitor disease progression during an anti-angiogenic treatment course.

SUMMARY

In an embodiment, a method for cardiovascular-dynamics correlated imaging includes (a) receiving a time series of images of at least a portion of a patient, (b) receiving a time series of cardiovascular data for the patient, (c) evaluating correlation between the time series of images and the time series of cardiovascular data, and (d) determining a property of the at least a portion of a patient, based upon the correlation between the time series of images and the time series of cardiovascular data.

In an embodiment, a system for cardiovascular-dynamics correlated imaging includes a processing device having (a) a processor, (b) a memory communicatively coupled with the processor, and (c) a correlation module including machine-readable instructions stored in the memory that, when executed by the processor, perform the function of correlating a time series of images of at least a portion of a patient with a time series of cardiovascular data of the patient to determine a property of the at least a portion of a patient.

BRIEF DESCRIPTION OF THE DRAWINGS

FIG. 7 illustrates a method for evaluating temporal correlation between a time series of images and a time series of cardiovascular data, according to an embodiment.

FIG. 8 illustrates a method for evaluating spectral correlation between a time series of images and a time series of cardiovascular data, according to an embodiment.

FIG. 16 shows tumor characteristics for cancer containing quadrants of breasts of a cohort of patients.

FIG. 20 shows, in tabular form, statistics of normal and cancer patient obtained from processing of exemplary quadrant.

FIG. 23 shows, in tabular form, clinical metrics associated with the receiver-operating characteristics displayed in FIG. 22.

FIG. 24 shows patient characteristics in an example study.

FIG. 25 shows abnormal cohort characteristics in an example study.

FIG. 28 shows a correlation coefficient table for an abnormal cohort.

DETAILED DESCRIPTION OF THE EMBODIMENTS

Figure 1:
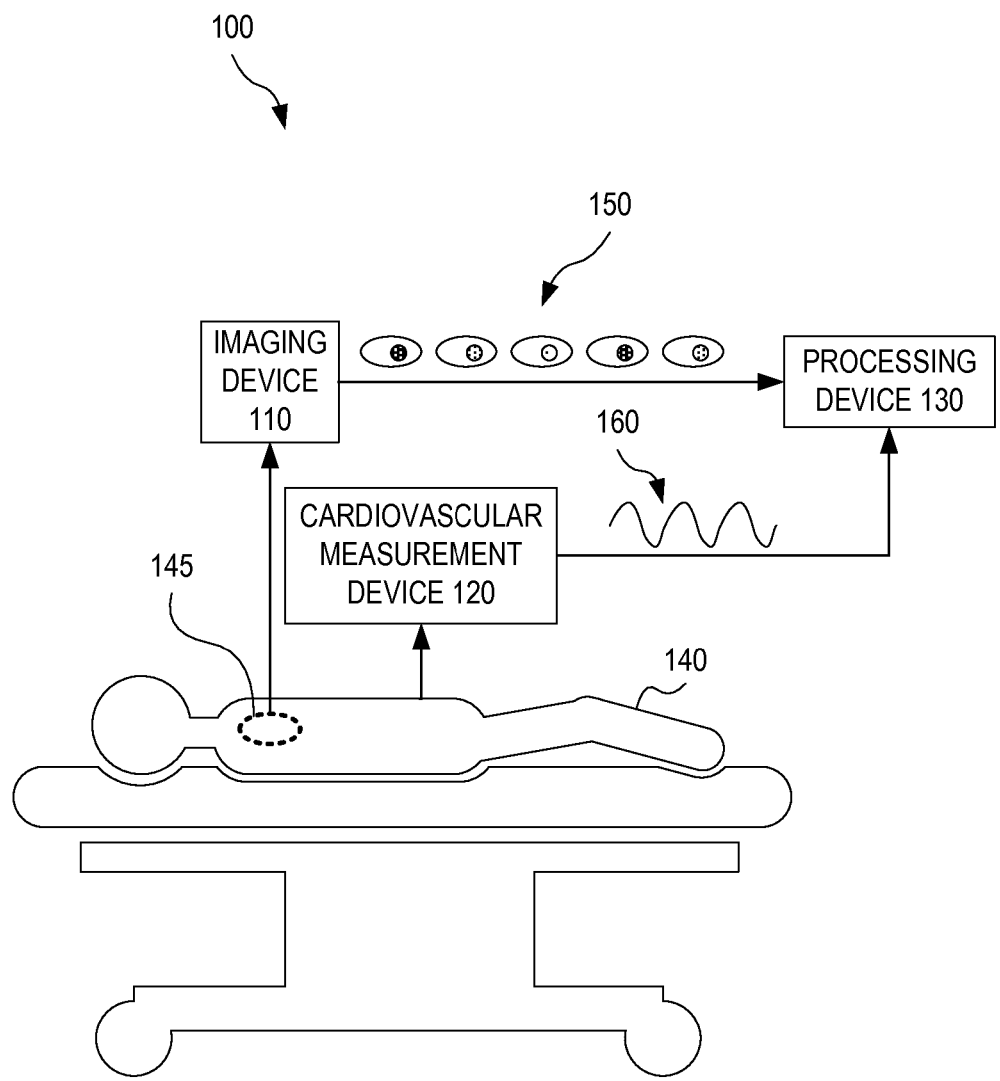
FIG. 1 illustrates a system for cardiovascular-dynamics correlated imaging, according to an embodiment.

FIG. 1 illustrates one exemplary system 100 for cardiovascular-dynamics correlated imaging of an area of interest 145 of a patient 140. System 100 includes an imaging device 110, a cardiovascular measurement device 120, and a processing device 130. Imaging device 110 images area of interest 145 to generate a time series of image data 150 thereof. Time series of image data 150 may be a time series of images or a time series of non-image data from which a time series of images may be reconstructed. For the purpose of the present disclosure "image" refers to a spatial map of a property, which may be in any representation known in the art including graphical representation and tabular form. Also for the purpose of the present disclosure, "time series" refers to a sequence of data measured at subsequent points in time, wherein the time points may be uniformly or non-uniformly spaced from each other in time. Cardiovascular measurement device 120 records at least one signal that reflects cardiovascular dynamics of patient 140. Cardiovascular measurement device 120 thus produces a time series of cardiovascular data 160.

Imaging device 110 and cardiovascular measurement device 120 respectively captures time series of image data 150 and records time series of cardiovascular data 160 concurrently. Hence, cardiovascular dynamics apparent in time series of cardiovascular data 160 may be correlated with temporal variations in time series of image data 150. Time series of image data 150 and time series of cardiovascular data 160 may be recorded at identical series of times or at different series of times having temporal overlap. In an example, time series of image data 150 is captured at a series of times that is substantially defined by the maximum rate at which image data may be captured by imaging device 110, while time series of cardiovascular data 160 is recorded at a series of times that is substantially defined by the maximum rate at which cardiovascular data may be captured by cardiovascular measurement device 120. In one embodiment, the maximum rate of cardiovascular measurement device 120 exceeds the maximum rate of imaging device 110 such that time series of cardiovascular data 160 has higher temporal resolution than time series of image data 150. In another embodiment, the maximum rate of imaging device 110 exceeds the maximum rate of cardiovascular measurement device 120 such that time series of image data 150 has higher temporal resolution than time series of cardiovascular data 160.

Imaging device 110 and cardiovascular measurement device 120 are communicatively coupled with processing device 130 and communicate time series of image data 150 and time series of cardiovascular data 160, respectively, to processing device 130.

Processing device 130 processes time series of image data 150 and time series of cardiovascular data 160 to evaluate correlation between time series of image data 150 and time series of cardiovascular data 160. In an embodiment, processing device 130 identifies heartbeat cycles from time series of cardiovascular data 160 and evaluates correlation between time series of image data 150 and the heartbeat cycles. Through such correlation evaluation, system 100 provides enhanced imaging of vascularized tissue within area of interest 145. Notably, system 100 achieves this without use of a contrast agent. Instead, vascularized tissue is "highlighted" by correlation of images with measurements of cardiovascular dynamics. Based upon the degree and/or nature of correlation between time series of image data 150 and time series of cardiovascular data 160, processing device 130 may detect the presence of vascularized tissue and provide an image thereof. Processing device 130 may distinguish between different types of vascularized tissue. For example, malignant tumors may exhibit weaker or stronger correlation with cardiovascular dynamics than healthy vascularized tissue. Therefore, processing device 130 may distinguish between a malignant tumor and healthy vascularized tissue or a benign tumor.

In some use scenarios, results generated by processing device 130 provide the basis for patient diagnosis. In one exemplary use scenario, area of interest 145 is an area with a tumor. By virtue of the correlation evaluation performed by processing device 130, system 100 determines if the tumor is malignant or benign. In another exemplary use scenario, area of interest 145 is an area with a malignant tumor. System 100 is employed to monitor disease status, i.e., status of the malignant tumor, for example during treatment with anti-angiogenic drugs.

Imaging device 110 may be any imaging modality that is sensitive to vascularization. In an embodiment, imaging device 110 is an electrical impedance tomography (EIT) device. In this embodiment, time series of image data 150 is a time series of spatial maps of one or more electrical impedance related parameters (such as impedance, conductivity, permittivity, resistivity, admittance, and/or associated spectral parameters) of area of interest 145, or a time series of image data from which a time series of spatial maps of the electrical impedance or conductivity of area of interest 145 may be reconstructed. The electrical conductivity of blood is generally around 0.6 Siemens/meter (S/m), while the electrical conductivity of other soft tissue generally is in the range between 0.1 S/m and 0.2 S/m. Hence, the electrical conductivity contrast between blood and other soft tissue is about 3:1. Accordingly, EIT is sensitive to vascularization.

In fact, EIT is more sensitive to vascularization, in terms of contrast between vascularized and non-vascularized tissue, than other common imaging modalities such as magnetic resonance imaging (MRI), computed tomography (CT), positron emission tomography (PET), and ultrasound imaging. Furthermore, EIT devices may image at high speed such that time series of image data 150 captures fast vascular dynamics at higher accuracy than slower imaging modalities. In addition, EIT is non-invasive and cheaper than most other imaging modalities. In other embodiments, imaging device 110 is an MRI device, a CT device, a PET device, an ultrasonography device, a video endoscope, or a fluoroscope.

Cardiovascular measurement device 120 is, for example, a pulse-oximeter (i.e., a device for measuring blood-oxygen saturation), an electrocardiograph, a sphygmomanometer, a blood flow measurement device, or another device capable of producing time series of cardiovascular data 160 at a rate sufficient to capture cardiovascular dynamics. For example, cardiovascular measurement device 120 has sensitivity and speed such that time series of cardiovascular data 160 includes a signature of heartbeat cycles.

Cardiovascular measurement device 120 need not be connected to area of interest 145, and time series of cardiovascular data 160 need not be representative of cardiovascular dynamics specific to area of interest 145. It is sufficient that cardiovascular measurement device 120 measures cardiovascular dynamics at some location of patient 140. In an embodiment, cardiovascular measurement device 120 records time series of cardiovascular data 160 at a location different from area of interest 145. The distance from area of interest 145 to the location where cardiovascular measurement device 120 connects to patient 140 may result in a phase shift between time series of image data 150 and time series of cardiovascular data 160. In an example, area of interest 145 is a breast of patient 140, while cardiovascular measurement device 120 is a pulse-oximeter connected to a finger of patient 140.

Processing device 130 may evaluate correlation between time series of image data 150 and time series of cardiovascular data 160 in real-time or at any time after receiving time series of image data 150 and time series of cardiovascular data 160. Without departing from the scope hereof, certain embodiments of system 100 do not include imaging device 110 and/or cardiovascular measurement device 120. In such embodiments, processing device 130 receives time series of image data 150 and/or time series of cardiovascular data 160 from devices external to system 100.

Figure 2:
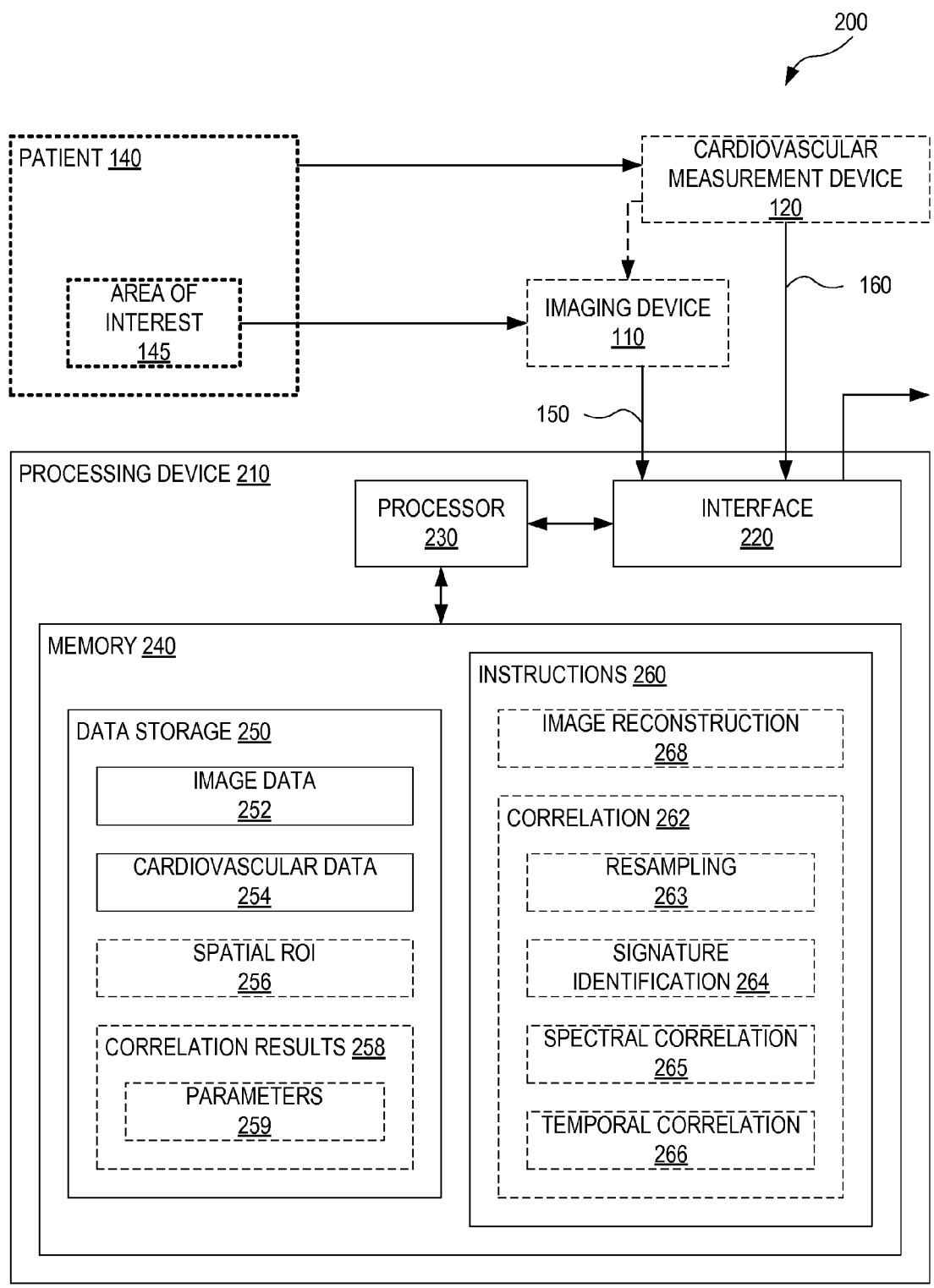
FIG. 2 illustrates another system for cardiovascular-dynamics correlated imaging, according to an embodiment.

FIG. 2 illustrates one exemplary system 200 for cardiovascular-dynamics correlated imaging. System 200 is an embodiment of system 100 (FIG. 1). System 200 includes a processing device 210 which is an embodiment of processing device 130 (FIG. 1). Processing device 210 processes time series of image data 150 (FIG. 1), associated with area of interest 145 (FIG. 1), and time series of cardiovascular data 160 (FIG. 1), associated with patient 140 (FIG. 1), to evaluate correlation between time series of image data 150 and time series of cardiovascular data 160. In an embodiment, system 200 includes imaging device 110 (FIG. 1) for generating time series of image data 150, and/or cardiovascular measurement device 120 (FIG. 1) for recording time series of cardiovascular data 160.

Processing device 210 includes an interface 220, a processor 230, and a memory 240. Processor 230 is communicatively coupled with interface 220 and memory 240. Memory 240 includes a data storage 250, and machine-readable instructions 260 encoded in a non-volatile portion of memory 240. Data storage 250 includes image data storage 252 and cardiovascular data storage 254. Processing device 210 receives time series of image data 150 and time series of cardiovascular data 160 through interface 220. Processor 230 stores time series of image data 150 and time series of cardiovascular data 160 to image data storage 252 and cardiovascular data storage 254, respectively. Processor 230 processes time series of image data 150 and time series of cardiovascular data 160 according to instructions 260. Processor 230 thus evaluates correlation between time series of image data 150 and time series of cardiovascular data 160. Processor 230 may also perform other processing of time series of image data 150 and time series of cardiovascular data 160 using instructions 260. Processing device 210 may output results of processing by processor 230, such as a correlation evaluation, through interface 220.

Optionally, data storage 250 further includes correlation results storage 258 with optional parameter storage 259. Processor 230 may store results of a correlation evaluation of time series of image data 150 and time series of cardiovascular data 160 to correlation results storage 258. Processor 230 may store correlation parameters, such as correlation coefficients and spectral power ratios to parameter storage 259. A spectral power ratio is a ratio of power in one spectral range to power in another spectral range, wherein the two spectral ranges may be partially overlapping or non-overlapping. Data storage 250 may further include spatial region of interest (ROI) definitions 256. Spatial ROI definitions 256 defines one or more spatial ROIs of time series of image data 150, which are considered by processor 230 when evaluating correlation between time series of image data 150 and time series of cardiovascular data 160. In some embodiments, spatial ROI definitions 256 is a fixed property of processing device 210, in which case spatial ROI definitions 256 may be located in instructions 260, without departing from the scope hereof.

In an embodiment, instructions 260 includes correlation instructions 262 that has instructions that, upon execution by processor 230, evaluates correlation between time series of image data 150 and time series of cardiovascular data 160. Correlation instructions 262 may include one or more of resampling instructions 263, signature identification instructions 264, spectral correlation instructions 265, and temporal correlation instructions 266. Processor 230 may utilize one or more of these instructions to evaluate correlation between time series of image data 150 and time series of cardiovascular data 160. Optionally, instructions 260 further include image reconstruction instructions 268. Processor 230 may, according to image reconstruction instructions 268, process embodiments of time series of image data 150 that are in non-image form to reconstruct a time series of images. For example, processor 230 reconstructs electrical conductivity images from voltages or currents measured by an EIT device according to image reconstruction instructions 268.

In certain embodiments, cardiovascular measurement device 120 is communicatively coupled with imaging device 110 such that cardiovascular measurement device 120 may control aspects of the operation of imaging device 110. For example, capture of image or image data of area of interest 145 by imaging device 110 is gated according to vascular dynamics recorded by cardiovascular measurement device 120. Although not illustrated in FIG. 2, such gating may be based upon the detection of cardiovascular signatures in time series of cardiovascular data 160 by processing device 210. Thus, cardiovascular measurement device 120 may be communicatively coupled with imaging device 110 through processing device 210, without departing from the scope hereof.

Figure 3:
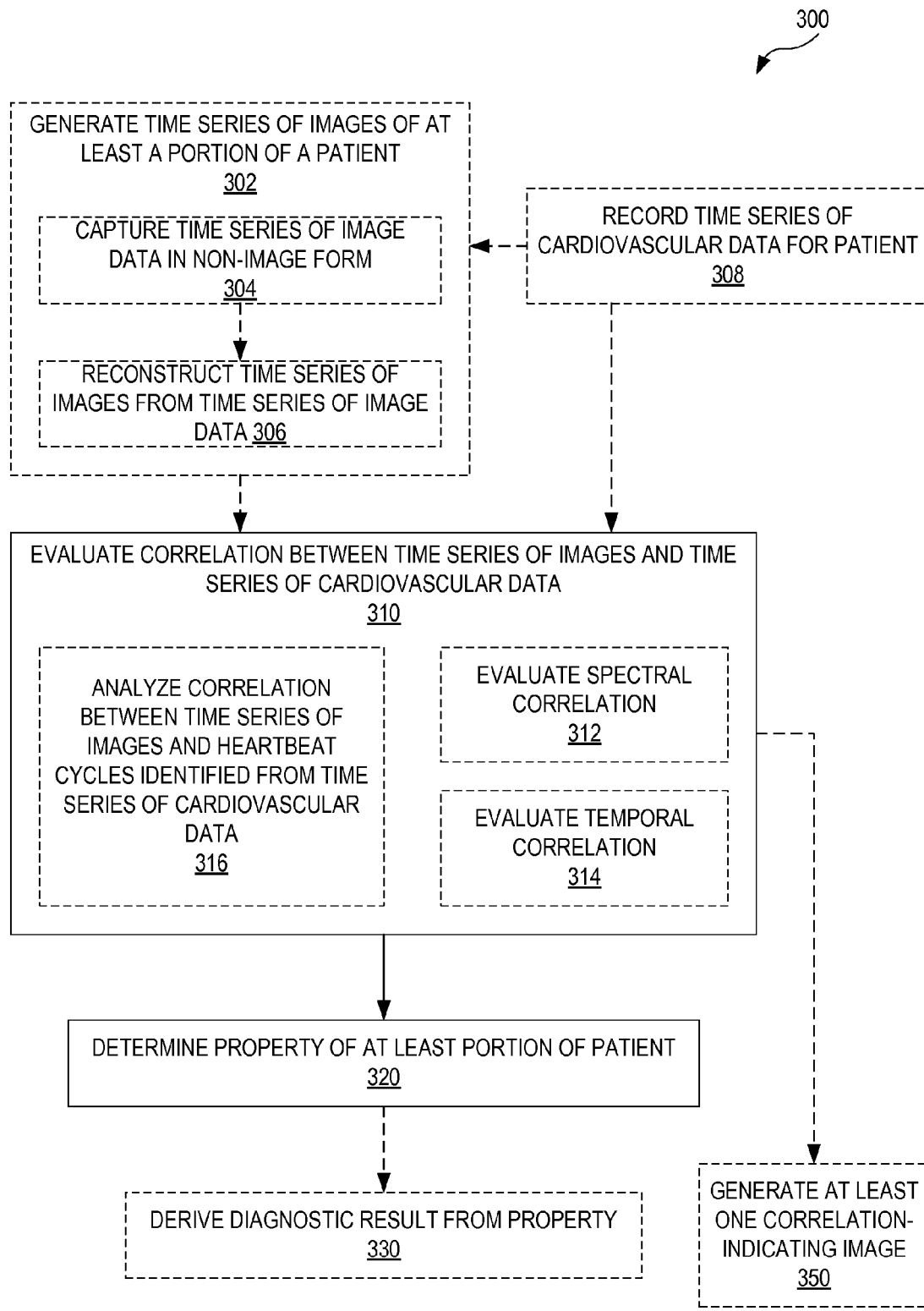
FIG. 3 illustrates a method for cardiovascular-dynamics correlated imaging, according to an embodiment.

FIG. 3 illustrates one exemplary method 300 for cardiovascular-dynamics correlated imaging. Method 300 is performed by, for example, system 100 (FIG. 1) or system 200 (FIG. 2). A step 310 receives a time series of images of at least a portion of a patient, such as area of interest 145 of patient 140 (FIG. 1), and a time series of cardiovascular data of the patient. The time series of images, or an underlying time series of image data, has been captured concurrently with the recording of the time series of cardiovascular data. The time series of images, or an underlying time series of image data, and the time series of cardiovascular data may be recorded at identical series of times or at different series of times having temporal overlap. Step 310 evaluates correlation between the time series of images and the time series of cardiovascular data. In an example, processor 230 (FIG. 2) retrieves time series of image data 150 (FIGS. 1 and 2), in image form, from image data storage 252 (FIG. 2) and time series of cardiovascular data 160 (FIGS. 1 and 2) from cardiovascular data storage 254 (FIG. 2), Processor 230 executes correlation instructions 262 (FIG. 2) to evaluate correlation between time series of image data 150 and time series of cardiovascular data 160. In an embodiment, one or more smaller spatial ROIs within the time series of images are separately considered by step 310. For example, processor 230 further retrieves spatial ROI definitions from spatial ROI definitions 256 (FIG. 2), and evaluates correlation within each of the one or more spatial ROIs according to correlation instructions 262.

Optionally, step 310 includes one or both of steps 312 and 314. In step 312, spectral correlation between the time series of images and the time series of cardiovascular measurements is evaluated. For example, processor 230 executes spectral correlation instructions 265 (FIG. 2) to evaluate spectral correlation between time series of image data 150 and time series of cardiovascular data 160, i.e. correlation between spectral properties of time series of image data 150 and spectral properties of time series of cardiovascular data 160. Processor 230 stores results of the correlation evaluation to correlation results storage 258 and/or outputs the results to a user or an external system through interface 220 (FIG. 2). In step 314, temporal correlation between the time series of images and the time series of cardiovascular measurements is evaluated. For example, processor 230 executes temporal correlation instructions 266 (FIG. 2) to evaluate temporal correlation between time series of image data 150 and time series of cardiovascular data 160.

In an embodiment, step 310 includes a step 316 of evaluating correlation between the time series of images and heartbeat cycles identified from the time series of cardiovascular data. In an example, processor 230 executes signature identification instructions 264 (FIG. 2) on time series of cardiovascular data 160 to identify at least one heartbeat cycle. Processor 230 then executes at least a portion of correlation instructions 262 to evaluate correlation between time series of image data 150 and the heartbeat cycle(s).

Steps 312, 314, and 316 may be applied to one or more different spatial ROIs within the area of interest of the patient, without departing from the scope hereof.

In a step 320, a property of the at least a portion of the patient, represented by the time series of images, is determined from the results of the correlation evaluation performed in step 310. In one example, a high (or low) degree of correlation, between the time series of images and the time series of cardiovascular data, found in step 310 leads to the identification of healthy vascularized tissue in the at least a portion of the patient represented by the time series of images. In another example, a low (or high) degree of correlation, between the time series of images and the time series of cardiovascular data, found in step 310 leads to the identification of a vascularized cancer tissue in the at least a portion of the patient represented by the time series of images. In yet another example, the degree of correlation and/or nature of correlation, between the time series of images and the time series of cardiovascular data, found in step 310 leads to a determination of the amount or type of vascularized tissue in the at least a portion of the patient represented by the time series of images. Step 320 may be performed separately for different spatial ROIs within the at least a portion of the patient represented by the time series of images, without departing from the scope hereof. In an embodiment, step 320 determines several properties of the at least a portion of the patient represented by the time series of images.

Step 320 may be performed by processing device 210, another system external to system 200, or by an operator or a physician. In one example, processor 230 retrieves correlation results from correlation results storage 258 and executes instructions 260 to derive a property of area of interest 145 from the correlation results. In another example, the property of area of interest 145 is determined externally to system 200 based upon the correlation results determined in step 310.

In an optional step 330, a diagnostic result is derived from the property or properties of the at least a portion of the patient, which are determined in step 320. Exemplary diagnostic results include presence of benign tumor, presence of malignant tumor, absence of malignant tumor, and degree of vascularization of malignant tumor.

Optionally, method 300 includes a step 350 of generating at least one correlation-indicating image. The at least one correlation-indicating image is, for example, a spatial map of a parameter that indicates degree of correlation between the time series of images and the time series of cardiovascular data. Exemplary parameters are discussed below in connection with FIGS. 5 and 6. The at least one correlation-indicating image may be a time series of correlation-indicating images showing the time series of images processed in step 310 with an overlay that indicates the degree of correlation between the time series of images and the time series of cardiovascular data.

In an embodiment, method 300 includes a step 302 of generating the time series of images. For example, imaging device 110 (FIGS. 1 and 2) generates the time series of images. In one embodiment of step 302, the imaging device directly captures the time series of images of at least a portion of the patient. In another embodiment, step 302 includes steps 304 and 306. In step 304, the imaging device captures a time series of image data that is in non-image form. In step 306, a time series of images is reconstructed from the time series of image data. For example, imaging device 110 captures a time series of image data that is not in image form, such as EIT voltages. Imaging device 110 communicates the time series of image data to processing device 210. Processor 230 receives the time series of image data from interface 220 and reconstructs, according to image reconstruction instructions 268 the time series of images from the time series of image data. Although not illustrated in FIG. 3, steps 306 may be initiated before completing step 304, without departing from the scope hereof. For example, step 306 is engaged to reconstruct each single image upon completion of the associated image data capture measurement. Thus, steps 304 and 306 may be performed alternatingly to reconstruct one image at a time, or concurrently at least in part.

In an embodiment, method 300 includes a step 308 of recording the time series of cardiovascular data. For example, cardiovascular measurement device 120 (FIGS. 1 and 2) records the time series of cardiovascular data. In embodiments of method 300 based upon capture of a time series of image data in non-image form, step 308 is performed concurrently with step 304. In embodiments of method 300, wherein step 302 is based upon direct capture of a time series of images, step 308 is performed concurrently with step 302.

Optionally, the performance of step 302 is gated according by step 308 such that the images, or image data, are captured at specific temporal points relative to the timing of heartbeat cycles. This may be beneficial when using imaging modalities operating at rates too slow to adequately capture cardiovascular dynamics, in which case temporal accuracy may instead be achieved through gating.

Figure 4:
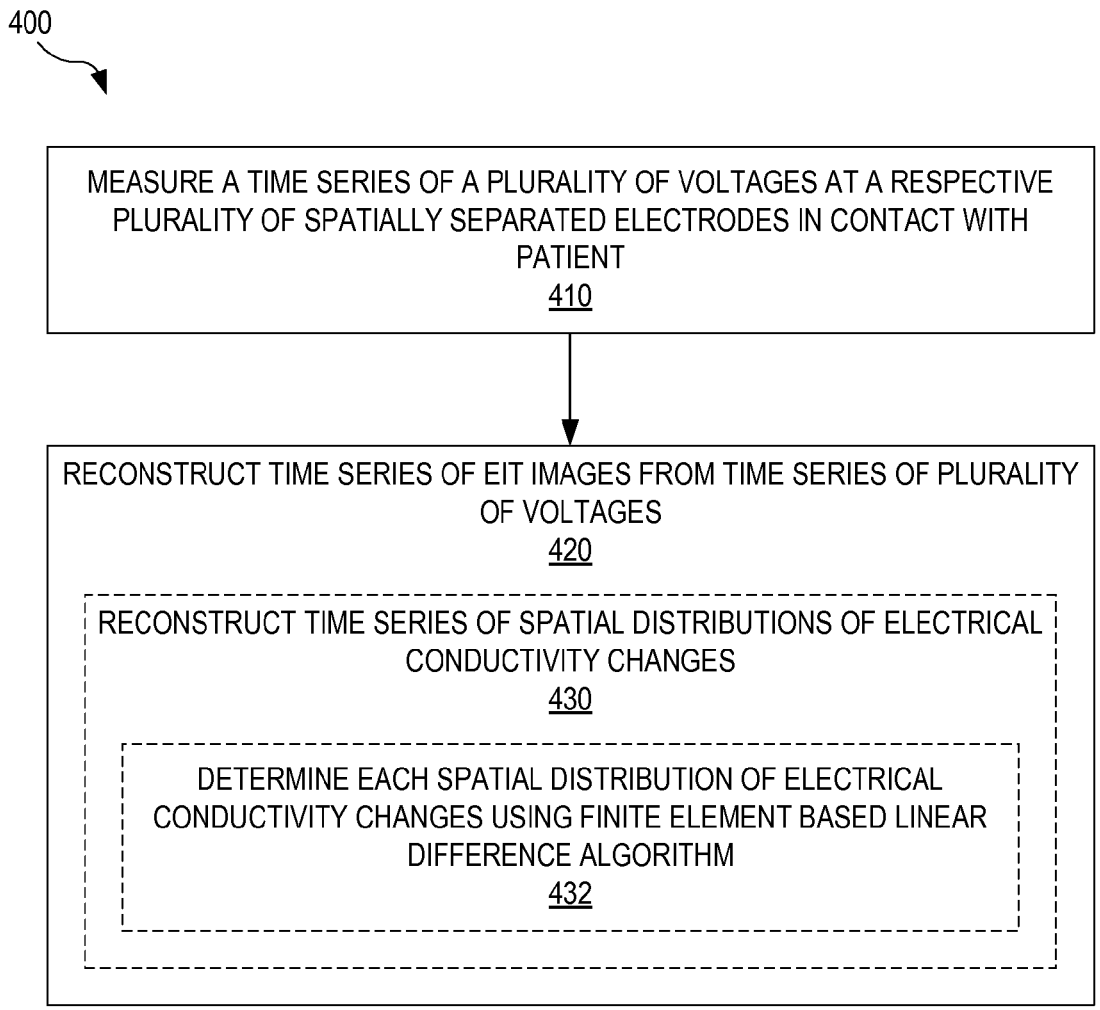
FIG. 4 illustrates a method for reconstructing a time series of electrical impedance tomography images, according to an embodiment.

FIG. 4 illustrates one exemplary method 400 for generating a time series of EIT images of at least a portion of a patient. Method 400 is an embodiment of step 302 of method 300 (FIG. 3). Method 400 includes a step 410 of measuring a time series of a plurality of voltages at a respective plurality of spatially separated electrodes in contact with a patient. This time series of voltages is an embodiment of time series of image data 150 (FIGS. 1 and 2). In one embodiment, the voltages are measured in a single-frequency EIT measurement, wherein a single-frequency alternating current or voltage is applied to one or more spatially separated electrodes connected to the patient. In another embodiment, the voltages are measured in a multi-frequency EIT measurement, wherein two or more time series single-frequency EIT measurements, at two or more different respective frequencies, are measured in an interlaced fashion or simultaneously using composite signals that include several different frequencies. Multi-frequency EIT based upon processing of composite signals including several different frequencies may operate at a higher sample rate than multi-frequency systems based upon an interlaced approach. In an example of step 410, imaging device 110 (FIGS. 1 and 2) is an EIT device that measures a time series of a plurality of voltages at a respective plurality of spatially separated electrodes in contact with patient 140 (FIGS. 1 and 2) near area of interest 145 (FIGS. 1 and 2). The EIT device may apply a single frequency to the electrodes to perform a single-frequency EIT measurement, or apply multiple different frequencies to the electrodes to perform a multi-frequency EIT measurement. Imaging device 110 communicates the time series of voltages, single-frequency or multi-frequency, to interface 220 of processing device 210 (FIG. 2). Processor 230 may store the time series of voltages to image data storage 252 (FIG. 2). Step 410 is an embodiment of step 304 (FIG. 3).

In a step 420, a time series of EIT images is reconstructed from the time series of voltages measured in step 410. In embodiments utilizing multi-frequency EIT, step 420 considers each frequency separately. In the following, step 420 is discussed for a single frequency. In an example of step 420, processor 230 retrieves the time series of voltages, measured in step 410, from image data storage 252. Processor 230 utilizes image reconstruction instructions 268 to reconstruct an EIT image from each time point of the series of voltages. Thereby, processor 230 reconstructs a time series of EIT images from the time series of voltages. Step 420 is an embodiment of step 306 (FIG. 3). Image reconstruction in step 420 may utilize a finite element based linear difference algorithm, a boundary element method, back projection, or other methods known in the art.

The EIT images reconstructed in step 420 provide a representation of a spatial impedance map of at least a portion of the patient as a function of time. The spatial impedance map is represented, for example, in terms of electrical conductivity, resistance, or impedance. In certain embodiments, step 420 includes a step 430, wherein the time series of EIT images is reconstructed as a time series of spatial distributions of electrical conductivity changes, as compared to a reference electrical conductivity distribution. The reference electrical conductivity distribution may be measured by the EIT device used to perform step 410, or derived from the time series of voltages measured in step 410. In an example, processor 230 utilizes image reconstruction instructions 268 to derive a reference electrical conductivity distribution from the time series of voltages measured in step 410 and further reconstruct a time series of spatial distributions of electrical conductivity changes relative to the reference electrical conductivity distribution.

Although not illustrated in FIG. 4, step 420 may be initiated before completing step 410, without departing from the scope hereof. For example, step 420 is engaged to reconstruct each single EIT image upon completion of the associated voltage measurement. Thus, steps 410 and 420 may be performed alternatingly to reconstruct one EIT image at a time, or concurrently at least in part.

Figure 5:
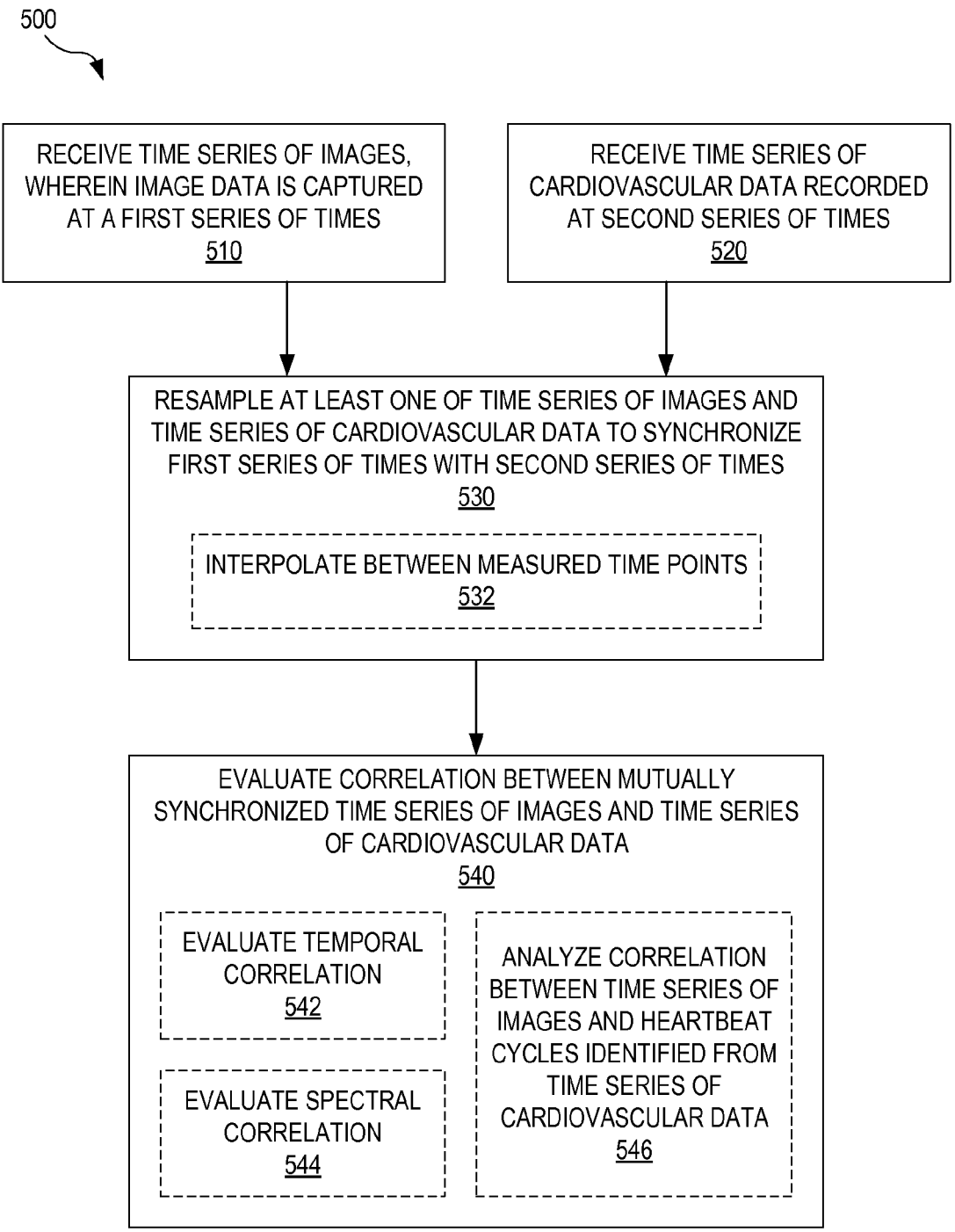
FIG. 5 illustrates a method for evaluating correlation between a time series of images and a time series of cardiovascular data, wherein the time series of images and the time series of cardiovascular data are recorded at different series of time, according to an embodiment.

FIG. 5 illustrates one exemplary method 500 for evaluating correlation between a time series of images of at least a portion of a patient and a time series of cardiovascular data of the patient, wherein the time series of images and the time series of cardiovascular data are recorded at different series of time. Method 500 may be implemented in method 300 (FIG. 3) as at least a portion of step 310. In a step 510, method 500 receives a time series of images, wherein the images or underlying image data is captured at a first series of times. In an example of step 510, interface 220 of processing device 210 (FIG. 2) receives time series of image data 150 (FIGS. 1 and 2). If time series of image data 150 is not in image form, processor 230 reconstructs a time series of images from time series of image data 150 according to image reconstruction instructions 268 (FIG. 2). Processor 230 stores the time series of images to image data storage 252 (FIG. 2). In a step 520, method 500 receives a time series of cardiovascular data recorded at a second series of times different from the first series of times. For example, processor 230 receives time series of cardiovascular data 160 (FIGS. 1 and 2) from cardiovascular measurement device 120 (FIGS. 1 and 2) through interface 220 and stores time series of cardiovascular data 160 to cardiovascular data storage 254 (FIG. 2).

In a step 530, the time series of images and/or the time series of cardiovascular data are resampled to synchronize the first series of times with the second series of times. Herein, the first series of times and the second series of times are not necessarily constants. Rather, the first series of times and the second series of times refer to the series of times associated with the time series of images and the time series of cardiovascular data, respectively, at any point during processing. Hence, the first series of times and/or the second series of times are modified in step 530. In one embodiment, one of the time series of images and the time series of cardiovascular data is resampled to match the time series associated with the other one of the time series of images and the time series of cardiovascular data. For example, the lower-rate time series, such as the time series of images, is resampled to match the higher-rate time series, such as the time series of cardiovascular data. Step 530 may include a step 532 of interpolating between measured time points of at least one of time series of images and time series of cardiovascular data. In an example of step 530, processor 230 retrieves the time series of images from image data storage 252 and resamples the time series of images according to resampling instructions 263 (FIG. 2) to synchronize the time series of images with time series of cardiovascular data 160.

A step 540 evaluates correlation between the mutually synchronized time series of images and time series of cardiovascular data received from step 530. Since step 540 considers mutually synchronized time series of images and time series of cardiovascular data, the correlation between the time series of images and the time series of cardiovascular data may be evaluated in a relatively simplistic fashion, such as through visual comparison. In an alternate example, the mutually synchronized time series of images and time series of cardiovascular data are processed mathematically to evaluate the degree and/or nature of correlation therebetween. For example, processor 230 evaluates correlation between the mutually synchronized time series of images and time series of cardiovascular data 160, according to correlation instructions 262 (FIG. 2), and stores the correlation results to correlation results storage 258 (FIG. 2) or outputs the correlation results via interface 220.

In an embodiment, step 540 includes one or both of steps 542 and 544. In step 544, the spectral correlation between the mutually synchronized time series of images and time series of cardiovascular data is evaluated. For example, processor 230 evaluates the spectral correlation between the mutually synchronized time series of images and time series of cardiovascular data according to spectral correlation instructions 265 (FIG. 2). Processor 230 stores the spectral correlation results to correlation results storage 258 or outputs the spectral correlation results via interface 220. In step 542, the temporal correlation between the mutually synchronized time series of images and time series of cardiovascular data is evaluated. For example, processor 230 evaluates the temporal correlation between the mutually synchronized time series of images and time series of cardiovascular data according to temporal correlation instructions 266 (FIG. 2). Processor 230 stores the temporal correlation results to correlation results storage 258 or outputs the temporal correlation results via interface 220.

Step 540 may further include a step 546 which is identical to step 316 of method 300 (FIG. 3).

Without departing from the scope hereof, steps 510 and 530 may be performed on a time series of image data in non-image form. In this case, reconstruction of the time series of image data to generate a time series of images may be performed after step 530.

Figure 6:
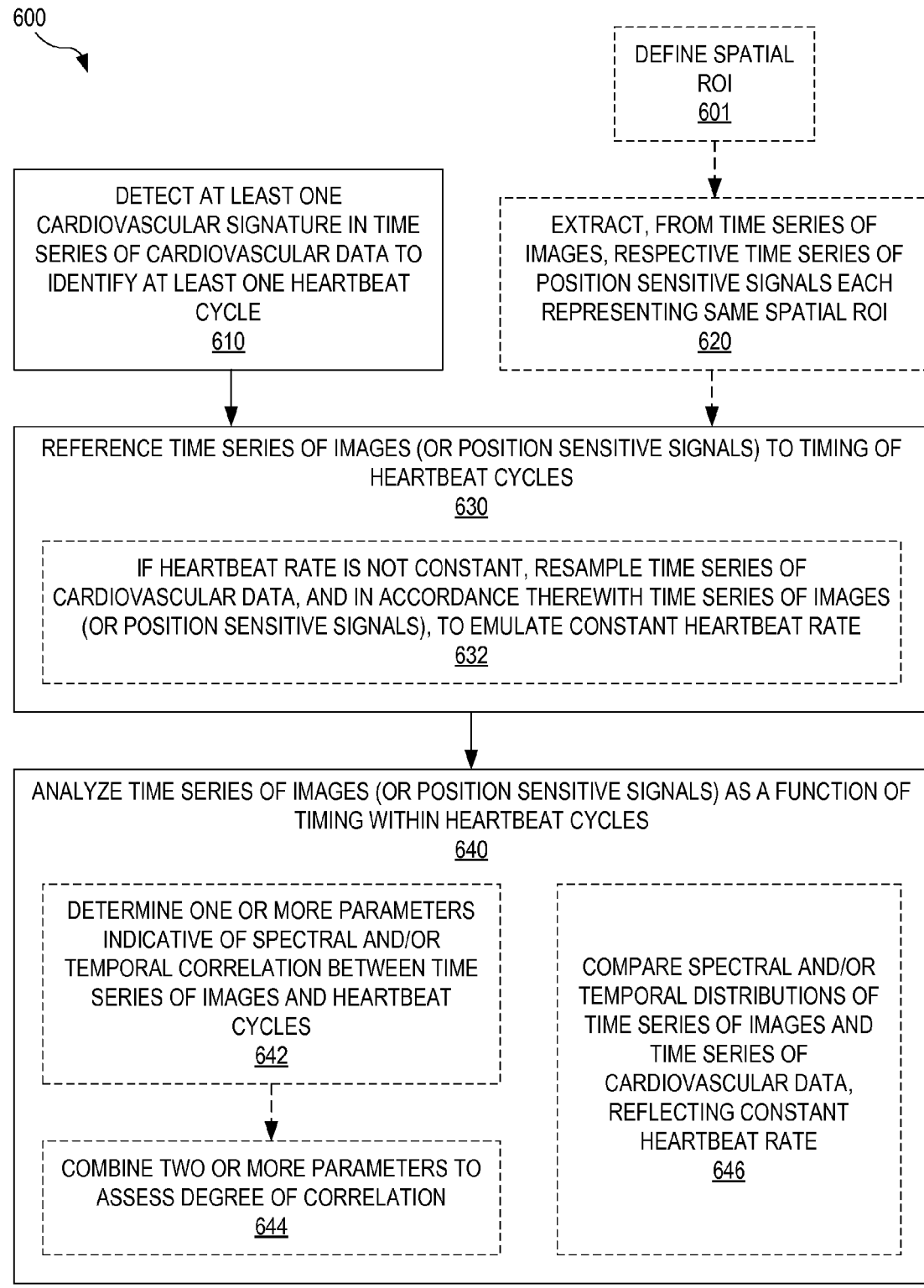
FIG. 6 illustrates a method for analyzing correlation between a time series of images and heartbeat cycles identified from a time series of cardiovascular data, according to an embodiment.

FIG. 6 illustrates one exemplary method 600 for analyzing correlation between a time series of images of at least a portion of a patient and heartbeat cycles identified from a time series of cardiovascular data of the patient. Method 600 is an embodiment of step 316 of method 300 (FIG. 3). In a step 610, at least one heartbeat cycle is identified in the time series of cardiovascular data through detection of at least one cardiovascular signature in the time series of cardiovascular data. For example, processor 230 (FIG. 2) processes time series of cardiovascular data 160 (FIGS. 1 and 2), according to signature identification instructions 264 (FIG. 2), to detect at least one cardiovascular signature such as a peak associated with each heartbeat cycle. Based upon the cardiovascular signature and according to signature identification instructions 264, processor 230 identifies at least one heartbeat cycle in time series of cardiovascular data 160.

In an optional step 620, a time series of position sensitive signals, each representing the same spatial ROI, is extracted from the time series of images. In an embodiment, each position sensitive signal in the time series of position sensitive signals is an average of the corresponding image within the spatial ROI. For example, processor 230 retrieves the time series of images from image data storage 252 (FIG. 2) and retrieves a spatial ROI definition from spatial ROI definitions 256 (FIG. 2). Processor 230 then extracts a time series of position sensitive signals from the time series of images according to the spatial ROI definition and correlation instructions 262 (FIG. 2). Optional step 620 may be preceded by a step 601 of defining the spatial ROI. In one embodiment, the spatial ROI is defined by an operator or by processing device 210 (FIG. 2) based upon images provided by the imaging device used to generate the time series of images or image data. In another embodiment, the spatial ROI is defined by an operator or by processing device 210 based upon images provided by another imaging device utilizing a different imaging modality. In yet another embodiment, the spatial ROI is predefined.

Without departing from the scope hereof, steps 620, 630, and 640, and optionally step 601, may be performed for several different spatial ROIs.

In a step 630, the time series of images (or position sensitive signals in embodiments of method 600 including optional step 620) is referenced to the timing of heartbeat cycles as identified in step 610. For example, processor 230 references the time series of images (or position sensitive signals) to timing of heartbeat cycles according to correlation instructions 262.

In an embodiment, and if the rate of heartbeats identified in step 610 is not constant, step 630 includes a step 632, wherein the time series of cardiovascular data is resampled to emulate a constant heartbeat rate. The time series of images (or position sensitive signals) is resampled accordingly such that the temporal relationship between the time series of cardiovascular data and the time series of images (or position sensitive signals) is not distorted by the performance of step 632. In an example of step 632, processor 230 resamples the time series of cardiovascular data and the time series of images (or position sensitive signals) according to resampling instructions 263 (FIG. 2).

In a step 640, the time series of images (or position sensitive signals) is analyzed as a function of timing within a heartbeat cycle. Step 640 includes step 646 and/or step 642. Step 642 determines one or more parameters indicative of spectral and/or temporal correlation between the time series of images (or position sensitive signals) and heartbeat cycles. Exemplary parameters include spectral correlation coefficient, temporal correlation coefficient (optionally corrected for a phase shift between the time series of images and the time series of cardiovascular data, for example based upon a premeasured value of the phase shift), maximum temporal correlation coefficient as a function of phase shift between the time series of images (or position sensitive signals) and heartbeat cycles, phase at which the maximum temporal correlation coefficient is attained, and spectral power ratios of the time series of images (or position sensitive signals). The spectral power ratios indicate the degree of spectral correlation between the time series of images (or position sensitive signals) and heartbeat cycles. In an example of step 642, processor 230 utilizes spectral correlation instructions 265 (FIG. 2) or temporal correlation instructions 266 (FIG. 2) to determine one or more parameters indicative of spectral and/or temporal correlation. Processor 230 may store such parameters to parameter storage 259 (FIG. 2).

Optionally, step 642 is succeeded by a step 644, in which two or more parameters determined in step 642 are combined to further evaluate the degree and/or nature of correlation between the time series of images (or position sensitive signals) and heartbeat cycles. Step 644 may evaluate a combination of parameters against correlation criteria. In an example of step 644, processor 230 retrieves two or more parameters from parameter storage 259 and combines these parameters according to correlation instructions 262.

In step 646, spectral and/or temporal distributions of time series of images (or position sensitive signals) are compared to those of the time series of cardiovascular data reflecting a constant heartbeat rate. For example, the time series of images (or position sensitive signals) and the time series of cardiovascular data received from step 630 are outputted to an operator or physician via interface 220 (FIG. 2). The physician or operator compares the spectral and/or temporal distributions of the time series of images (or position sensitive signals) and the time series of cardiovascular data reflecting constant heartbeat rate.

In an embodiment, method 600 takes as input mutually synchronized time series of cardiovascular data and time series of images, such as those generated by step 530 of method 500 (FIG. 5).

FIG. 7 illustrates one exemplary method 700 for evaluating temporal correlation between a time series of images of at least a portion of a patient and a time series of cardiovascular data of the patient. Method 700 may be implemented in method 300 (FIG. 3) as at least a portion of step 314, in method 500 (FIG. 5) as at least a portion of step 542, or in method 600 (FIG. 6) as at least a portion of step 642.

In a step 710, the temporal correlation coefficient between a time series of position sensitive signals and the time series of cardiovascular data is calculated as a function of phase shift between the time series of position sensitive signals and the time series of cardiovascular data. The time series of position sensitive signals may be derived from the time series of images as discussed in connection with step 620 (FIG. 6). The time series of images and the time series of cardiovascular data may be mutually synchronized as discussed in connection with step 530 (FIG. 5). Additionally, the time series of images and the time series of cardiovascular data may reflect a constant heartbeat rate, optionally after resampling as discussed in connection with step 632 (FIG. 6).

Since the time series of images and the time series of cardiovascular data may be obtained in two different locations of the patient, a phase shift may exist between the time series of images and the time series of cardiovascular data. Furthermore, the imaging device and cardiovascular measurement device used to generated the time series of images and the time series of cardiovascular data, respectively, may introduce additional phase shifts of unknown magnitude. If such phase shifts are not taken into account, for example by premeasuring the phase shift and correcting therefor, the calculated temporal correlation coefficient may be lower than the actual temporal correlation coefficient obtained when correcting for phase shift between the time series of images and the time series of cardiovascular data. Step 710 overcomes this issue by varying the phase shift between the time series of images and the time series of cardiovascular data and calculating the temporal correlation coefficient therebetween for a range of phase shifts, such as several different phase shifts substantially spanning the full range of phase shifts.

In an example of step 710, processor 230 (FIG. 2) retrieves the time series of position sensitive signals from image data storage 252 (FIG. 2) and the time series of cardiovascular data from cardiovascular data storage 254 (FIG. 2). Processor 230 utilizes temporal correlation instructions 266 to calculate the temporal phase shift between the time series of position sensitive signals and the time series of cardiovascular data as a function of phase shift therebetween. Processor 230 stores this temporal correlation coefficient as a function of phase shift to correlation results storage 258 (FIG. 2).

In a step 720, method 700 determines at least one of (a) the maximum temporal correlation coefficient as a function of phase shift and (b) the phase shift at which the maximum temporal correlation coefficient. For example, processor 230 retrieves the temporal correlation coefficient as a function of phase shift from correlation results storage 258 and determines, according to temporal correlation instructions 266, the maximum temporal correlation coefficient and/or the phase at which the maximum temporal correlation coefficient is attained.

FIG. 8 illustrates a method 800 for evaluating spectral correlation between a time series of images of at least a portion of a patient and a time series of cardiovascular data of the patient. Method 800 may be implemented in method 600 (FIG. 6) as at least a portion of step 642. In a step 810, the spectral distribution of a time series of position sensitive signals is evaluated. Optionally, step 810 includes determining the spectral distribution of the time series of position sensitive signals, for example using a fast Fourier transform. The time series of position sensitive signals is assumed to reflect a constant heartbeat rate and is, for example, generated in step 632 (FIG. 6). Since the time series of position sensitive signals correspond to a constant heartbeat rate, the spectral distribution of the time series of position sensitive signals indicates the degree and/or nature of spectral correlation between the time series of position sensitive signals and heartbeat cycles. In an embodiment, step 810 includes a step 812 of calculating one or more power ratios of the spectral distribution of the time series of position sensitive signals. A spectral power ratio is the ratio of power in one spectral range to the power in another spectral range. The two spectral ranges may be non-overlapping or partially overlapping.

In an example of steps 810 and 812, processor 230 (FIG. 2) utilizes spectral correlation instructions 265 (FIG. 2) to calculate the power spectrum of the time series of position sensitive signals, reflecting a constant heartbeat rate, and further calculate therefrom one or more spectral power ratios.

Figure 9:
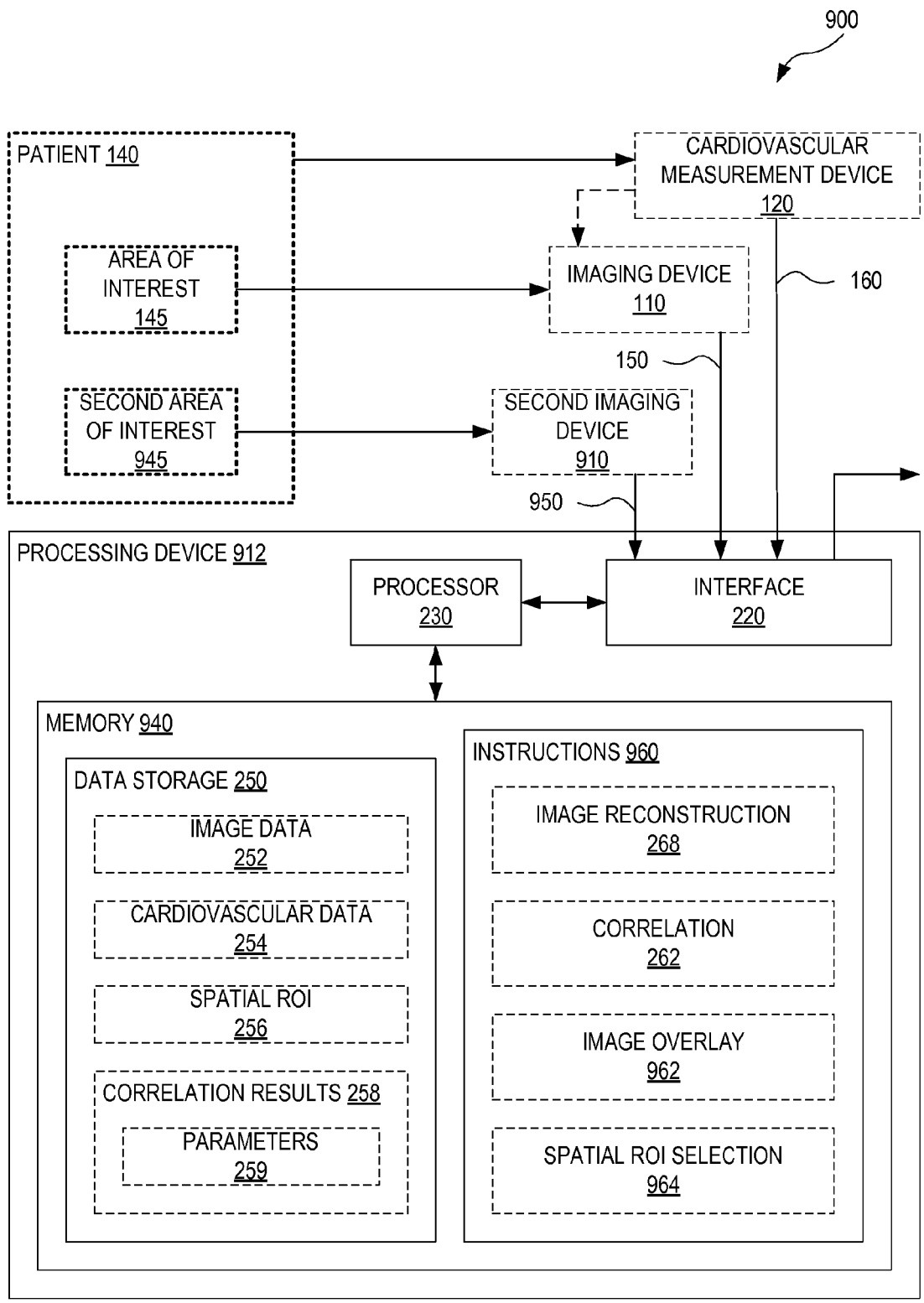
FIG. 9 illustrates a system for cardiovascular dynamics correlated imaging, which utilizes two different imaging devices, according to an embodiment.

FIG. 9 illustrates one exemplary system 900 for cardiovascular dynamics correlated imaging of area of interest 145 of patient 140 (FIGS. 1 and 2), which utilizes two different imaging devices. System 900 is similar to system 200 (FIG. 2). As compared to system 200, system 900 further includes a second imaging device 910 that generates images different from those of imaging device 110 (FIGS. 1 and 2). Additionally, processing device 210 (FIG. 2) is replaced with a processing device 912. Processing device 912 is similar to processing device 210 except for memory 240 (FIG. 2) being replaced with a memory 940. In turn, memory 940 is similar to memory 240 except for instructions 260 (FIG. 2) being replaced by instructions 960 which, as compared to instructions 260 may further include image overlay instructions 962 and or spatial ROI selection instructions 964.

Second imaging device 910 generates one or more second-type images 950 of a second area of interest 945 of patient 140. Second area of interest 945 has at least some overlap with area of interest 145 (FIGS. 1 and 2). Second-type images 950 are of type different from the images associated with time series of image data 150 (FIGS. 1 and 2). Second imaging device 910 communicates second-type image(s) 950 to interface 220 (FIG. 2) of processing device 912. In one embodiment, second imaging device 910 is of type different from imaging device 110. In another embodiment, second imaging device 910 is of same type as imaging device 110, but utilized to generate a different type of images. For example, second imaging device 910 is an MRI device generating anatomic MRI images, while imaging device 110 is an MRI device generating cardiovascular emphasized images.

In one embodiment, instructions 960 of processing device 912 includes image overlay instructions 962, that upon execution by processor 230 (FIG. 2) overlays one image or time series of images on another image or time series of images. For example, processor 230 may execute image overlay instructions 962 to overlay one or more correlation-indicating images, generated from time series of image data 150 and time series of cardiovascular data 160 (FIGS. 1 and 2) by performing method 300 (FIG. 3) with step 350, on second-type image(s) 950. Processor 230 may store such an overlaid image to image data storage 252 and/or communicate such an overlaid image to an external system or user via interface 220.

In another embodiment, instructions 960 includes spatial ROI selection instructions 964 that upon execution by processor 230 analyzes second-type image(s) 950 to determine one or more spatial ROIs to be considered by processing device 912 when evaluating correlation between time series of image data 150 and time series of cardiovascular data 160, for example as discussed in connection with method 600 (FIG. 6). Processor 230 may store such spatial ROIs to spatial ROI definitions 256 (FIG. 2), from where processor 230 may retrieve one or more spatial ROIs when performing method 600.

Second imaging device 910 is, for example, an EIT device, an MRI device, a CT device, and ultrasonograph, a video endoscope, or a fluoroscope. In certain embodiments of system 900, imaging device 110 is an EIT device and second imaging device 910 is a non-EIT device such as an MRI device, a CT device, and ultrasonograph, a video endoscope, or a fluoroscope. This embodiment benefits from correlation of time series of cardiovascular data 160 with time series of image data 150 generated by an imaging device that is very sensitive to cardiovascular dynamics, as discussed in connection with FIG. 1, which leads to high-quality cardiovascular-dynamics correlation information. System 900 is capable of combining such cardiovascular-dynamics correlation information with second-type image(s) 950 which may provide information about area of interest 145 not achievable using imaging device 110.

Figure 10:
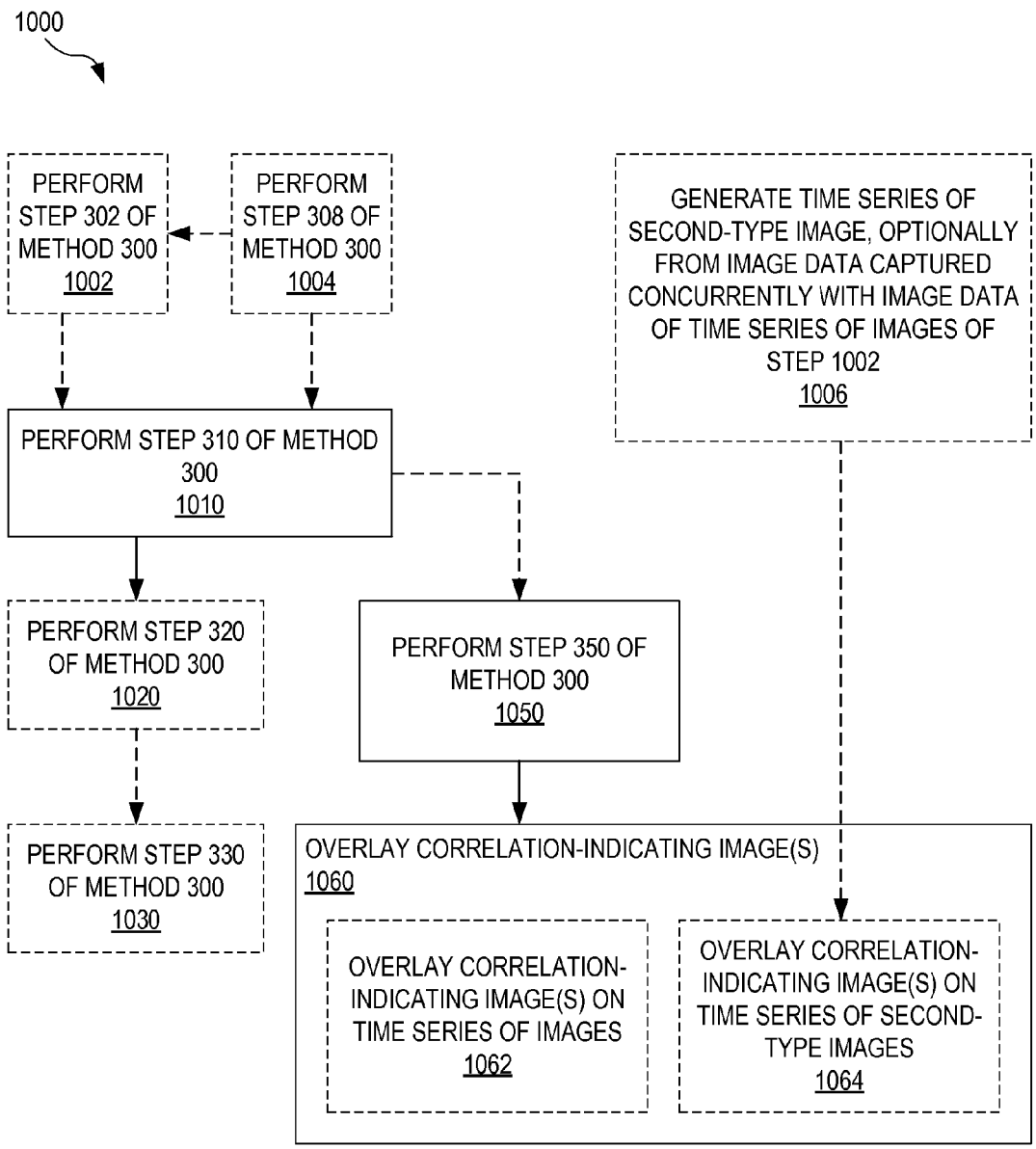
FIG. 10 illustrates a method for overlaying, on a time series of images, a correlation-indicating image, indicating correlation between a time series of images and a time series of cardiovascular data, according to an embodiment.

FIG. 10 illustrates one exemplary method 1000 for overlaying a correlation-indicating image, indicating correlation between a time series of images of at least a portion of a patient and a time series of cardiovascular data of the patient, on a time series of images. Method 1000 may be performed by system 900 of FIG. 9.

Method 1000 is similar to method 300 of FIG. 3 and includes steps 1010 and 1050, and optionally one or more of steps 1002, 1004, 1020, and 1030, wherein method 1000 performs respective steps 310 and 350 and optional steps 302, 308, 320, and 330 as discussed in connection with FIG. 3. Additionally, method 1000 includes a step 1060 wherein the correlation-indicating image(s) generated in step 1050 are overlaid on a time series of images.

In one embodiment, step 1060 includes a step 1062 of overlaying the correlation-indicating image on the time series of images processed in step 1010. For example, processor 230 of system 900 (FIG. 9) executes image overlay instructions 962 (FIG. 9) to overlay the correlation-indicating image on time series of image data 150 in image format (FIGS. 1 and 9).

In another embodiment, step 1060 includes a step 1064 of overlaying the correlation-indicating image on a time series of second-type images generated by an imaging device of type different from the one used to generated the time series of images processed in step 1010. For example, processor 230 of system 900 (FIG. 9) executes image overlay instructions 962 (FIG. 9) to overlay the correlation-indicating image on a time series of second-type images 950 (FIG. 9). In this embodiment, method 1000 may further include a step 1006 of generating the time series of second-type images. The time series of second-type images, or underlying second-type image data, may be captured concurrently with the time series of image data used to generate the time series of images processed in step 1010. For example, second imaging device 910 (FIG. 9) captures a time series of second-type images 950 (FIG. 9) concurrently with imaging device 110 (FIGS. 1 and 9) capturing time series of image data 150 (FIGS. 1 and 9).

Figure 11:
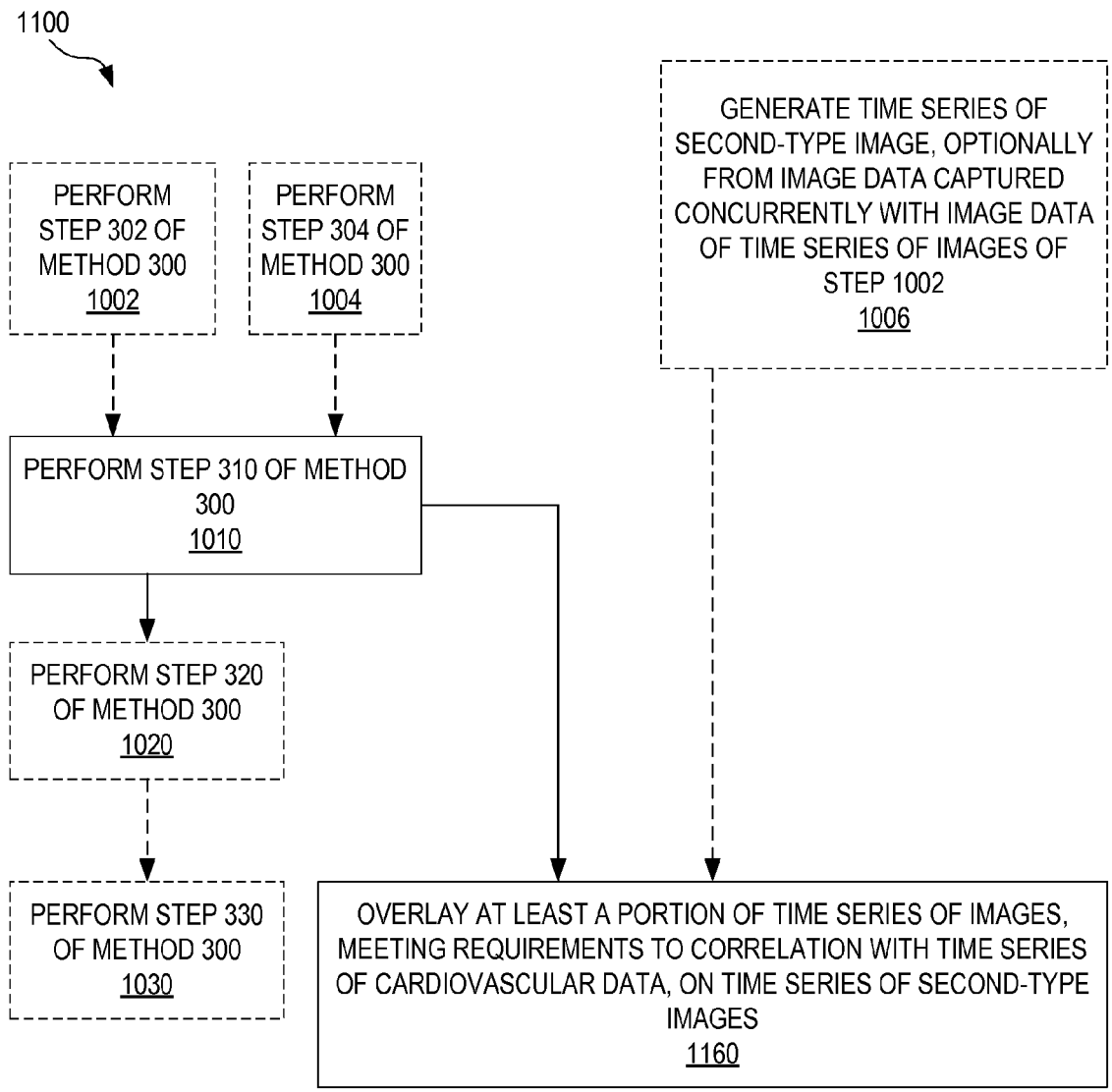
FIG. 11 illustrates a method for overlaying at least a portion of a time series of first-type images on a time series of second-type images, according to an embodiment.

FIG. 11 illustrates one exemplary method 1100 for overlaying at least a portion of a time series of first-type images of a first area of interest of a patient on a time series of second-type images of a second area of interest of the patient, wherein the first and second areas of interest at least partially overlap. The second-type images are of type different from the first-type images. Method 1100 may be performed by system 900 (FIG. 9). Method 1100 is similar to method 1000 (FIG. 10) except that step 1060 is replaced with a step 1160.

In step 1160, at least a spatial portion of the time series of images processed in step 1010, which meets specified requirements to the degree and/or nature of correlation with the time series of cardiovascular data, is overlaid on a time series of second-type images. For example, processor 230 (FIGS. 2 and 9) executes image overlay instructions 962 (FIG. 9) to overlay a spatial portion of time series of image data 150 (FIGS. 1 and 9), or a time series of images generated therefrom, which meets requirements to correlation with time series of correlation-indicating image on a time series of second-type images 950 (FIG. 9).

Example I: Real-Time Electrical Impedance Variations in Phantoms and in Women with and without Breast Cancer In this Example, an embodiment of system 100 (FIG. 1) performs cardiovascular-dynamics correlated imaging of (a) pulsating phantoms and (b) breasts of female patients according to an embodiment of method 300 (FIG. 3). In the embodiment of system 100 utilized in this Example, imaging device 110 is an EIT device and cardiovascular measurement device 120 is a pulse-oximeter.

Imaging Breast Tumor Hemodynamics

Neovasculature occurs primarily at a tumor's periphery while its center tends to undergo necrosis. The physiological phenomena occurring within the microvasculature surrounding the tumor is complex, and studies have shown this network of vessels to be chaotically arranged, permeable capillaries. Benign lesions are vascularized as well, but they are more well-defined and lack the chaotic structures of many malignant tumors.

As blood flows through the vasculature it experiences a periodic pulsatillity synchronized to the beating of the heart. The presence of the excessive chaotically arranged vasculature around a malignant tumor may present a different dynamic electrical impedance signature than that obtained from normal and benign tissues within the breast. A high-speed, precise EIT system may be capable of imaging this periodic blood flow by recording measurements at various phases within the cardiovascular cycle. Further, collecting data at specific phases within the cardiac cycle, but over multiple cycles, will provide a multiplicity of data that can be averaged to increase noise suppression and improve image contrast. This would provide a new contrast mechanism that is different from that available through static and multi-frequency EIT which may prove more successful at differentiating breast tissues based on the dynamic characteristics of their blood flow instead.

EIT Imaging and Image Synchronization

Dartmouth's third generation breast EIT system, an embodiment of imaging device 110 (FIG. 1), is capable of collecting high frame rate data, >40 frames per second (fps), as described previously in R. J. Halter, A. Hartov, K. D. Paulsen, "A broadband high frequency electrical impedance tomography system for breast imaging," IEEE Transactions on Biomedical Engineering, vol. 55, pp. 650-59, 2008 and in R. J. Halter, A. Hartov, K. D. Paulsen, "Video Rate Electrical Impedance Tomography of Vascular Changes: Preclinical Development," Physiological Measurement, vol. 29, no. 3, pp. 349-364, 2008, both of which are incorporated by reference herein in their entireties. Briefly, this EIT system is a wide-bandwidth (10 kHz-10 MHz), 64 electrode, voltage-driven system specifically designed for use in breast imaging. In high-speed acquisition mode it collects bursts of 40 frames of data at a user specified frame rate (up to 180 fps); following acquisition the data is off-loaded from the system electronics to an interface computer for post-processing and image reconstruction. The computer is an embodiment of processing device 130 (FIG. 1).

The system has been upgraded with a cardiovascular monitoring unit (CMU) to permit external triggering of data collection. Specifically, a USB-based analog signal capture device (PMD-1608FS, Measurement Computing, Massachusetts, USA) interfaced to the EIT system computer (an embodiment of processing device 130 (FIG. 1)) is used to record an external biophysical signal. The PMD-1608FS is coupled with a pulse-oximetry sensor to form an embodiment of cardiovascular measurement device 120 (FIG. 1). The PMD-1608FS has eight single-ended analog inputs that are captured and converted to the digital domain with 16-bit ADCs. The EIT system software continuously scans a single analog input channel at a rate of 62.5 Hz and a software-based threshold detection scheme is used to trigger EIT data acquisition. Thresholds are manually selected based on the characteristics of the input signal. This provides the ability to trigger EIT data acquisition synchronously with the QRS complex of an ECG waveform or the peak in the oxygen saturation signal sampled from a pulse-oximeter. The cardiovascular signal is recorded simultaneously while EIT data acquisition occurs. Following acquisition of a 40 frame burst of data, additional bursts of frames can be recorded. When an arbitrary number of bursts are collected, data acquisition is halted and the data is transferred for offline image reconstruction.

For the phantom experiments and patient series reported here, the system was configured to image a single plane, consisting of a circular ring of 16 electrodes. The 15 optimal trigonometric voltage patterns for a 16 electrode system, as defined in D. Isaacson, "Distinguishability of conductivities by electric current computed tomography," IEEE Trans. Med. Imaging, vol. 5, pp. 91-95, 1986 which is incorporated by reference herein in its entirety, were used as the driving patterns. Each acquisition frame consisted of 240 voltages measurements (15 patterns×16 electrodes) which were arranged in the column vector $V_i$. Each forty-frame burst of recorded voltages defined a non-square matrix, $V_n=[V_1\ V_2\ V_3\ \ldots\ V_{40}]$, where n represents the burst number when multiple bursts of image frames are collected. The corresponding biophysical signal sampled at 62.5 Hz defined a column vector $y_n=[y_1, y_2, y_3, \ldots Y_{Nc,samples}]$ for each 40-frame burst, where n=1, 2, 3, . . . $N_{burst}$, and $N_{c,samples}$, the length of $y_i$, is based on the duration of the 40-frame EIT burst collection window. This length is a function of the EIT frame rate and for the data presented here is fixed at 17.3 fps. The EIT data collection method described in this Example is an embodiment of step 410 (FIG. 4). The series of $V_n$ is an embodiment of time series of image data 150 (FIG. 1). The series of $y_n$ is an embodiment of time series of cardiovascular data 160 (FIG. 1).

Image Reconstruction

Image reconstruction is performed according to step 420 with steps 430 and 432 (FIG. 4). This Example used a finite element (FEM) based linear difference algorithm to estimate the changing conductivity distribution between frames. A 2D circular mesh with 640 elements, 353 nodes and scalable diameter was generated to model the experimental geometry. The change in conductivity, $\Delta\sigma_i$, at each of the mesh nodes is calculated from $\Delta\sigma_i=(J^TJ+\lambda L^TL)^{-1}\ J^T\{V^{ref}-V_i\}$, i ∈1, 2, 3, . . . , 40, (Eq. 1) where J is a Jacobian matrix representing the sensitivity of changes in boundary voltages to changes in conductivity, L is a Laplacian regularization matrix, and λ is a regularization parameter used to stabilize the inversion. $V^{ref}$ is a set of boundary voltages designated as a reference conductivity distribution, while $V_i$ is the set of boundary voltages collected during each frame i. J is computed from the reference boundary voltages via the adjoint method disclosed in N. Polydorides and W. R. B. Lionheart, "A Matlab toolkit for three dimensional electrical impedance tomography: a contribution to the electrical impedance and diffuse optical reconstruction software project," Meas. Sci. Technol., vol. 13, pp. 1871-1883, 2002 which is incorporated by reference herein in its entirety, and is fixed for each $\Delta\sigma_i$ calculation. The vector $\Delta\sigma_i$ represents the 353 nodal change in conductivity values at each frame i and is computed using the change in measured boundary voltages with respect to the reference. $V_{ref}$ is defined as the mean of all voltages recorded from a single burst of data, $$V^{ref} = \overline{V}_n = \frac{1}{N}\sum_1^{40} V_i.$$

Taking the mean across all frames provides a less noisy reference from which to calculate conductivity changes. $\Delta\sigma_i$ is calculated using Eq. 1 for each of the 40 frames recorded from a single acquisition burst. Empirical testing demonstrated that a λ of 0.001 provided a sufficient level of regularization to ensure stable inversion. Within each burst, $\Delta\sigma_n=[\Delta\sigma_1\ \Delta\sigma_2\ \Delta\sigma_3\ \ldots\ \Delta\sigma_{40}]$ represents the spatiotemporal sequence of changing conductivity estimates.

Correlation Evaluation

Figure 12:
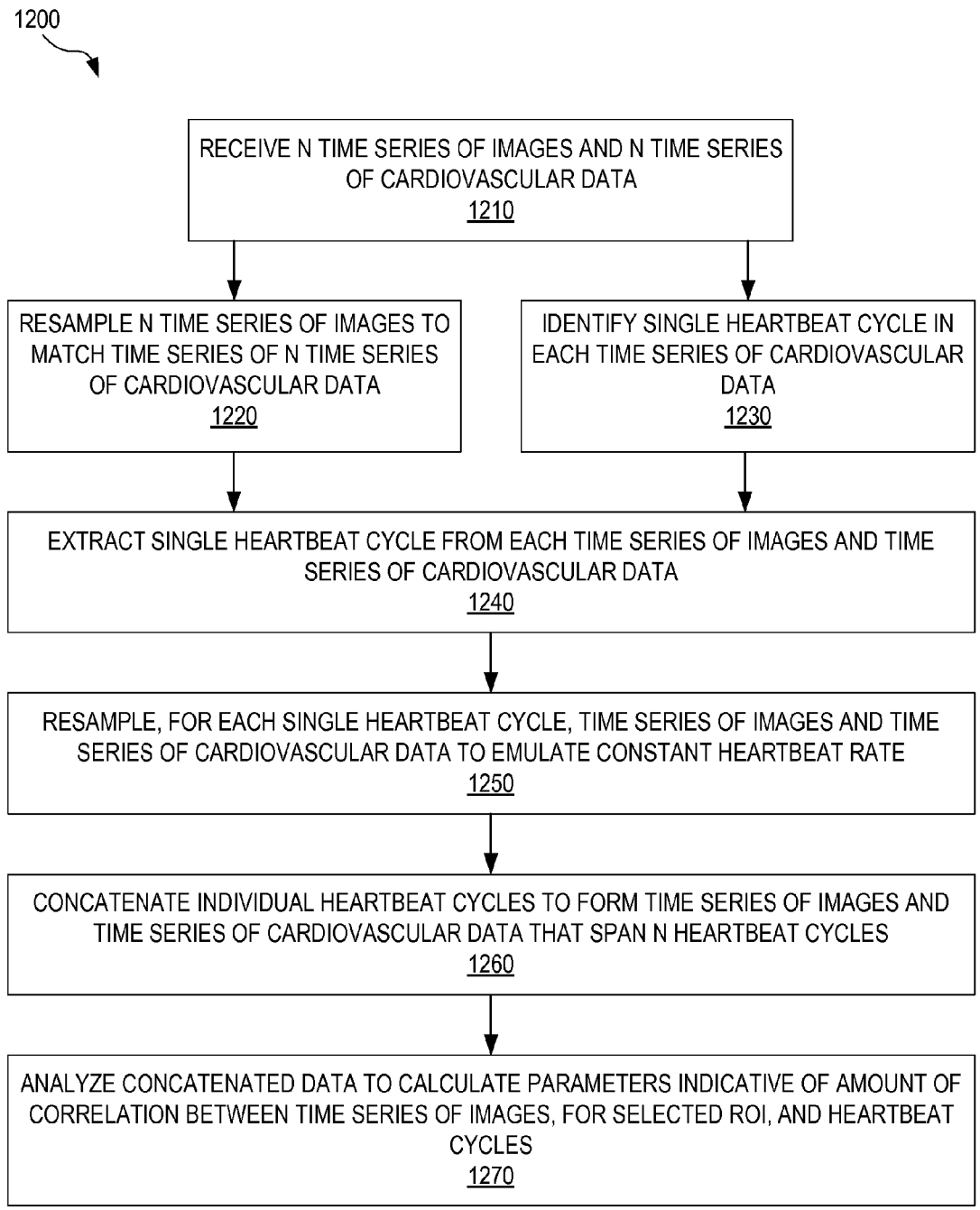
FIG. 12 illustrates a method for evaluating correlation between a time series of EIT images and a time series of pulse-oximeter measurements, according to an embodiment.

FIG. 12 illustrates a method 1200 used in this Example for evaluating correlation between the time series of EIT images and the time series of pulse-oximeter measurements. Method 1200 is an embodiment of method 300 (FIG. 3).

Following data acquisition and Δσ image reconstruction, the temporal data (Δσ images, $\Delta\sigma_n$, and biophysical signal, $y_n$) were analyzed in order to assess (a) the beat-to-beat correspondence between the cardiovascular and Δσ signatures and (b) the inter-beat statistics of these signals. The cardiovascular signal being sampled (either the ECG or pulse-ox waveform) provided a surrogate measure of blood flow through the breast and was the means of comparison to which the temporal conductivity changes were evaluated. Note that this signal provided only a relative reference for comparison since it is dependent on the location of the pulse-ox (i.e. finger-based vs. carotid sampling). Sampling 40 frames/burst at 17.3 fps provided a 2.3 second sampling window. Resting heart rates typically ranged from 50-90 bpm (0.83-1.5 beats per second (bps)) resulting in 1.9 to 3.45 heart beats being sampled per burst during this 2.3 second window. Relatively large conductivity changes were present during phantom imaging and the signatures acquired from a single acquisition burst (40 frames) provided sufficient detail for identifying the temporal and spectral characteristics of the spatio-temporal conductivity variations induced. However, for dynamic breast imaging, the conductivity changes are much smaller and require additional processing over multiple bursts to characterize the signals. Specifically, a single heart beat was extracted from each 40-frame burst to provide multiple cardiac events for processing.

In a step 1210, method 1200 receives $N_{burst}$ time series of images $\Delta\sigma_n$ (the temporal change in conductivity sampled at an interval of $T_o=57.8$ ms) and $N_{burst}$ time series of cardiovascular data $y_n$ (the cardiovascular signal being monitored at a sampling interval of $T_c=16$ ms).

In a step 1220, method 1200 resamples the $N_{burst}$ time series of images $\Delta\sigma_n$ to match the series of times associated with the time series of cardiovascular data $y_n$. Step 1220 is an embodiment of step 530 (FIG. 5). Because $T_c \neq T_o$, $\Delta\sigma_n$ was resampled using cubic spline interpolation to match the sampling rate of $y_n$. This resampling was performed over each of the image nodes and ensured that the resampled signal, $\hat{\Delta\sigma}_n$, and $y_n$ were of the same length, with each sample occurring at equivalent instances in time. Each 40-frame burst was resampled in a similar fashion.

In a step 1230, method 1200 identifies and extracts a single heartbeat cycle in each time series of cardiovascular data $y_n$. Step 1230 is an embodiment of step 610 (FIG. 6). Step 1230 and subsequent steps 1240, 1250, 1260 and 1270 are collectively an embodiment of method 600 (FIG. 6). A single cardiac cycle was extracted from each burst. This was accomplished by determining successive peaks within the cardiovascular signal, $y_n$, and extracting the corresponding temporal points from within the $\hat{\Delta\sigma}_n$ sequence. Prior to peak detection, the cardiovascular signal at each time instant i was demeaned and normalized. Identifying the peak depended on the signal sampled and for the case of pulse-oximetry signatures, a derivative-based algorithm was employed as a simple, accurate and efficient mode of peak detection. To this end, the first-order difference, Δ, is calculated across the entire temporal sequence and normalized: $\Delta=y_{i+1}-y_i (i\in 1, 2, 3, \ldots N_{c,samples}-1)$ and $\hat{\Delta}=\Delta/\max(\Delta)$. A peak was defined as the time at which the maximum $\hat{\Delta}$ occurred within a predefined window beginning at the time point at which $\hat{\Delta}$ exceeded a specified threshold. The threshold, τ, was empirically determined by trial and error. The first peak, $\Gamma_1$, was defined as the maximum $\hat{\Delta}$ found within the window, ψ, following the first instance at which τ was exceeded, $i_\tau$: $\Gamma_1=\max(\hat{\Delta}_{i_\tau}, \hat{\Delta}_{i_{\tau+1}}, \hat{\Delta}_{i_{\tau+2}}, \ldots, \hat{\Delta}_{i_{\tau+\psi}})$. For the pulse-oximetry signals acquired here, a τ of 0.35 and ψ of 20 proved robust in detecting the first oxygen saturation peak in each of the acquired bursts. The second peak, $\Gamma_2$, was similarly found by providing the detection algorithm the cardiovascular signature ranging from the end of the first peak window, $i_\tau+\psi$, to the sequence end.

In step 1240, a single cardiovascular period and the corresponding $\hat{\Delta}_o$ sequence ranging from $\Gamma_1$ to $\Gamma_2$ were extracted from the original sequences $\tilde{y}=\hat{y}(\Gamma_1, \Gamma_1+1, \Gamma_1+2, \ldots \Gamma_2)$ and $\hat{\Delta\sigma}=\hat{\Delta\sigma}(\Gamma_1, \Gamma_1+1, \Gamma_1+2, \ldots \Gamma_2)$.

In step 1250, method 1200 resamples, for each single heartbeat cycle, the time series of images $\hat{\Delta\sigma}$ and the time series of cardiovascular data $\tilde{y}$ to emulate a constant heartbeat rate. Heart-rate variability is a well-established phenomenon which manifests itself in this Example as the temporal length of $\tilde{y}$ and $\tilde{\Delta\sigma}$ for each burst being variable. In order to account for this variability, the extracted single-beat sequences were resampled using cubic spline interpolation with a fixed number of samples (=40) to occur over a temporal duration of 1 second, effectively enforcing a 1 bps heart rate. By enforcing a fixed number of samples occurring over the 1 second interval, the sequences extracted from each burst were easily compared.

In step 1260, individual heartbeat cycles $\tilde{y}$ and $\tilde{\Delta\sigma}$ are concatenated to form a time series of images Δσ(t) and a time series of cardiovascular data y(t) that span multiple heartbeat cycles.

In step 1270, method 1200 analyzes the concatenated data generated in step 1260 to calculate parameters indicative of correlation between the time series of images Δσ(t), for one or more selected spatial ROIs, and the time series of cardiovascular data y(t). Image analysis consisted of extracting the mean Δσ within a specified spatial ROI from each frame, according to output of step 601 (FIG. 6). This extraction provided a temporal sequence of $\Delta\sigma_{ROI}(t)$ corresponding to a specific region inside the imaging domain. The temporal signature of each sequence was filtered using an 81-tap Hamming window with a cutoff frequency of 8.65 Hz (½ of the 17.3 Hz sampling frequency) and padded with zeroes prior to taking the 512-point Fast Fourier Transform (FFT). The power spectra, ΔΣ(f) and Y(f), were estimated as the square of the individual frequency components extracted from the FFT (i.e. $\Delta\Sigma(f)=|\text{IFFT}(\Delta\sigma(t))|^2$). In patients several spectral and temporal measures were used to parameterize the waveforms. Specific parameters are discussed in the following:

Spectral Correlation Coefficient, $r_s$: Correlation coefficient between the oxygen-saturation spectra, Y(f) and the ΔΣ(f) spectra. The correlation was obtained for frequencies ranging from 1 Hz to 8.65 Hz. DC to 1 Hz signals were not included because the shortest frequencies able to be gauged were 1 Hz due to the resampling procedure.

Maximum Temporal Correlation Coefficient, $r_{t,max}$: Maximum correlation coefficient occurring between the oxygen-saturation signal and a phase-shifted Δσ signal (calculated according to an embodiment of method 700 of FIG. 7). The correlation coefficient was computed at each degree of phase shift and $r_{t,max}$ denotes the maximum correlation coefficient obtained through the entire phase-shifting procedure.

Phase Shift $\varphi(r_{t,max})$ at $r_{t,max}$: The phase shift leading to the maximum correlation coefficient $(r_{t,max})$ between the oxygen saturation signal and $\Delta\sigma$ signal (calculated according to an embodiment of method 700 of FIG. 7). This represents the phase shift required to produce the maximum correlation coefficient.

Spectral Power Ratio, $P_{x:y}$: The ratio of total spectral power within one frequency band in reference to a second frequency band as defined by: $P_{x:y} = \int_{f_1}^{f_2} \Delta\Sigma(f) df / \int_{f_3}^{f_4} \Delta\Sigma(f) df$. Three spectral power ratio's for each $\Delta\Sigma$ spectrum were computed: $P_{low:full}$ ($f_1=1$ Hz, $f_2=4.325$ Hz, $f_3=1$ Hz, $f_4=8.65$ Hz), $P_{high:full}$ ($f_1=4.325$ Hz, $f_2=8.65$ Hz, $f_3=1$ Hz, $f_4=8.65$ Hz), and $P_{low:high}$ ($f_1=1$ Hz, $f_2=4.325$ Hz, $f_3=4.325$ Hz, $f_4=8.65$ Hz).

Phantom Imaging—Experimental Configuration

Figure 13:
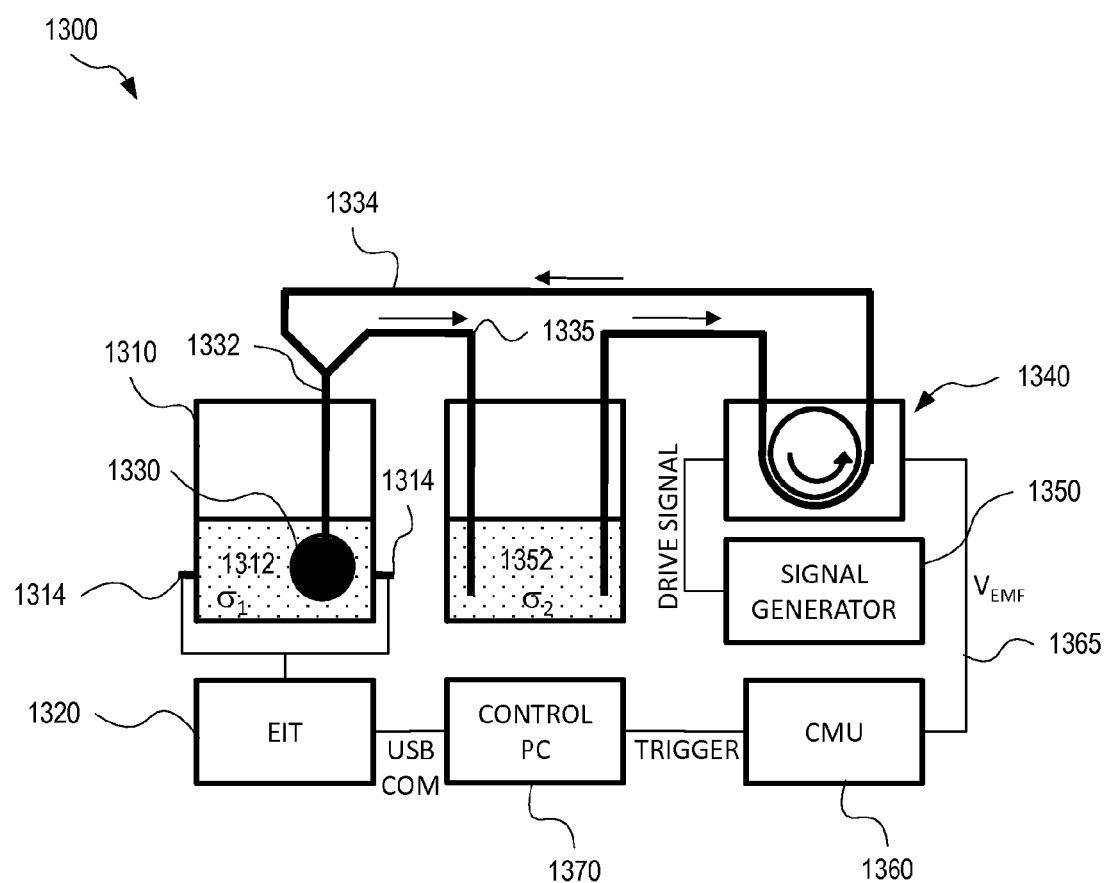
FIG. 13 illustrates a system for cardiovascular-dynamics correlated phantom imaging, according to an embodiment.

FIG. 13 illustrates the system 1300 used for the cardiovascular-dynamics correlated phantom imaging. A series of phantom experiments were conducted in the same way that patient data was collected in order to evaluate system performance. An 8 cm circular tank 1310 fitted with 1 cm stainless steel electrodes 1314 was positioned within the EIT system 1320. A saline solution 1312 ($\alpha$=0.113 S/m) was added to tank 1310 to a height of 2 cm just covering the bottom layer of electrodes 1314. A pulsating latex balloon 1330 positioned within saline solution 1312 was used to simulate a dynamically varying low conductivity volume. A two-port Y-type connector 1332 interfaced to balloon 1330 allowed fluid to flow in and out of the membrane. Flexible tubing 1334 extending from one of the ports was interfaced through a programmable COBE heart-lung precision blood pump 1340 (COBE Lakewood, Colo.) to a second saline bath 1352 ($\sigma$=0.014 S/m). This solution was pumped through balloon 1330, and a flexible tube 1335 connected to the second port acted to drain fluid from balloon 1330. An Agilent 33120A arbitrary waveform generator 1350 (Agilent Technologies, Santa Clara, Calif.) was used to generate both sine and square waves of particular amplitudes and frequencies to drive pump 1340. The back $V_{emf}$ signal of the pump was sensed by cardiovascular monitoring unit 1360 (PMD-1608FS discussed above) and used to trigger EIT data acquisition by EIT system 1320 through control PC 1370.

Eight different pumping schemes were imaged. Sine wave excitations at 1 Hz, 2 Hz, and 4 Hz were used, followed by square wave excitations at 1 Hz, 2 Hz, and 4 Hz. The drive amplitude for each of these waveforms was a constant 1 $V_{pp}$, which resulted in balloon 1330 diameter changes of 1-3 mm per cycle with the maximum balloon 1330 diameter extending to approximately 2 cm. Ten 40-frame bursts were collected at 17.3 frames per second for each driving configuration at 127 kHz.

Phantom Imaging—Experimental Results

Figure 14A:
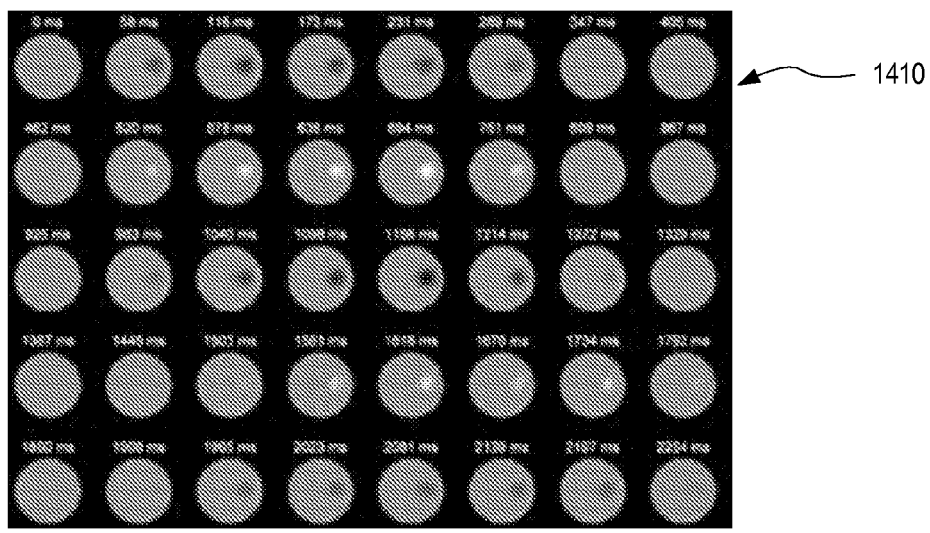
FIG. 14 shows exemplary temporal sequences of electrical impedance tomography images of a phantom.
Figure 14B:
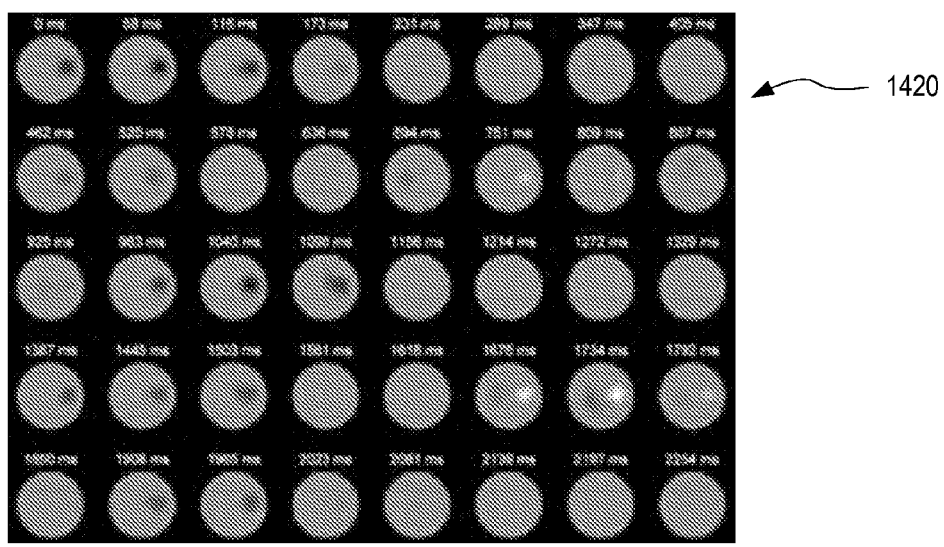
Figure 14C:
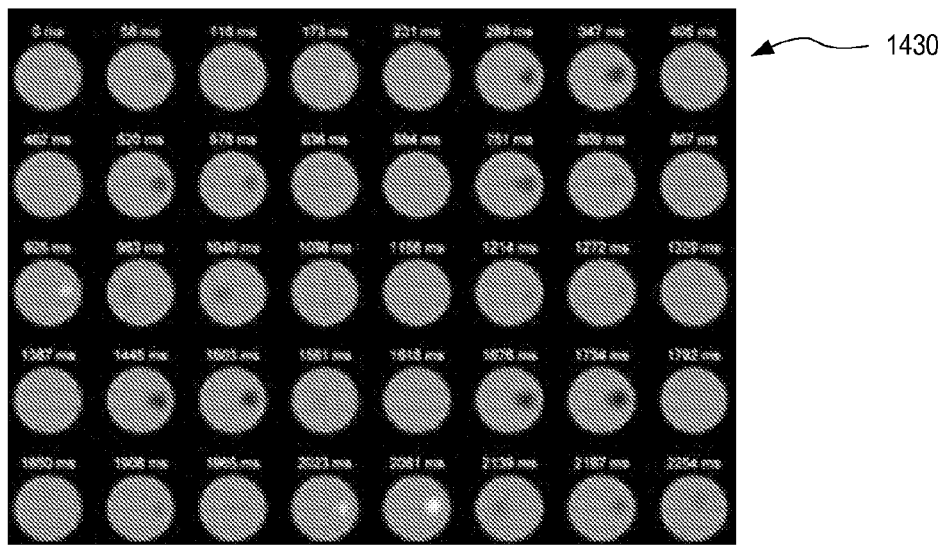

FIG. 14 displays exemplary temporal sequences 1410, 1420, and 1430 of $\Delta\sigma$ images occurring over a single 40-frame burst for sine wave excitation at 1 Hz, 2 Hz, and 4 Hz, respectively. Each of temporal sequences 1410, 1420, and 1430 is displayed such that the first row should be read from left to right, then the second row should be read from left to right, etc. The greyscale map used in FIG. 14 represents $\Delta\sigma$ and ranges from −8 mS/m to 8 mS/m.

The pulsing balloon 1330 was well localized in each burst of frames for all excitation drive configurations. Regions of low and high $\Delta\sigma$, corresponding to inflation and deflation of balloon 1330, have a decreased temporal period as the excitation frequency increases. A 2 cm diameter circular ROI was defined around the node having maximum change in conductivity over the course of the burst (x=2.2 cm, y=0.2 cm) and the mean $\Delta\sigma$ within the ROI from each frame was extracted.

Figure 15A:
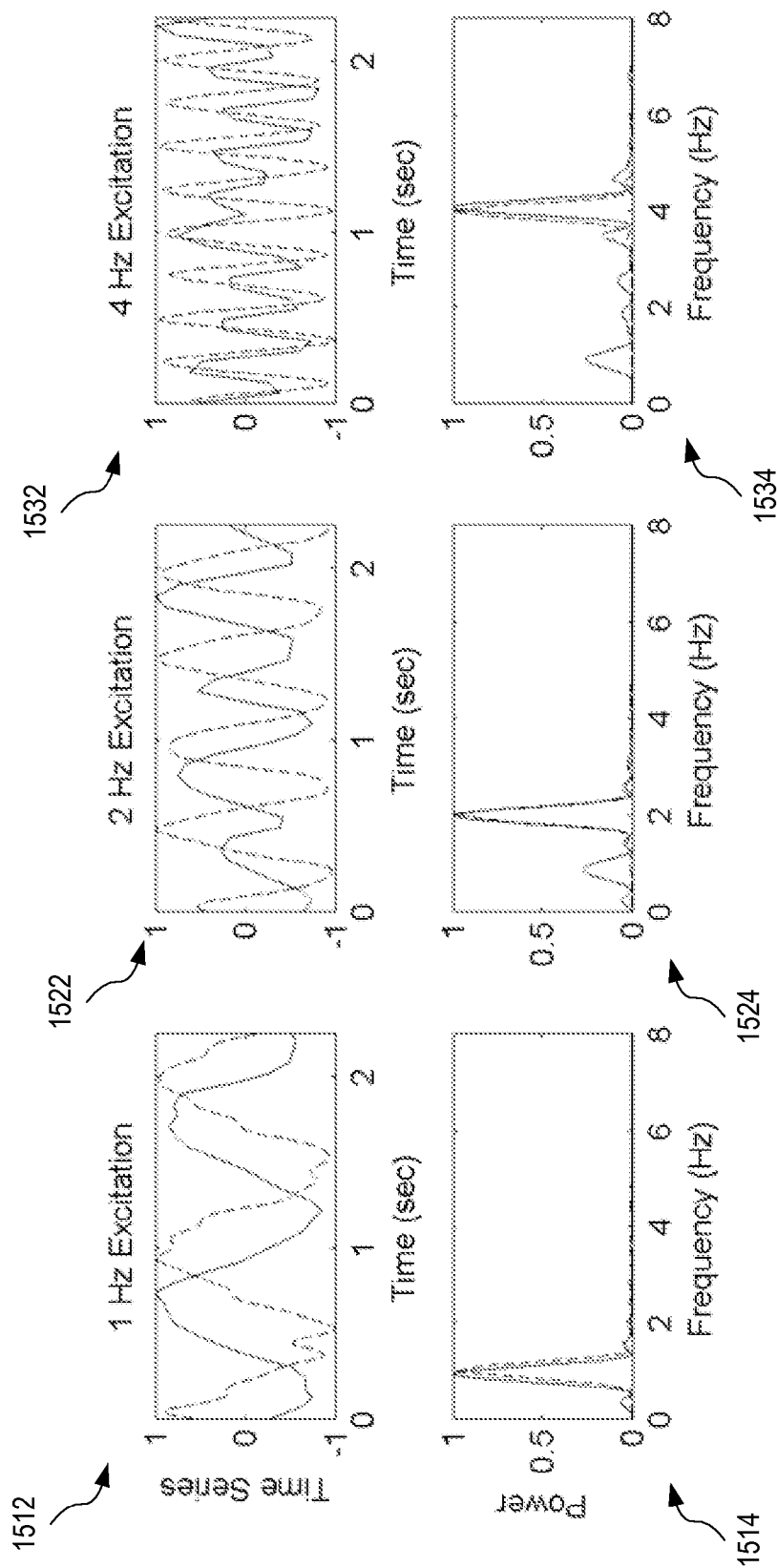
FIGS. 15A and 15B show exemplary temporal sequences and power spectra for sine wave excitation and square wave excitation in electrical impedance tomography imaging of a phantom.
Figure 15B:
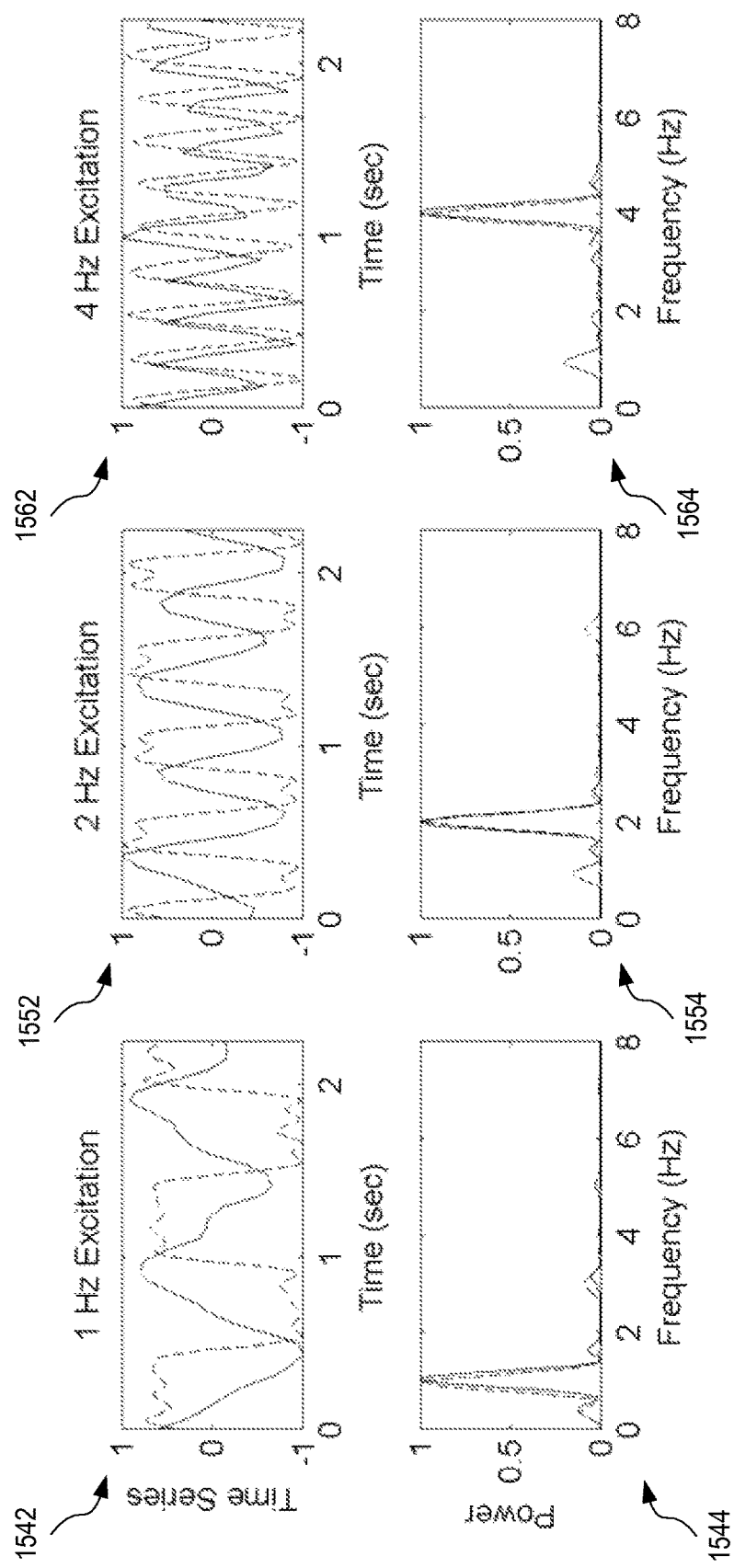

FIGS. 15A and 15B show temporal sequences and power spectra for each of the drive frequencies with sine wave excitation and square wave excitation, respectively. Plots 1512, 1522, and 1532 show temporal sequences at 1 Hz, 2 Hz, and 4 Hz drive frequency, respectively. Plots 1514, 1524, and 1534 show power spectra at 1 Hz, 2 Hz, and 4 Hz drive frequency, respectively. Likewise, plots 1542, 1552, and 1562 show temporal sequences at 1 Hz, 2 Hz, and 4 Hz drive frequency, respectively, and plots 1544, 1554, and 1564 show power spectra at 1 Hz, 2 Hz, and 4 Hz drive frequency, respectively. Solid line denotes $\Delta\sigma$ and dashed line denotes $V_{emf}$ sensed by the EIT system for triggering. Note that in square wave variation, harmonics in $\Delta\sigma$ occur at 1 Hz, which are absent in the higher frequencies because of the low pass filter effect of the long fluid paths within the system.

The temporal sequences and power spectrum from each of the drive configurations demonstrates that the temporal changes in conductivity and its spectral signature correlated well with that of the recorded pump drive voltage, $V_{emf}$. The phase shift noted between the temporal $\Delta\sigma$ and $V_{emf}$ traces is due to the phase introduced by the hydrodynamic coupling between the pump and fluid network. During sine wave excitation, the principal spectral component for each drive configuration coincided with the programmed drive frequency at 1 Hz, 2 Hz, and 4 Hz. The additional peak in the 2 Hz and 4 Hz configurations at ~1 Hz is due to rigid balloon 1330 translation and saline solution displacement as the tubing moved during the pumping procedure. During square wave excitation, pump 1340 was unable to generate a square wave at 4 Hz due to inertial damping within the motor. At 1 Hz and 2 Hz, however, pump 1340 was able to specify a square wave rotation (see FIG. 15B). As expected the hydrodynamic network interfacing pump 1340 and reservoir to balloon 1330 acted as a low pass filter. As a result, the $\Delta\sigma$ images acquired during square wave excitation do not clearly display the sharper edges (high frequencies) present in the recorded $V_{emf}$ of pump 1340. However, within the spectral domain, the $\Delta\sigma$ signatures at 1 Hz show both the principal component at 1 Hz and the $1^{st}$ odd harmonic at 3 Hz similarly to the $V_{emf}$ spectrum. This harmonic was not present during sine wave excitation and demonstrates the system's ability to sense multi-frequency components within a single temporal event. The odd harmonics were not found in the $\Delta\sigma$ spectra for the 2 Hz square wave because the low-pass action of the hydrodynamic network acted to filter out these small harmonics. In addition, the 1st odd harmonic (12 Hz) for the 4 Hz excitation fell outside the bandwidth of EIT acquisition (8.65 Hz).

Breast Imaging—Procedure

Women were recruited to be imaged with dynamic EIT, according to method 300 (FIG. 3) and using an embodiment of system 100 (FIG. 1), as part of an Institutional Review Board approved study at the Dartmouth-Hitchcock Medical Center (Lebanon, N.H., USA). The imaging procedure is described in detail in R. J. Halter, A. Hartov, K. D. Paulsen, "A broadband high frequency electrical impedance tomography system for breast imaging," IEEE Transactions on Biomedical Engineering, vol. 55, pp. 650-59, 2008 which is incorporated by reference herein in its entirety. Briefly, each woman was positioned so that one breast hung pendant through an opening in the EIT examination table. The electrodes were actuated to come into contact with the breast and an effective contact impedance was gauged at each electrode to ensure that all were in contact with the skin. Conductive gel administered between the electrode and the skin reduced the level of this contact impedance. A finger-based pulse-oximetry sensor was placed on the index or middle finger of the patient and interfaced to an N-395 Pulse Oximeter System (Nellcor Pleasanton, Calif. USA), an embodiment of cardiovascular measurement device 120 (FIG. 1). The device had an analog output port that provided a filtered oxygen saturation signal to the cardiovascular monitoring unit of the EIT system. This signal provided triggering for EIT image acquisition and was recorded during image acquisition so that post-acquisition correlation analysis between the cardiovascular and $\Delta\sigma$ signals could be evaluated.

In the same way the balloon experiments were conducted, multiple 40-frame bursts of EIT voltages were acquired at 17.3 fps. The individual bursts were triggered to begin when the pulse-oximetry signal reached a user-specified threshold selected to occur near the apex of oxygen-saturation during each heartbeat. This threshold was specifically selected for each patient based on the characteristics of the measured signal which varied due to differences in sensor placement, finger thickness, and other factors. Triggering image acquisition to start precisely at the peak of the pulse-oximetry signal was not critical since a single full heart-beat event was extracted from each data-burst using method 1200 (FIG. 12).

Following data acquisition (both EIT and pulse-oximetry voltages), $\Delta\sigma$ images were reconstructed for each 40-frame burst, method 1200 (FIG. 12) was implemented, and the correlative and spectral power parameters ($r_s$, $\varphi(r_{t,max})$, $r_{t,max}$, $P_{low:full}$, $P_{high:full}$, $P_{low:high}$) were extracted for a particular ROI (described below). The procedure was performed for both the left and right breast of each patient imaged in this study.

The clinical evaluation of the cancer patients participating in this study, included MRI-based tumor identification and localization and biopsy-based pathological confirmation of disease. Clinical reports included the approximate tumor location (side and clock face) and tumor size. Because of the approximate nature of the description of tumor location and because there was not a one-to-one correspondence between MR and EIT imaging, the spatial ROIs selected for analysis were assigned to be all nodes within a particular $\Delta\sigma$ image quadrant. Quadrants designated as 1, 2, 3, and 4 corresponded to the area on a clock-face covered by 12:00-3:00, 3:00-6:00, 6:00-9:00, and 9:00-12:00, respectively. Based on the clinical tumor description, each quadrant was designated as either benign or malignant.

Breast Imaging—Results

Nineteen (19) women were imaged following this protocol (10 with cancer, 9 with no cancer). Among the 19 women imaged, there were 13 quadrants identified as malignant and 139 designated at benign (152 total quadrants=19 women×2 sides×4 quadrants).

FIG. 16 shows tumor characteristics for the cancer containing quadrants in tabular form, wherein RD denotes Radiographic Density, Bx Path denotes biopsy based pathological findings, and Enhancement and Kinetics describe the washout dynamics of contrast-enhanced MR studies. ED=extremely dense, HD=heterogeneously dense, SC=scattered, DCIS=ductal carcinoma in situ, IDC=intraductal carcinoma. No MRI was obtained for patient 9. In three patients (2, 8, and 10), the lesions were identified at the 12:00 location and were therefore assigned to both quadrants 1 and 4. The temporal $\Delta\sigma$ signatures observed in this patient cohort provided less obvious information than those obtained from the balloon experiments due to the much smaller changes in $\Delta\sigma$ that occurred in vivo.

Figure 17A:
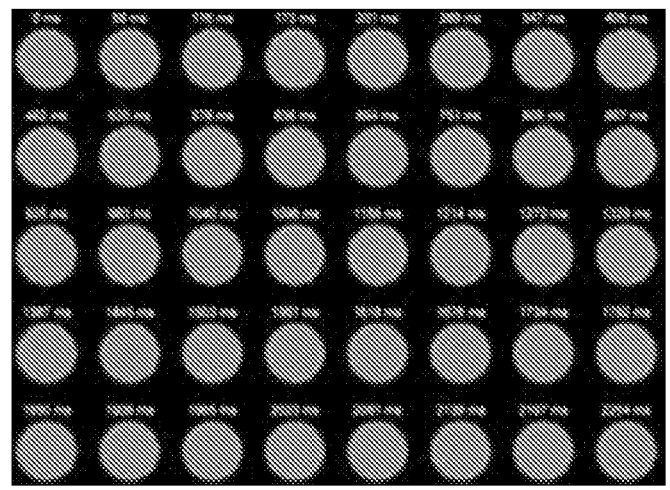
FIGS. 17A and 17B show exemplary time series of images a control (normal) and cancer patient, respectively.
Figure 17B:
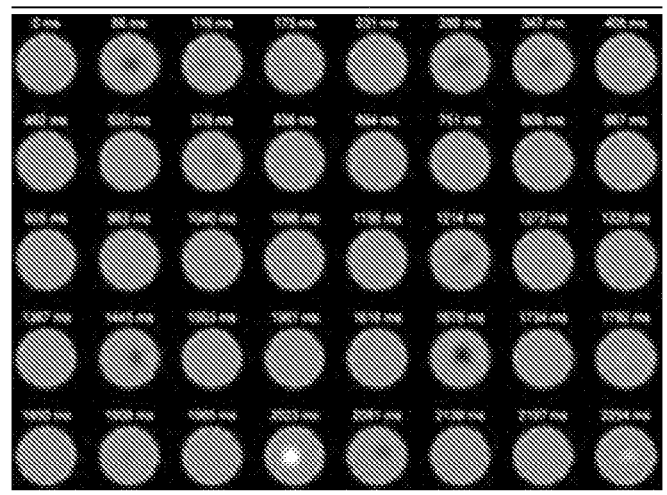

FIGS. 17A and 17B show exemplary 40-frame $\Delta\sigma$ image bursts for a control (normal) and cancer patient, respectively with no obviously differentiating features noted between the two. A 30 mm×30 mm×25 mm tumor was identified in MRI in quadrant 4 of the cancer patient (FIG. 17B). The greyscale map represents $\Delta\sigma$ and ranges from −5 mS/m to 5 mS/m.

Figure 18:
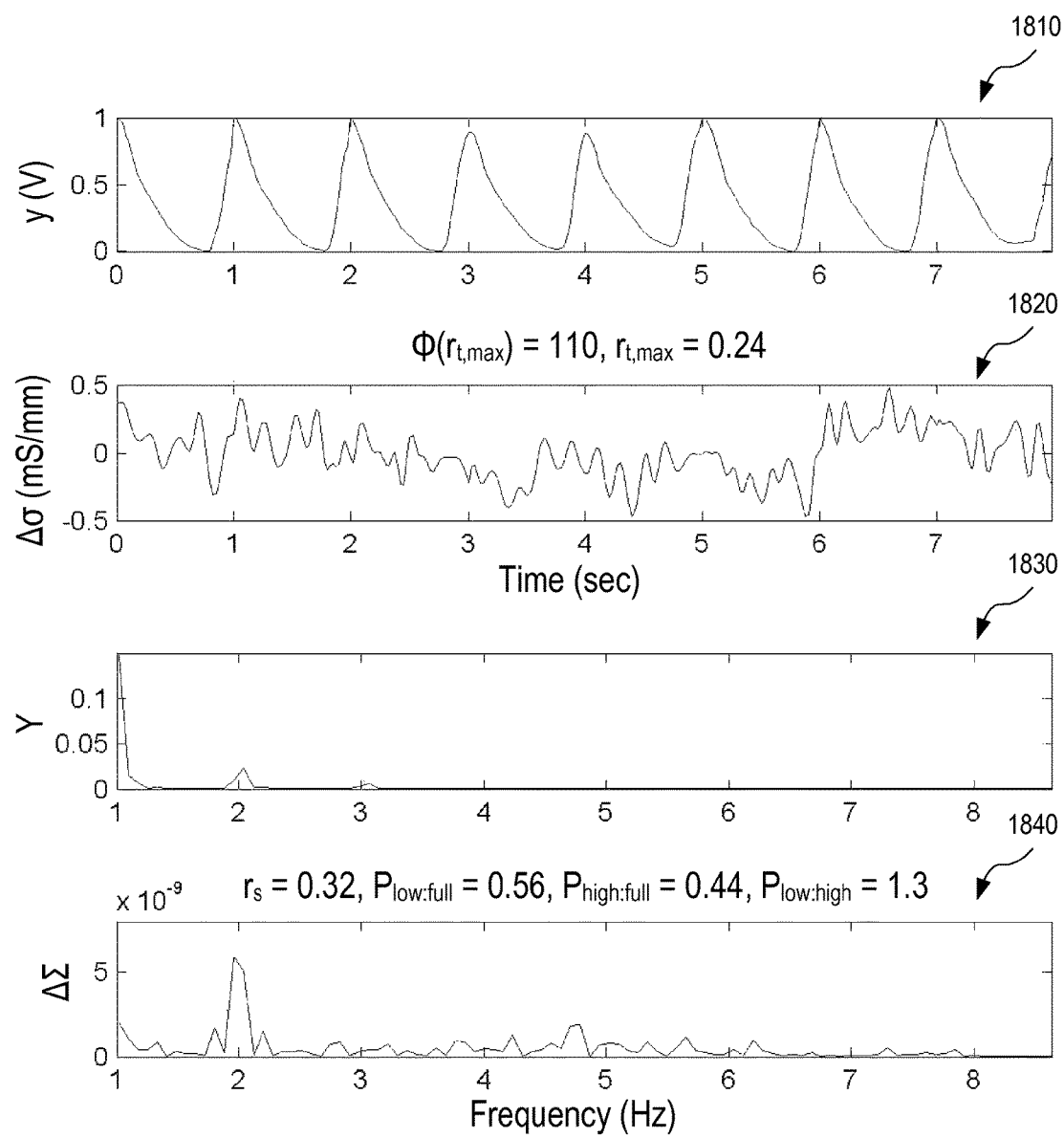
FIG. 18 shows temporal and spectral signatures extracted from an exemplary benign quadrant, along with associated oxygen-saturation signals.

FIG. 18 shows temporal and spectral signatures extracted from a benign quadrant of patient 2 along with associated oxygen-saturation signals. Plots 1810 and 1820 show oxygen-saturation (y) and change in conductivity ($\Delta\sigma$) as a function of time. Plots 1830 and 1840 show power spectrum for these signals, Y and $\Delta\Sigma$, respectively. Correlative and power spectral ratio parameters including $r_s$, $P_{low:full}$, $P_{high:full}$, and $P_{low:high}$ are also displayed in FIG. 18.

Figure 19:
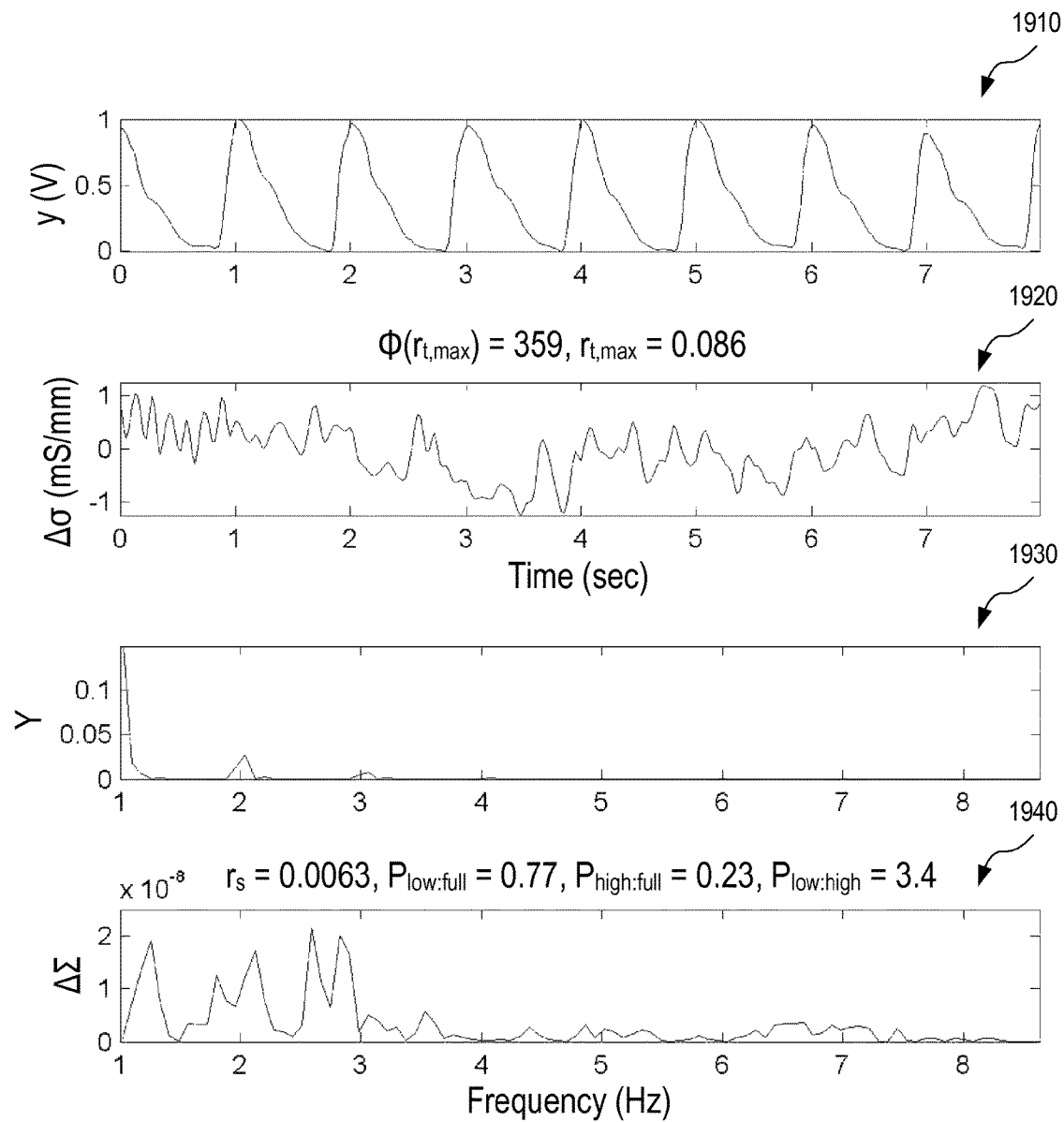
FIG. 19 shows temporal and spectral signatures extracted from an exemplary malignant quadrant, along with associated oxygen-saturation signals.

FIG. 19 shows temporal and spectral signatures extracted from a malignant quadrant of patient 4 along with associated oxygen-saturation signals. Plots 1910 and 1920 show oxygen-saturation (y) and change in conductivity ($\Delta\sigma$) as a function of time. Plots 1930 and 1940 show power spectrum for these signals, Y and $\Delta\Sigma$, respectively. Correlative and power spectral ratio parameters including $r_s$, $P_{low:full}$, $P_{high:full}$, and $P_{low:high}$ are also displayed in FIG. 19.

The correlative and spectral power parameters displayed in FIGS. 18 and 19 demonstrate two features that were observed in multiple cases. First, the temporal and spectral correlations between $\Delta\sigma$ and the oxygen-saturation signatures are quite low ($r<0.09$) for the cancer quadrant (FIG. 19), while the benign quadrant (FIG. 18) demonstrates a larger correlation ($r>0.24$). Second, the spectral traces have more dispersive and dominant low frequency components in the cancer containing quadrant (FIG. 19). When the quadrants were divided amongst benign and malignant groups and compared, these two observations were consistent and significant.

FIG. 20 shows, in tabular form, statistics of normal and cancer patient obtained from processing of each quadrant of data.

Figure 21:
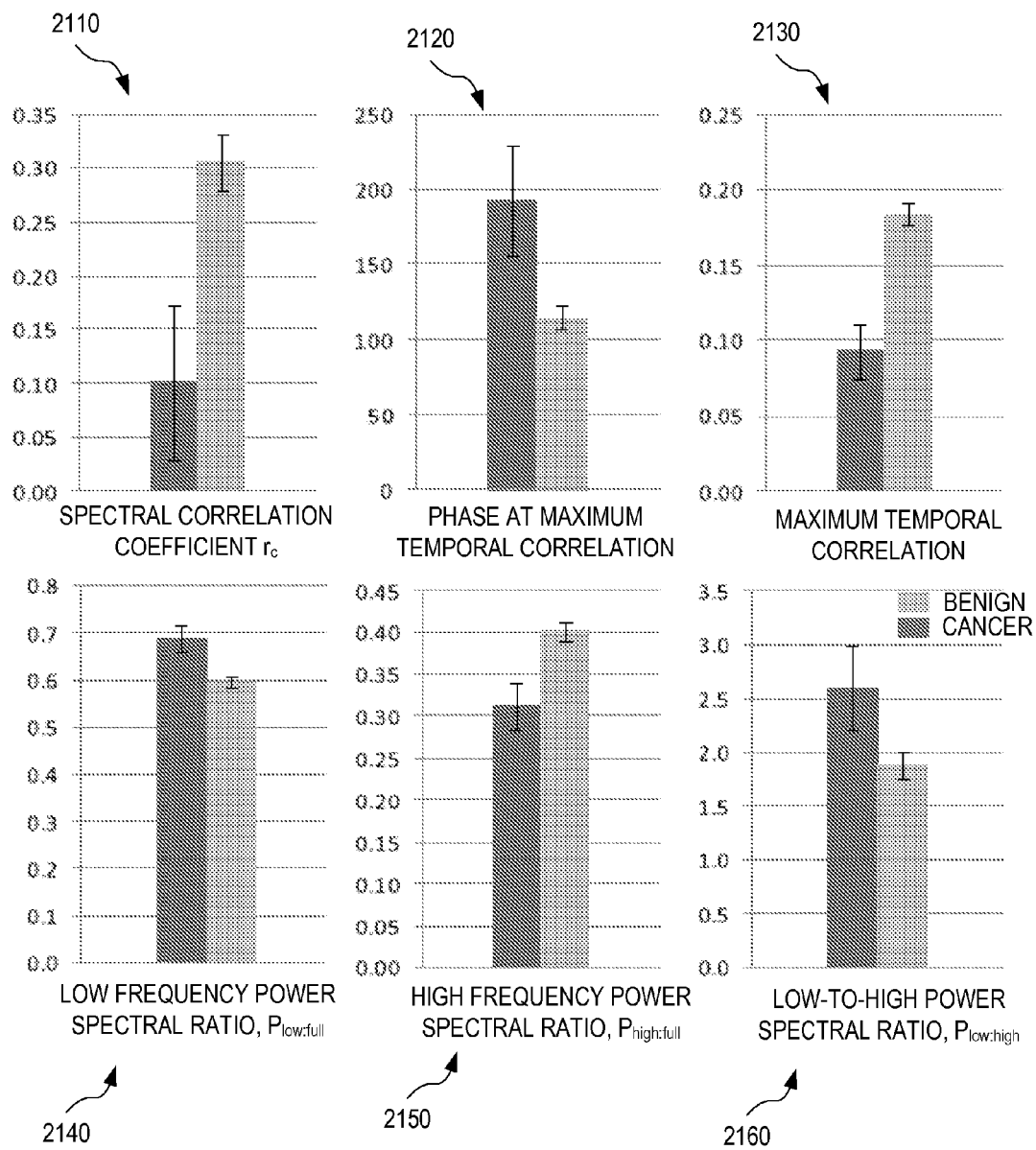
FIG. 21 shows mean parameters for exemplary normal and cancer patients.

FIG. 21 shows mean parameters for normal and cancer patients. Plots 2110, 2120, 2130, 2140, 2150, and 2160 show $r_s$, $\varphi(r_{t,max})$, $r_{t,max}$, $P_{low:full}$, $P_{high:full}$, $P_{low:high}$, respectively. In each of plots 2110, 2120, 2130, 2140, 2150, and 2160, the leftmost column is derived from malignant quadrants and the rightmost column is derived from benign quadrants.

As evident from FIGS. 20 and 21, all parameters were found to be significantly different ($p<0.05$) when grouped as malignant and benign, and all but $P_{low:high}$ reached significance levels of $p<0.01$. In addition, no significant differences ($p>0.1$) were noted between the spectral power ratios of the benign and malignant oxygen-saturation signals verifying the fact that the cardiovascular signals were similar in both patient cohorts.

Figure 22:
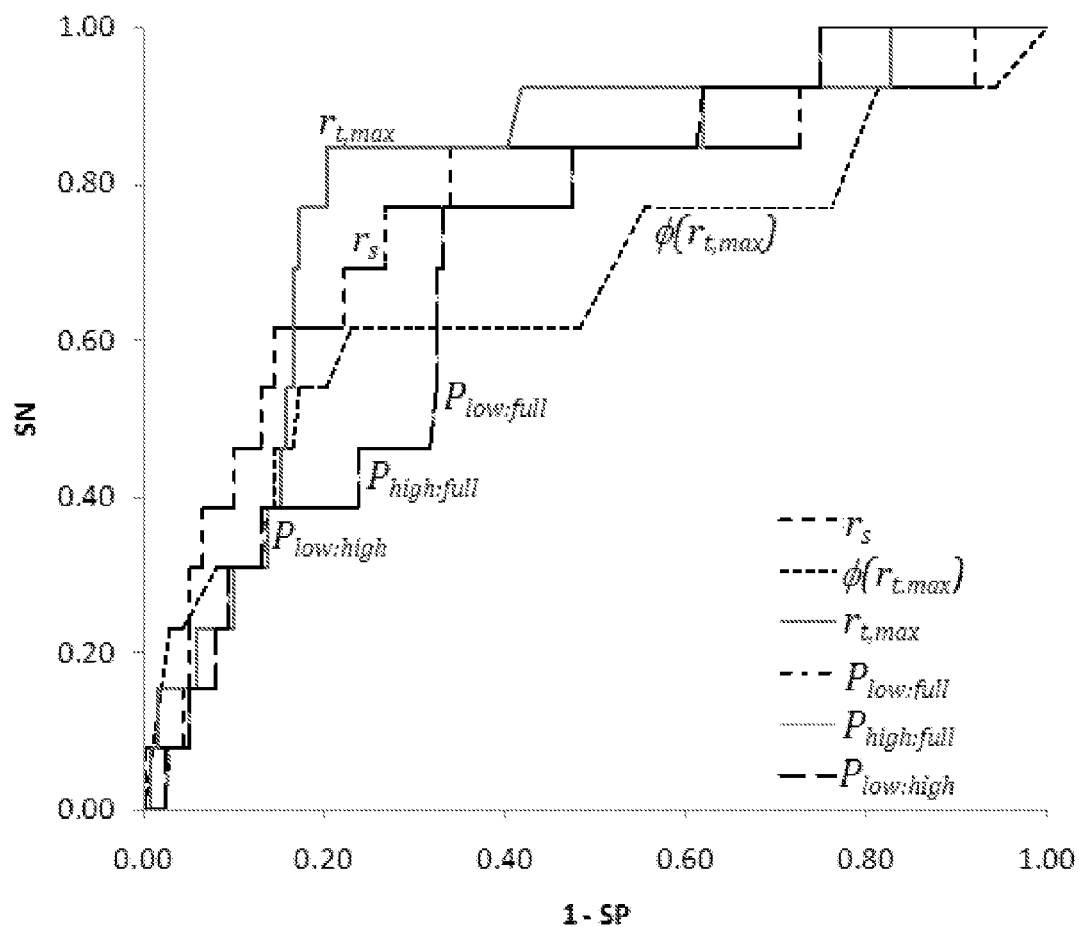
FIG. 22 shows receiver-operating characteristics for each of the parameters displayed in FIG. 21.

FIG. 22 shows receiver-operating characteristics for each of the parameters displayed in FIG. 21.

FIG. 23 shows, in tabular form, clinical metrics associated with the receiver-operating characteristics displayed in FIG. 22, such as the area under the curve (AUC) and other relevant clinical metrics including sensitivity (SN), specificity (SP), accuracy (ACC), positive predictive value (PPV), and negative predictive value (NPV). The AUC's of all parameters were greater than 0.67 with $r_{t,max}$ being the best discriminator with an AUC of 0.8, SN of 77%, and SP of 81%. The rather low PPV and high NPV are due to the large difference between benign and malignant sample sizes (139 quadrants vs. 13 quadrants). The thresholds for obtaining these levels of SN and SP are also provided in the FIG. 23.

Breast Imaging—Discussion

The normal breast is vascularized with a well-organized and regulated network of large feeding arteries and veins coupling into smaller arterioles, capillaries, and venules. The branching pattern is typically dichotomous as the network extends from the chest wall through the length of the breast. Around tumors, the vasculature environment is significantly different. Here, the vasculature is of irregular size, shape, and branching pattern and the network lacks normal hierarchy with haphazard branching patterns of trifurcated, uneven diameter vasculature junctions. Vessel density is higher around the tumor periphery with the mean vessel density at the tumor edge being 4-10 times higher than that inside the tumor. In addition, the individual vessels are compromised, with larger inter-endothelial junctions, increased fenestrations, vesicles and vesico-vascular channels and lack of normal basement membrane. These features result in lower perfusion rates (blood flow per volume), lower red blood cell velocity, heterogenous and chaotic blood flow around the tumor periphery, and a situation in which plasma oozes from the tumor periphery into the surrounding normal tissues. These abnormalities in blood flow dynamics generate different temporally-varying conductivity environments than those associated with the benign breast.

While the Δσ images observed here (FIGS. 17A and 17B) do not display well-resolved blood flow and vasculature patterns, the average value within specific regions of interest do appear to provide signatures that are significantly different in benign versus malignant breast tissues. The lower correlative parameters ($r_s$ and $r_{t,max}$) for malignant regions potentially arise from the heterogeneous blood flow around and within the tumor. In benign vasculature, the blood flow is more homogenous and more synchronized with the cardiovasculature signature which may explain the somewhat higher correlative parameters observed in these regions. For both malignant and benign tissues these correlative factors are only modest (mean r<0.306); this is potentially due to the effect of averaging a full quadrant of data in the analysis. Smaller ROI's will potentially provide areas with higher correlations; however, for the purpose of this study one-to-one correspondence between EIT and clinical MR images was not available and precluded a more refined ROI definition.

Both benign and malignant quadrants had the majority of the spectral energy concentrated in the low frequency band of 1 to 4.325 Hz, similarly to the oxygen-saturation (blood flow) signatures (FIGS. 18 and 19). The malignant quadrants, however, had a larger proportion of the energy in this lower band as compared to the higher frequency band (2.6 vs. 1.8, FIG. 20). Leaky vasculature surrounding tumors provides low resistance pathway for blood to "ooze" into the interstitial spaces which may produce more low frequency blood flow signatures than those occurring in uncompromised, more rigid benign vasculature. Further, the low frequency energy appears to be more dispersive in the malignant quadrants than in the benign quadrants (e.g. see FIGS. 18 and 19). This observation may arise from the extensive microvasculature around tumors which has been demonstrated to promote velocity fluctuations that might explain the more dispersive spectral content of the blood flow signatures in the cancer quadrants. The hypotheses formulated from these observations require further experimentation to better understand the biophysical mechanisms producing the effects. Animal models explicitly evaluating the dynamically changing electrical properties associated with pulsatile blood flow through tumor vasculature may provide further insight.

Despite not having a definitive explanation for the significant differences observed between benign and malignant blood flow patterns as gauged by EIT, the clinical metrics computed suggest this modality has potential for differentiating benign from malignant tissues within the breast. The optimum discriminating parameter, $r_{t,max}$, provides a sense of how well the changing conductivity distribution within a region correlates with the periodic blood flow pattern. In benign tissues this parameter seems to have a higher correlation (~0.3) compared to malignant tissues where very little correlation (~0.09) appears, suggesting that in these regions the heterogeneous flow patterns associated with malignancy do not follow that of the cardiac-driven blood flow.

Example II: Electrohemodynamic Correlation Imaging in Breast

In this Example, an embodiment of system 900 (FIG. 9) is used to create images of the spatial correlation of temporally varying electrical properties of breast tumors to pulsatile oxygen-saturation signatures. This Example utilizes an embodiment of system 900, wherein imaging device 110 (FIG. 1) is an EIT imaging device, cardiovascular measurement device 120 (FIG. 1) is a pulse-oximeter, and second imaging device 910 is an MRI device. Additionally, this example utilizes an embodiment of method 600, wherein step 601 is performed based upon images generated by the MRI device. Specifically, EIT images were recorded synchronously with pulse-oximetry in a series of 18 women (8 with cancer, 10 without cancer) at 20 frames per second for time series of 7-10 cardiac cycles. Using an embodiment method 300 (FIG. 3) including step 350, correlations maps (embodiments of the correlation-indicating images discussed in connection with step 350) representing the relationship between temporally varying electrical conductivity and pulse-oximetry were computed for both breasts of each subject. Significantly lower correlations were found in malignant as compared to benign regions, and appear to serve as surrogate measures of tumor hemodynamics likely as a result of the vastly different vascular patterns in malignancies. The correlation metric provided predictive clinical value and is suggested as a potential biomarker for use in screening, diagnostic, or therapy monitoring populations.

Results—Patient Population

Bilateral pulse-oximetry gated dynamic electrical conductivity images of the breast were acquired from 18 women. Eight of these participants had biopsy confirmed carcinoma (American College of Radiology (ACR) BIRADS category 6), one woman had a biopsy confirmed benign parenchymal lesion noted on mammography (ACR BIRADS category 4B), and nine women had no mammographic abnormalities (ACR BIRADS category 0).

FIG. 24 shows patient characteristics. Radiographic density categories are: extremely dense (ED), heterogeneously dense (HD), and scattered density (SD).

FIG. 25 shows abnormal cohort characteristics, wherein IDC refers to intraductal carcinoma, DCIS refers to ductal carcinoma in situ. No MRI was obtained for patient 9; characteristics for patient 9 are based upon mammographic interpretation only.

Results—Correlation Images of Pulsatile Conductivity

Figure 26A:
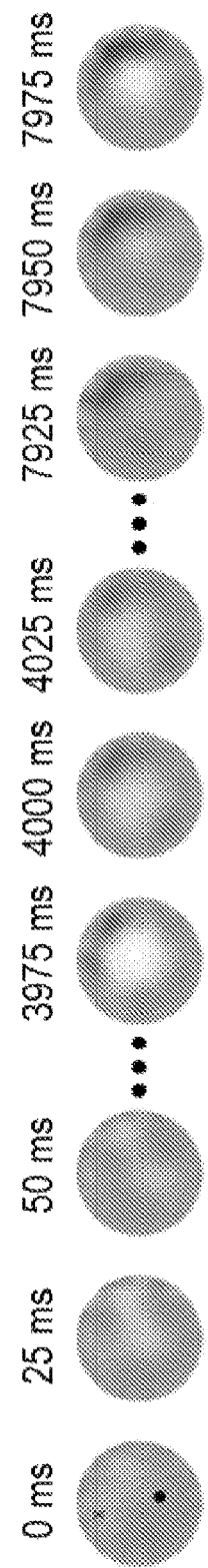
FIGS. 26A-E show a representative sequence of changing conductivity and its correlation with pulsatile oxygen saturation for a woman with a pathologically confirmed inflammatory breast cancer.
Figure 26B:
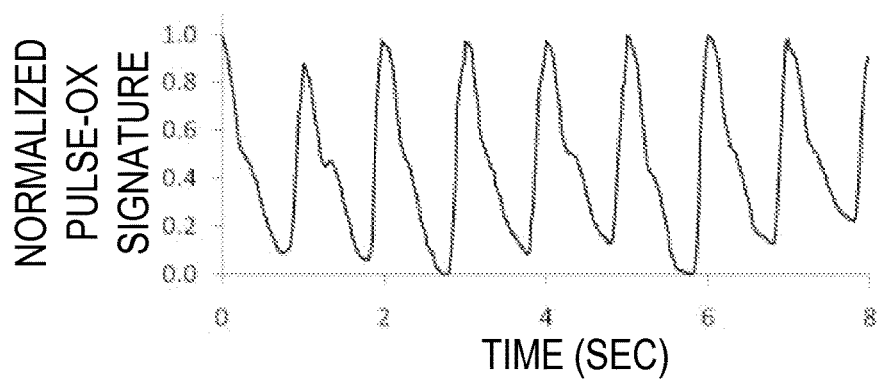
Figure 26C:
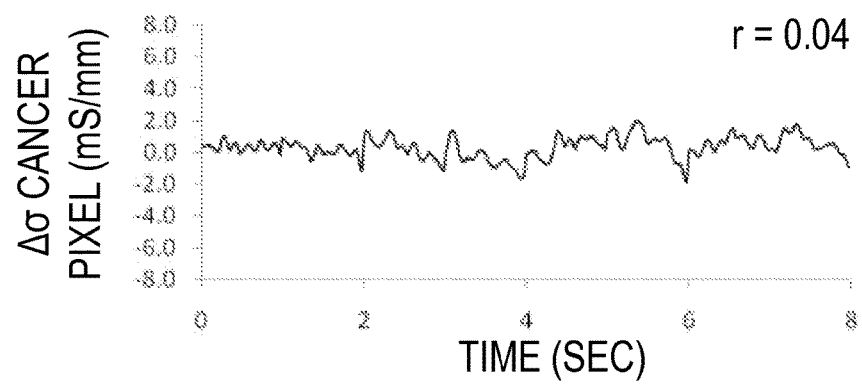
Figure 26D:
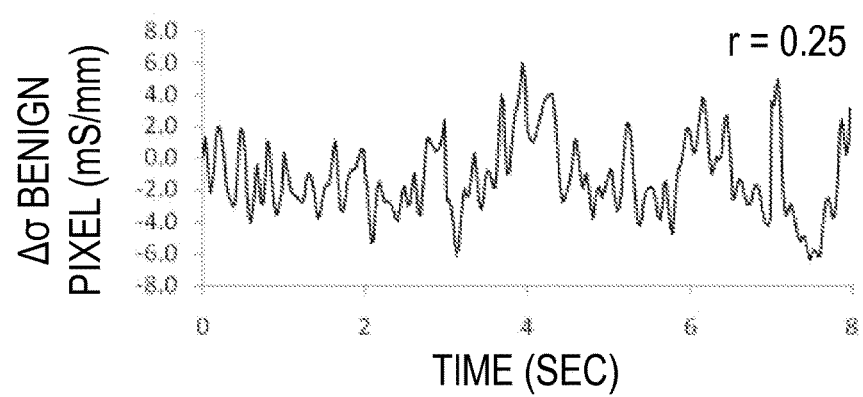
Figure 26E:
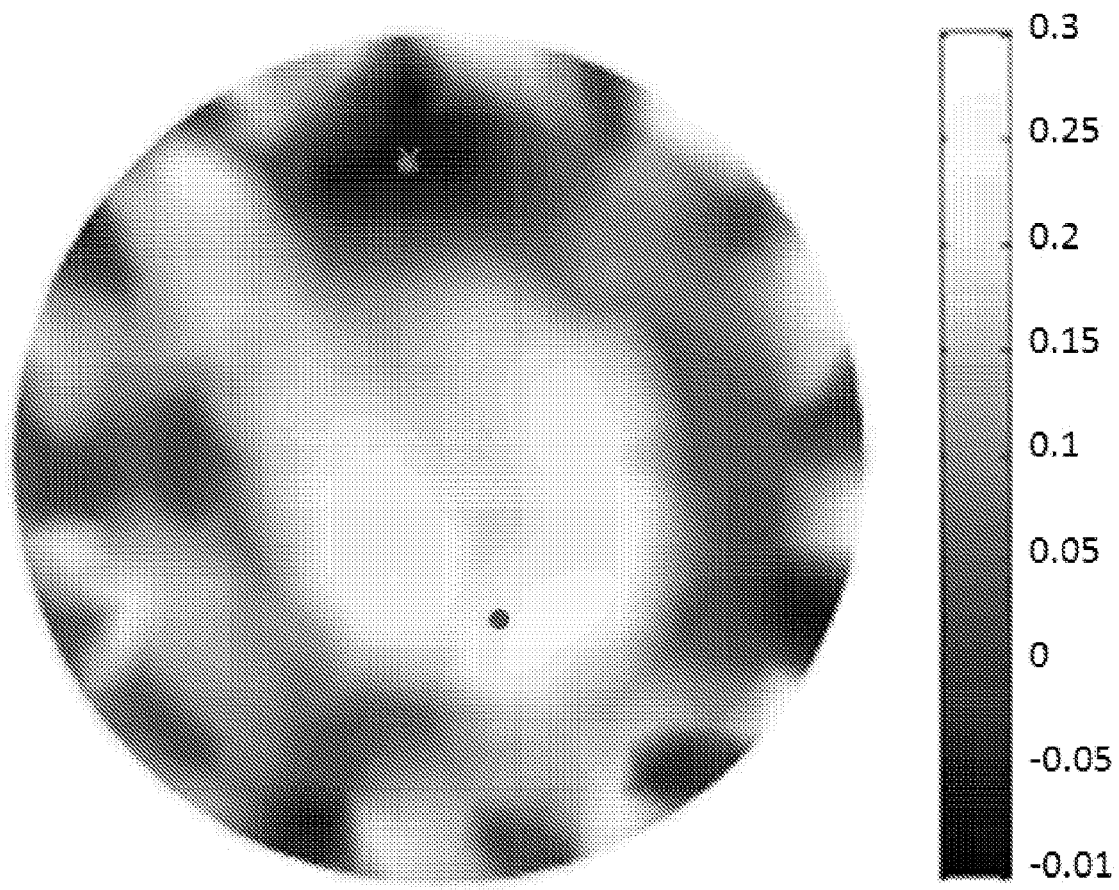

FIGS. 26A-E show a representative sequence of changing conductivity and its correlation with pulsatile oxygen saturation for a woman with a pathologically confirmed inflammatory breast cancer in the upper outer quadrant of her right breast. In this case, the change in conductivity ranged from −7.9 mS/m to 6.3 mS/m with respect to baseline over the course of eight heartbeats, as seen in FIGS. 26A and 26B. No visually-evident signatures differentiated benign from malignant regions within the breast in the raw conductivity images (see FIG. 26A). The change in conductivity (Δσ) at a single image pixel was extracted from benign and malignant regions at each time instant (see FIGS. 26C and 26D). When these dynamic conductivity signatures were phase-shifted and linearly correlated with the oxygen saturation signal (FIG. 26B), substantial differences in the maximum correlation coefficients ($r_{malignant}$=0.04 vs. $r_{benign}$=0.25 for the example shown) were observed. The temporal conductivity sequence at each image pixel was extracted and its correlation with the oxygen saturation signal was computed. The correlation coefficient calculated at each pixel was used to form an image of the correlative power between the pulsatile conductivity and the oxygen saturation signal (see FIG. 26E).

Results—Imaging Women with Breast Cancer

Figures 27A, 27B, 27C:
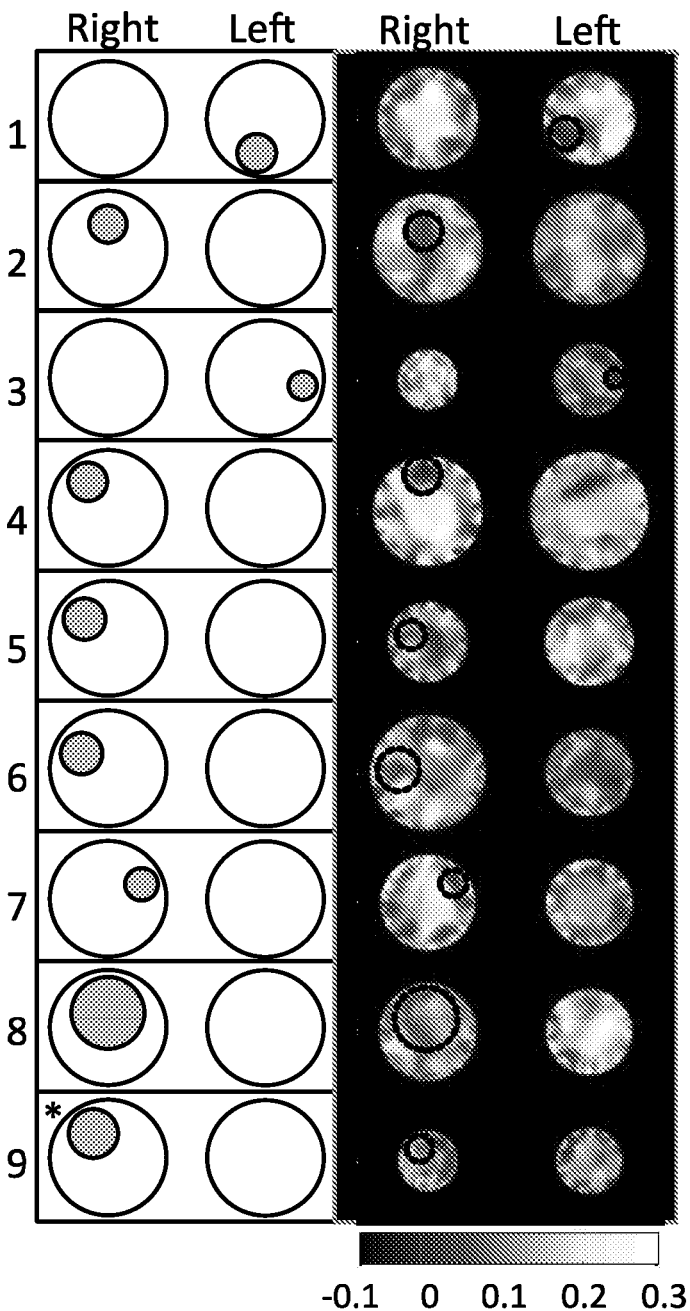
FIGS. 27A-E show results obtained by imaging women with breast cancer.
Figure 27D:
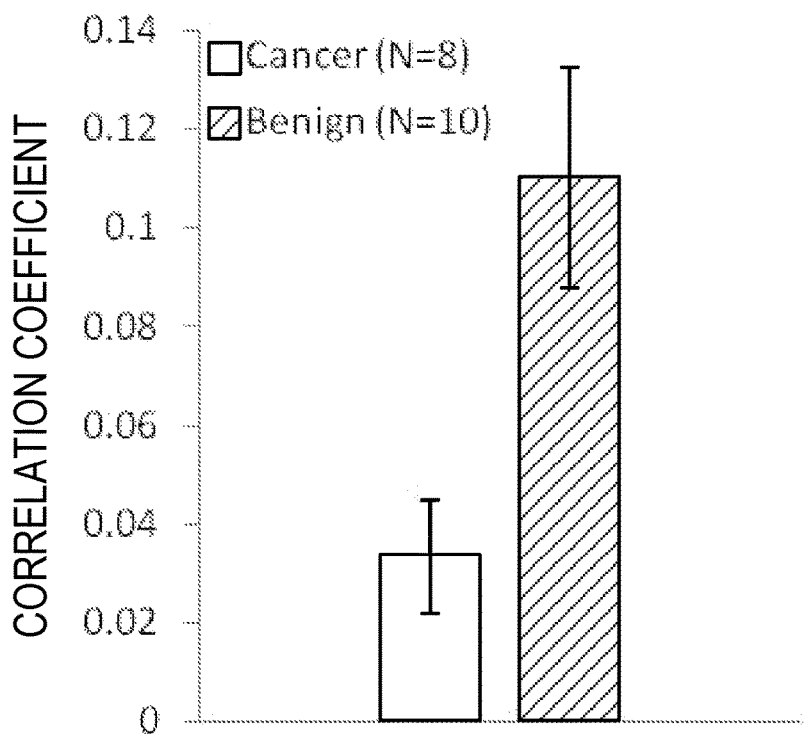
Figure 27E:
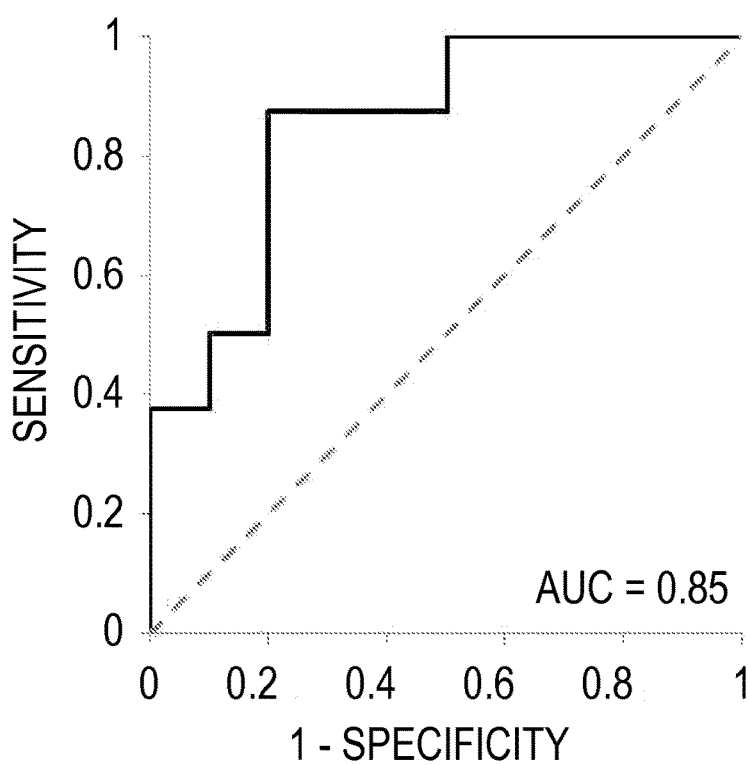

FIGS. 27A-E show results obtained by imaging women with breast cancer. Magnetic resonance (MR) imaging studies were obtained from the nine women with mammographically noted abnormalities, and the lesions were identified by clock face position and size, as shown in FIG. 27A. The corresponding right and left correlation maps were constructed for each of these cases (FIG. 27B). The mean correlation coefficient computed within a user-specified region-of-interest (ROI) surrounding the lesion was compared to a symmetrically designated ROI in the contralateral breast. The tumor ROI was manually selected at a region of low correlation in close proximity to the clinically identified position. The mean correlation coefficient of the cancer ROI was less than that in the symmetric benign ROI in seven of the eight carcinoma cases (FIG. 27C) with the benign-to-cancer ratio ranging from 1.9 to 25.8 (mean±SD: 9.2±9.1). FIG. 28 shows a correlation coefficient table for the abnormal cohort. The tabulated correlation coefficient represents mean value within the specified ROI. The abnormal ROI of patient 9 has benign breast parenchyma. The mean correlation coefficient of all cancer ROIs was 0.0337±0.0318 (mean±SD) and for benign ROIs was 0.1103±0.0716 (mean±SD) and were significantly different (P=0.0064, test power=0.86) (FIG. 27D). Receiver operating characteristic (ROC) curves were constructed to assess the clinical potential for using these metrics to distinguish cancer from benign regions within the breast. The area under the curve (AUC) for this subset of women with previously identified abnormalities was 0.85 (FIG. 27E). At a correlation coefficient threshold of 0.06321 this metric had a sensitivity (SN) of 0.875, specificity (SP) of 0.8, accuracy (ACC) of 0.833, positive predictive value (PPV) of 0.778, and a negative predictive value (NPV) of 0.889.

Results—Comparative Imaging of Women with and without Breast Cancer

Figure 29A:
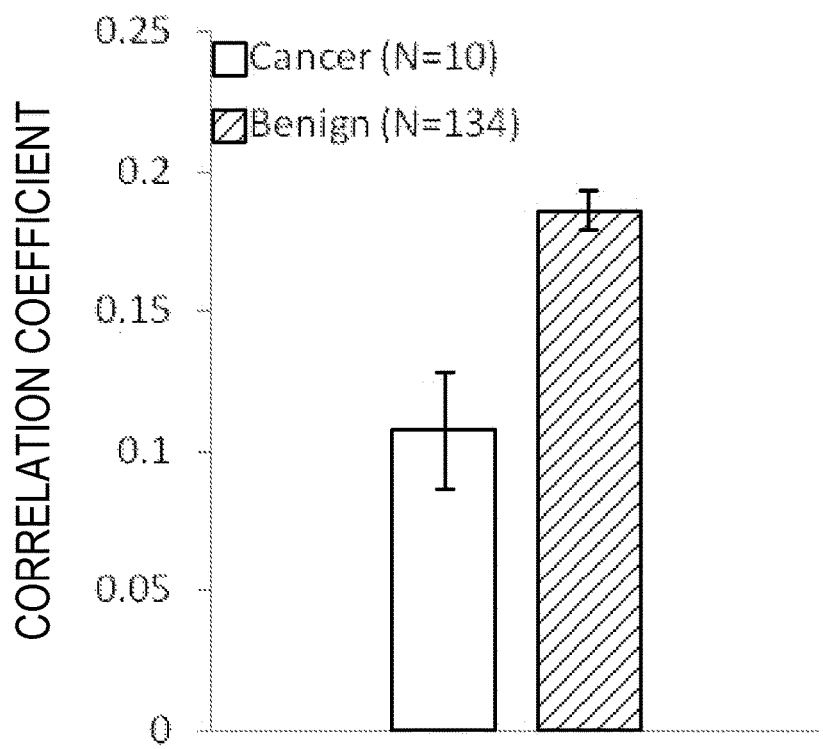
FIGS. 29A and 29B show comparative results for women with and without breast cancer.
Figure 29B:
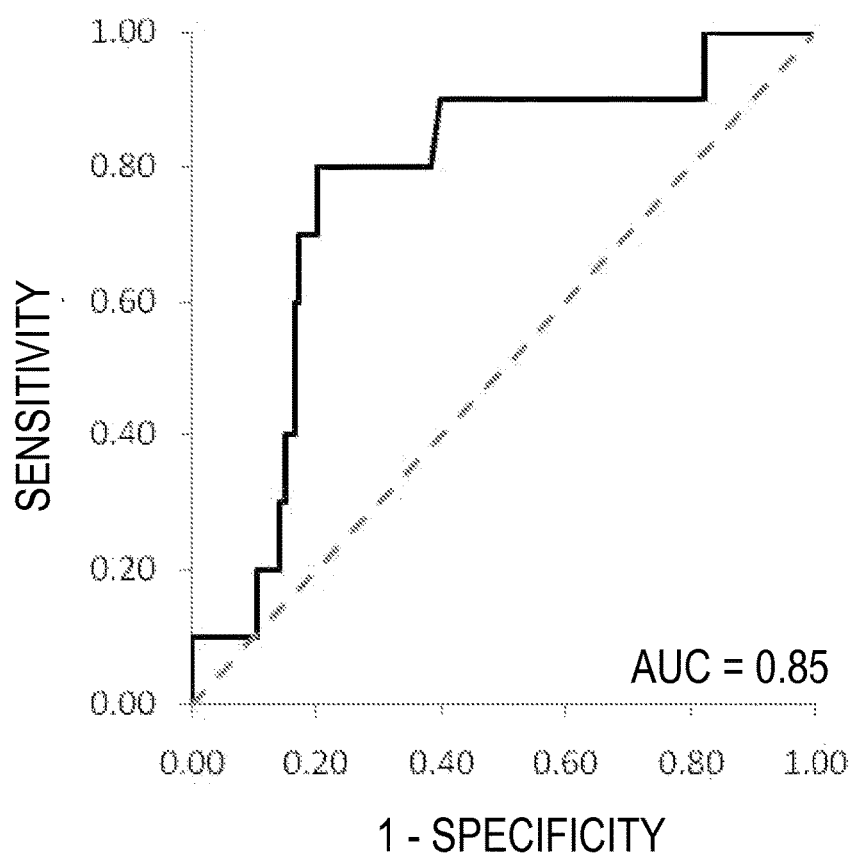

FIGS. 29A and 29B show comparative results for women with and without breast cancer. Correlation maps were constructed for the right and left breast of each of the 18 women enrolled in this study. Instead of selecting specific ROIs associated with regions of low correlation, the four quadrants of each image were selected as a ROI. Based on the MR imaging studies, the quadrants designated at the cardinal locations (NE, SE, SW, NW) were then identified as either malignant or benign. For those patients with lesions identified at the 12:00 location, both NW and NE quadrants were designated as malignant (patients 2 and 8, FIG. 27A). Of the 144 total quadrants (18 women×two breasts×4 quadrants), 10 were identified as malignant and 134 as benign. The mean correlation coefficient within the malignant quadrants (mean±SD: 0.107±0.067) were significantly less than those within the benign quadrants (mean±SD: 0.186±0.088) (P=0.0031, test power=0.96) (FIG. 29A). The AUC computed from this patient population was 0.769 (FIG. 29B) and the clinical metrics obtained at a correlation threshold of 0.118 were 0.8, 0.8, 0.8, 0.23, and 0.98 for SN, SP, ACC, PPV, and NPV, respectively.

Methods—Subjects

Women with mammographically noted abnormal breast lesions were asked to participate in our IRB-approved study. These women underwent pulse-oximetry gated electrical impedance tomography exams, followed by mammography guided biopsy's and magnetic resonance imaging studies in the case of positive invasive carcinoma findings on biopsy. Radiographic review of the MRI produce quantitative measures of lesion size and clock-face location in addition to the qualitative metrics of lesion type, margin morphology, and contrast enhancement pattern and kinetics. An ACR BIRADS category based on MR and mammographic interpretation was assigned to each lesion. This group of women composed the abnormal cohort evaluated in this investigation. A second group of women with no noted abnormal lesions was asked to participate as part of the normal or benign cohort. This group of women did not undergo biopsy or MRI.

Methods—Electrical Impedance Tomography

Each woman participating in the study was imaged using pulse-oximetry gated dynamic electrical impedance tomography (EIT), the same system as used in Example I. Both the left and right breasts were evaluated during each imaging session and a pulse-oximeter sensor was placed on either the index or middle finger of the right hand. Sixteen 1 cm diameter circular Ag/AgCl electrodes arranged in a retractable ring were brought into contact with the circumference of the breast, and the imaging procedure was initiated. The peak of the oxygen saturation signal recorded through pulse-oximetry was used to trigger EIT data acquisition. Multiple frames of EIT data were collected at 20 frames per second and data acquisition occurred over multiple heartbeats (7-10 heartbeats). Concurrently with EIT data acquisition, oxygen-saturation was sampled as a surrogate measure of blood flow. EIT data was collected at 127 kHz—a frequency where variation between the electrical conductivity of blood and both normal and cancerous breast tissue has been reported. The radial diameter of the electrode array was recorded during an exam for use in post data acquisition image formation.

Methods—Image Analysis

As discussed in connection with Example I, a linearized finite element based numerical algorithm was applied to construct conductivity images for each EIT data frame as described previously. This procedure produced a temporal sequence of conductivity maps corresponding to the sampled oxygen-saturation signal. Linear correlation coefficients were computed between the temporal conductivity at a single image location (pixel) and the recorded oxygen saturation signal, and provided a measure of how well the conductivity change was linked to the cardiovascular signature. These correlations were calculated for the full range of phase-lags (0-360 degrees) between the signals, and the maximum correlation independent of the phase-lag was assigned to each image location from which a correlation map was constructed. These maps depict regions where more or less correlation occurred between the oxygen saturation signal (pulsatile blood flow) and the change in conductivity. Additional details regarding signal analysis and imaging processing are provided in Example I.

Methods—Statistical Analysis

Within the abnormal group, we manually selected circular regions of interest (ROI) in close proximity to MRI-based lesion locations that had focal areas of low correlation. The ROI was defined to have a diameter equivalent to the mean of the MRI reported lesion dimensions. A second similarly sized ROI was positioned in the contralateral breast at the mirrored location. The mean correlation coefficient within each ROI was computed and served as the primary variable for comparison. We performed ROC analysis to evaluate the discriminatory power that this correlation metric provided for differentiating malignant from benign regions. Within the abnormal group, ROIs of the tumor-bearing breasts were classified as malignant, while ROIs in the contralateral side were categorized as benign. We calculated the AUC for these curves and determined the classification threshold at which an 80% specificity would be achieved. With this threshold, we computed the clinical parameters of sensitivity, accuracy, positive predictive value, and negative predictive value. In a second analysis, we computed the mean correlation coefficient from each of the four quadrants comprising a correlation map. These means were calculated for both breasts of women in both the abnormal and normal cohorts. Each quadrant was designated as malignant or benign based on clinical image studies (MR and mammography). Similar ROC analysis was performed to assess the discriminatory power of these quadrant correlations. From this analysis sensitivity, specificity, accuracy, positive predictive values, and negative predictive values were computed. In both ROI and quadrant-based analyses, two-group mean-comparison t-tests were constructed to compare the benign and malignant groupings. The power of each comparison was estimated from the computed mean values and standard deviations and the specific group sample sizes. All statistical computations were performed with Stata/IC 10.0 (StataCorp LP, College Station, Tex.) and results were deemed significant for $p<0.01$.

Combinations of Features

Features described above as well as those claimed below may be combined in various ways without departing from the scope hereof. For example, it will be appreciated that aspects of one cardiovascular-dynamics correlated imaging system, or method, described herein may incorporate or swap features of another cardiovascular-dynamics correlated imaging system, or method, described herein. The following examples illustrate possible, non-limiting combinations of embodiments described above. It should be clear that many other changes and modifications may be made to the systems and methods described herein without departing from the spirit and scope of this invention:

(A1) A method for cardiovascular-dynamics correlated imaging may include receiving a time series of images of at least a portion of a patient, receiving a time series of cardiovascular data for the patient, and evaluating correlation between the time series of images and the time series of cardiovascular data.

(A2) The method denoted as (A1) may further include determining a property of the at least a portion of a patient, based upon the correlation between the time series of images and the time series of cardiovascular data.

(A3) In the method denoted as (A2), the property may be presence or non-presence of vascularized cancer tissue in the at least a portion of a patient.

(A4) The method denoted as (A3) may further include, if the step of determining results in determining presence of vascularized cancer tissue, diagnosing the patient with tumor angiogenesis.

(A5) In the method denoted as (A2), the property may be amount or type of vascularized tissue in the at least a portion of a patient.

(A6) The method denoted as (A5) may further include assessing progression of tumor angiogenesis from the amount or type of vascularized tissue.

(A7) In any of the methods denoted as (A1) through (A6), the step of receiving a time series of images may include receiving a time series of electrical impedance tomography images.

(A8) In the method denoted as (A7), the step of receiving a time series of electrical impedance tomography images may include receiving a time series of single-frequency electrical impedance tomography images.

(A9) In the method denoted as (A7), the step of receiving a time series of electrical impedance tomography images may include receiving a time series of multi-frequency electrical impedance tomography images.

(A10) In any of the methods denoted as (A1) through (A6), in the step of receiving a time series of images, the time series of images may be selected from the group consisting of a time series of ultrasound images, a time series of video endoscopy images, and a time series of fluoroscopy images.

(A11) In any of the methods denoted as (A1) through (A6), in the step of receiving a time series of images, the time series of images may be selected from the group consisting of a time series of magnetic resonance images and a time series of computed tomography images.

(A12) In any of the methods denoted as (A1) through (A11), the time series of images may define a plurality of time series of images, and each of the plurality of time series of images may be gated by the time series of cardiovascular data to a different respective phase relative to the time series of cardiovascular data.

(A13) In any of the methods denoted as (A1) through (A12), the step of receiving a time series of cardiovascular data may include receiving a time series of pulse-oximetry data.

(A14) In any of the methods denoted as (A1) through (A12), in the step of receiving a time series of cardiovascular data, the time series of cardiovascular data may be selected from a time series of electrocardiogram data, a time series of arterial pressure data, and a time series of blood flow data.

(A15) In any of the methods denoted as (A1) through (A14), the step of evaluating correlation may include evaluating at least one of spectral correlation and temporal correlation between the time series of images and the time series of cardiovascular data.

(A16) In any of the methods denoted as (A1) through (A15), the step of evaluating correlation may include analyzing correlation between the time series of images and heartbeat cycles identified from the time series of cardiovascular data.

(A17) In the method denoted as (A16), the step of evaluating correlation may include (a) detecting at least one cardiovascular signature in the time series of cardiovascular data to identify at least one heartbeat cycle, (b) referencing the time series of images to timing of the at least one heartbeat cycle, and (c) analyzing the time series of images as a function of timing within a heartbeat cycle.

(A18) In the method denoted as (A17), the step of referencing may include, if the heartbeat rate is not constant, resampling the time series of cardiovascular data, and in accordance therewith the time series of images, to emulate a constant heartbeat rate.

(A19) In any of the methods denoted as (A16) through (A18), the step of analyzing correlation may include (a) extracting, from the time series of images, a respective time series of position sensitive signals each representing same spatial region of interest of the time series of images, and (b) analyzing the time series of position sensitive signals as a function of timing within heartbeat cycles.

(A20) In the method denoted as (A19), the step of analyzing the time series of position sensitive signals may include determining one or more parameters indicative of correlation between the time series of position sensitive signals and the time series of cardiovascular data, wherein the time series of signals and the time series of cardiovascular data are referenced to the heartbeat cycles.

(A21) In the method denoted as (A20), the step of analyzing the time series of position sensitive signals may further include combining two or more of the parameters indicative of correlation to assess degree of correlation.

(A22) In any of the methods denoted as (A20) and (A21), the step of determining one or more parameters indicative of correlation may include calculating at least one of spectral correlation coefficient and maximum temporal correlation coefficient.

(A23) In the method denoted as (A22), the step of calculating maximum temporal correlation coefficient may include (a) calculating the temporal correlation coefficient as a function of phase shift between the time series of position sensitive signals and the time series of cardiovascular data, and (b) determining the maximum value of the temporal correlation coefficient as a function of the phase shift.

(A24) In any of the methods denoted as (A20) and (A21), the step of determining one or more parameters indicative of correlation may include (a) calculating the temporal correlation coefficient as a function of phase shift between the time series of position sensitive signals and the time series of cardiovascular data, and (b) determining the phase shift at which the temporal correlation coefficient as a function of the phase shift attains maximum value.

(A25) In any of the methods denoted as (A20) and (A21), the step of determining one or more parameters indicative of correlation may include at least one of (a) comparing temporal distributions of the time series of position sensitive signals and the time series of cardiovascular data and (b) comparing spectral distributions of the time series of position sensitive signals and the time series of cardiovascular data.

(A26) In any of the methods denoted as (A19) through (A25), the step of analyzing the time series of position sensitive signals may include evaluating spectral distribution of the time series of position sensitive signals as a function of timing within heartbeat cycles.

(A27) In the method denoted as (A26), the step of evaluating spectral distribution may include determining one or more spectral power ratios of the time series of position sensitive signals.

(A28) Any of the methods denoted as (A19) through (A27) may further include selecting the spatial region of interest.

(A29) In any of the methods denoted as (A1) through (A28), the time series of images may be a time series of first-type images, and the method may further include overlaying at least a portion of the time series of first-type images on a time series of second-type images of a second portion of the patient, the second-type images being of type different from the first-type images.

(A30) In the method denoted as (A29), the first-type images may be electrical impedance tomography images and the second-type images may be selected from the group consisting of ultrasound images, magnetic resonance images, positron emission tomography images, and computed tomography images.

(A31) In any of the methods denoted as (A29) and (A30), the step of overlaying may include overlaying, with the time series of second-type images, a portion of the time series of first-type images meeting criteria of correlation with the time series of cardiovascular data.

(A32) Any of the methods denoted as (A1) through (A31) may further include generating at least one correlation-indicating image indicating correlation between the time series of images and the time series of cardiovascular data.

(A33) The method denoted as (A32) may further include overlaying the at least one correlation-indicating image on the time series of images.

(A34) In any of the methods denoted as (A32) and (A33), the time series of images may be a time series of first-type images, and the method may further include (a) generating a time series of second-type images of a second portion of the patient having a spatial overlap with the at least a portion of a patient, wherein the second-type images are of type different from the first-type images, and (b) overlaying the at least one correlation-indicating image on the time series of second-type images.

(A35) In the method denoted as (A34), the step of generating a time series of second-type images may be performed concurrently with the step of generating the time series of images.

(A36) In each of the methods denoted as (A1) through (A33), the time series of images may be a time series of a first-type images and the method may further include (a) receiving at least one second-type image of a second portion of the patient having a spatial overlap with the at least a portion of a patient, and (b) using the at least one second-type image to determine a spatial region of interest of the first time series of first-type images to be considered in the step of evaluating correlation.

(A37) In the method denoted as (A36), the first-type images may be electrical impedance tomography images and the second-type images may be selected from the group consisting of ultrasound images, magnetic resonance images, and computed tomography images.

(A38) Any of the methods denoted as (A1) through (A37) may further include generating the time series of images, and recording the time series of cardiovascular data.

(A39) In the method denoted as (A38), the step of generating a time series of images may include generating a time series of images at a first series of times, the step of recording a time series of cardiovascular data may include recording a time series of cardiovascular data at a second series of times, and the step of evaluating correlation may include resampling at least one of the time series of images and the time series of cardiovascular data to synchronize the first series of times and the second series of times.

(A40) In any of the methods denoted as (A38) and (A39), the step of generating the time series of images may include generating a time series of electrical impedance tomography images.

(A41) In the method denoted as (A40), the step of generating a time series of electrical impedance tomography image may include, for each electrical impedance tomography image, (a) measuring a plurality of voltages or currents at a respective plurality of spatially separated electrodes in contact with the patient, and (b) reconstructing the electrical impedance tomography image from the plurality of voltages, wherein the electrical impedance tomography image is a spatial distribution of change of an electrical impedance related property as compared to a reference distribution of the electrical impedance related property.

(A42) In the method denoted as (A41), the step of reconstructing may include applying a finite element based linear difference algorithm.

(B1) A system for cardiovascular-dynamics correlated imaging may include a processing device having (a) a processor, (b) a memory communicatively coupled with the processor, and (c) a correlation module including machine-readable instructions stored in the memory that, when executed by the processor, perform the function of correlating a time series of images of at least a portion of a patient with a time series of cardiovascular data of the patient to determine a property of the at least a portion of a patient.

(B2) The system denoted as (B1) may further include an imaging device for generating at least one of (a) the time series of images and (b) data from which the time series of images can be reconstructed.

(B3) In the system denoted as (B2), the imaging device may be an electrical impedance tomography device.

(B4) In the system denoted as (B2), the imaging device may be selected from the group consisting of an ultrasonograph, a video endoscope, a fluoroscope, a magnetic resonance scanner, and a computed tomography scanner.

(B5) Any of the systems denoted as (B1) through (B4) may further include a cardiovascular measurement device for recording the time series of cardiovascular data.

(B6) In the system denoted as (B5), the cardiovascular measurement device may be a pulse oximeter.

(B7) In the system denoted as (B5), the cardiovascular measurement device may be selected from the group consisting of an electrocardiograph, a sphygmomanometer, and a blood flow measurement device.

(B8) Any of the systems denoted as (B1) through (B7) may further include an image reconstruction module having machine-readable instructions stored in the memory that, when executed by the processor, perform the function of reconstructing the time series of images from a time series of position sensitive data.

(B9) In the system denoted as (B8), the image reconstruction module may include machine-readable instructions stored in the memory that, when executed by the processor, perform the function of reconstructing the time series of images from the time series of position sensitive data using at least one of a finite element based linear difference algorithm, a boundary element method, and back projection.

(B10) In the system denoted as (B8), the image reconstruction module may include machine-readable instructions stored in the memory that, when executed by the processor, perform the function of reconstructing a time series of electrical impedance tomography images from a time series of position sensitive voltage measurements obtained using electrodes in contact with the at least a portion of a patient, wherein the time series of electrical impedance tomography images is a spatial distribution of electrical conductivity change as compared to a reference electrical conductivity distribution.

(B11) Any of the systems denoted as (B1) through (B10) may further include a resampling module including machine-readable instructions stored in the memory that, when executed by the processor, perform the function of resampling a time series of data from a series of times, at which the time series of data is generated, to a desired series of times.

(B12) In the system denoted as (B11), the resampling module may further include machine-readable instructions stored in the memory that, when executed by the processor, perform the function of resampling, if the time series of images and the time series of cardiovascular data are associated with different series of times, at least one of the time series of images and the time series of cardiovascular data to synchronize the time series of images and the time series of cardiovascular data.

(B13) Any of the systems denoted as (B1) through (B12) may further include a signature identification module with machine-readable instructions stored in the memory that, when executed by the processor, perform the function of identifying a time series of cardiovascular signatures in the time series of cardiovascular data.

(B14) In the system denoted as (B13), the signature identification module may further include machine-readable instructions stored in the memory that, when executed by the processor, perform the function identifying heartbeat cycles from the time series of cardiovascular signatures.

(B15) The system denoted as (B14) may further include a resampling module with machine-readable instructions stored in the memory that, when executed by the processor, perform the function of resampling, if heartbeat rate of patient is not constant, the time series of images and the time series of cardiovascular data to produce a heartbeat rate regularized time series of images and a heartbeat regularized time series of cardiovascular data, wherein the heartbeat rate regularized time series of images and the heartbeat regularized time series of cardiovascular data emulate a constant heartbeat rate.

(B16) In any of the systems denoted as (B1) through (B16), the correlation module may include machine-readable instructions stored in the memory that, when executed by the processor, perform the function of (a) extracting, from the time series of images, a respective time series of position sensitive signals each representing same spatial portion of the time series of images, and (b) analyzing the time series of position sensitive signals as a function of timing within heartbeat cycles.

(B17) In the system denoted as (B16), the correlation module may include machine-readable instructions stored in the memory that, when executed by the processor, perform the function of evaluating spectral distribution of the time series of position sensitive signals as a function of timing within heartbeat cycles.

(B18) In the system denoted as (B17), the correlation module may include machine-readable instructions stored in the memory that, when executed by the processor, perform the function of evaluating at least one of spectral correlation and temporal correlation between the time series of images and the time series of cardiovascular data.

(B19) In any of the systems denoted as (B1) through (B18), the correlation module may include machine-readable instructions stored in the memory that, when executed by the processor, perform the function of calculating at least one parameter indicative of correlation between the time series of images and the time series of cardiovascular data.

(B20) In the system denoted as (B19), the at least one parameter may be selected from the group consisting of spectral correlation coefficient, maximum temporal correlation coefficient when varying phase between the time series of images and the time series of cardiovascular data, and phase at which maximum temporal correlation coefficient is attained.

(B21) Any of the systems denoted as (B1) through (B20) may further include an overlay module including machine-readable instructions stored in the memory that, when executed by the processor, perform the function of overlaying a time series of correlation-indicating images indicative of correlation between the time series of images and the time series of cardiovascular data on at least one second image of type different from the images of the time series of images.

(B22) In the system denoted as (B21), the at least one second image may be a time series of second images.

Changes may be made in the above systems and methods without departing from the scope hereof. It should thus be noted that the matter contained in the above description and shown in the accompanying drawings should be interpreted as illustrative and not in a limiting sense. The following claims are intended to cover generic and specific features described herein, as well as all statements of the scope of the present system and method, which, as a matter of language, might be said to fall therebetween.

What is claimed is:

1. A method for cardiovascular-dynamics correlated imaging, comprising:
    generating a time series of images at a first series of times;
    recording a time series of cardiovascular data at a second series of times;
    evaluating correlation between the time series of images and the time series of cardiovascular data, said evaluating correlation including resampling at least one of the time series of images and the time series of cardiovascular data to synchronize the first series of times and the second series of times;
    identifying vascularized tissue of the patient based upon the correlation; and
    determining a property of the patient, relating to the vascularized tissue, based upon the correlation.

2. The method of claim 1, the step of generating a time series of images comprising generating a time series of electrical impedance tomography images.

3. The method of claim 1, the step of generating a time series of cardiovascular data comprising generating a time series of pulse-oximetry data.

4. The method of claim 1, the step of evaluating correlation comprising analyzing correlation between the time series of images and heartbeat cycles identified from the time series of cardiovascular data.

5. The method of claim 1, further comprising generating at least one correlation-indicating image indicating correlation between the time series of images and the time series of cardiovascular data.

6. The method of claim 5, further comprising overlaying the at least one correlation-indicating image on the time series of images.

7. The method of claim 1, the property being presence or non-presence of vascularized cancer tissue in the at least a portion of a patient.

8. The method of claim 1, the property being amount or type of vascularized tissue in the at least a portion of a patient.

9. A method for cardiovascular-dynamics correlated imaging, comprising:
    receiving a time series of images of at least a portion of a patient;
    receiving a time series of cardiovascular data for the patient;
    evaluating correlation between the time series of images and the time series of cardiovascular data, said evaluating correlation including:
        (a) detecting at least one cardiovascular signature in the time series of cardiovascular data to identify at least one heartbeat cycle,
        (b) referencing the time series of images to timing of the at least one heartbeat cycle, and
        (c) analyzing the time series of images as a function of timing within a heartbeat cycle;
    identifying vascularized tissue of the patient based upon the correlation between the time series of images and the at least one heartbeat cycle; and
    determining a property of the patient, relating to the vascularized tissue, based upon the correlation between the time series of images and the at least one heartbeat cycle.

10. The method of claim 9, the step of referencing comprising, if heartbeat rate is not constant, resampling the time series of cardiovascular data, and in accordance therewith the time series of images, to emulate a constant heartbeat rate.

11. A method for cardiovascular-dynamics correlated imaging, comprising:
    receiving a time series of images of at least a portion of a patient;
    receiving a time series of cardiovascular data for the patient;
    evaluating correlation between the time series of images and the time series of cardiovascular data, said evaluating correlation including analyzing correlation between the time series of images and heartbeat cycles identified from the time series of cardiovascular data, said analyzing correlation including:
        (a) extracting, from the time series of images, a respective time series of position sensitive signals each representing same spatial region of interest of the time series of images, and
        (b) analyzing the time series of position sensitive signals as a function of timing within heartbeat cycles;
    identifying vascularized tissue of the patient based upon the correlation between the time series of images and the heartbeat cycles; and
    determining a property of the patient, relating to the vascularized tissue, based upon the correlation between the time series of images and the heartbeat cycles.

12. The method of claim 11, the step of analyzing the time series of position sensitive signals comprising determining one or more parameters indicative of correlation between the time series of position sensitive signals and the time series of cardiovascular data, the time series of signals and the time series of cardiovascular data being referenced to the heartbeat cycles.

13. The method of claim 12, the step of determining one or more parameters indicative of correlation comprising:
    calculating temporal correlation coefficient as a function of phase shift between the time series of position sensitive signals and the time series of cardiovascular data; and
    determining maximum value of the temporal correlation coefficient as a function of the phase shift.

14. The method of claim 12, the step of determining one or more parameters indicative of correlation comprising:

calculating temporal correlation coefficient as a function of phase shift between the time series of position sensitive signals and the time series of cardiovascular data; and determining phase shift at which the temporal correlation coefficient as a function of the phase shift attains maximum value.

15. The method of claim 12, the step of determining one or more parameters indicative of correlation comprising at least one of (a) comparing temporal distributions of the time series of position sensitive signals and the time series of cardiovascular data and (b) comparing spectral distributions of the time series of position sensitive signals and the time series of cardiovascular data.

16. The method of claim 11, the step of analyzing the time series of position sensitive signals comprising evaluating spectral distribution of the time series of position sensitive signals as a function of timing within heartbeat cycles.

17. A method for cardiovascular-dynamics correlated imaging, comprising:

receiving a time series of images of at least a portion of a patient, the time series of images being a time series of first-type images;

receiving a time series of cardiovascular data for the patient;

evaluating correlation between the time series of images and the time series of cardiovascular data;

identifying vascularized tissue of the patient based upon the correlation;

determining a property of the patient, relating to the vascularized tissue, based upon the correlation; and overlaying at least a portion of the time series of first-type images on a portion of a time series of second-type images meeting criteria of correlation with the time series of cardiovascular data, the second-type images being of a second portion of the patient and of type different from the first-type images.

18. A method for cardiovascular-dynamics correlated imaging, comprising:

receiving a time series of images of at least a portion of a patient, the time series of images being a time series of first-type images;

receiving a time series of cardiovascular data for the patient;

evaluating correlation between the time series of images and the time series of cardiovascular data;

identifying vascularized tissue of the patient based upon the correlation;

determining a property of the patient, relating to the vascularized tissue, based upon the correlation;

generating at least one correlation-indicating image indicating correlation between the time series of images and the time series of cardiovascular data;

generating a time series of second-type images of a second portion of the patient having a spatial overlap with the at least a portion of a patient, the second-type images having type different from the first-type images; and overlaying the at least one correlation-indicating image on the time series of second-type images.

* * * * *